US012679801B2

(12) United States Patent
Zha et al.

(10) Patent No.: US 12,679,801 B2
(45) Date of Patent: Jul. 14, 2026

(54) AMINO LIPID AND PREPARATION METHOD AND APPLICATION THEREOF

(71) Applicant: Shenzhen MagicRNA Biotechnology Co., Ltd., Shenzhen (CN)

(72) Inventors: Gaofeng Zha, Shenzhen (CN); Yuexiao Hu, Shenzhen (CN); Xinghua Peng, Shenzhen (CN); Wanyin Fang, Shenzhen (CN)

(73) Assignee: Shenzhen MagicRNA Biotechnology Co., Ltd., Shenzhen (CN)

( * ) Notice: Subject to any disclaimer, the term of this patent is extended or adjusted under 35 U.S.C. 154(b) by 80 days.

(21) Appl. No.: 18/100,596

(22) Filed: Jan. 24, 2023

(65) Prior Publication Data

US 2023/0348360 A1 Nov. 2, 2023

(30) Foreign Application Priority Data

Jan. 25, 2022 (CN) ......................... 202210082815.3

(51) Int. Cl.
*C07C 219/08* (2006.01)
*A61K 47/28* (2006.01)
*C07D 211/62* (2006.01)

(52) U.S. Cl.
CPC ............ *C07C 219/08* (2013.01); *A61K 47/28* (2013.01); *C07D 211/62* (2013.01)

(58) Field of Classification Search
CPC ...... C07C 219/08; A61K 47/28; C07D 211/62
See application file for complete search history.

(56) References Cited

U.S. PATENT DOCUMENTS

| | | | | |
|---|---|---|---|---|
| 10,059,655 | B2 * | 8/2018 | Brito | C07D 207/16 |
| 11,633,480 | B2 * | 4/2023 | Maier | C07D 207/32 562/571 |
| 2005/0032893 | A1 | 2/2005 | Wong | |
| 2011/0065769 | A1 | 3/2011 | Wong | |
| 2016/0311759 | A1 | 10/2016 | Brito et al. | |

FOREIGN PATENT DOCUMENTS

CN 104119227 A 10/2014

OTHER PUBLICATIONS

Zhao, Y., Wang, W., Li, J., Wang, F., Zheng, X., Yun, H., Zhao, W. and Dong, X., 2013. FeCl3/pyridine: dual-activation in opening of epoxide with carboxylic acid under solvent free condition. Tetrahedron Letters, 54(44), pp. 5849-5852. (Year: 2013).*
Zhang et al 2021. Lipids and lipid derivatives for RNA delivery. Chemical reviews, 121(20), pp. 12181-12277 (Year: 2021).*

* cited by examiner

*Primary Examiner* — James H Alstrum-Acevedo
*Assistant Examiner* — Carolyn L. Ladd
(74) *Attorney, Agent, or Firm* — HAUPTMAN HAM, LLP

(57) ABSTRACT

An amino lipid and its preparation method as well as an application thereof is provided, and also provided are ionizable amino lipids with a general formula as shown in Formula (I), or pharmaceutically acceptable salts thereof. The amino lipids are used for delivering nucleic acids and small-molecule drugs. The amino lipid compounds have two ester bonds, which enhance the lysosome escape capability of the ionizable amino lipids, and are favorable for the release of delivery targets of a targeted drug or gene, etc., thus improving the delivery efficiency, and showing the capability of delivering nucleic acids into cells in the in-vitro and in-vivo delivery studies.

10 Claims, 4 Drawing Sheets

| | |
|---|---|
| A | 176.231 |
| B | 172.978 |
| C | 77.316 |
| D | 76.993 |
| E | 76.679 |
| F | 71.508 |
| G | 64.475 |
| H | 58.785 |
| I | 45.693 |
| J | 45.386 |
| K | 32.373 |
| L | 32.184 |
| M | 31.870 |
| N | 31.846 |
| O | 31.681 |
| P | 30.785 |
| Q | 29.567 |
| R | 29.528 |
| S | 29.449 |
| T | 29.292 |
| U | 29.268 |
| V | 29.229 |
| W | 27.429 |
| X | 27.390 |
| Y | 25.111 |
| Z | 22.950 |
| $A_1$ | 22.644 |
| $A_2$ | 22.589 |
| $A_3$ | 14.070 |
| $A_4$ | 14.039 |

AMINO LIPID AND PREPARATION METHOD AND APPLICATION THEREOF

TECHNICAL FIELD

The disclosure relates to the technical field of medical chemistry, in particular to an amino lipid and its preparation method as well as an application thereof.

BACKGROUND

Nucleic acid drugs have very wide application prospects in aspects of prevention and treatment of cancer, infectious diseases, genetic diseases, and cardiovascular diseases. However, RNA, DNA, and siRNA etc. are easily degraded in vivo, and the bioavailability is very low when direct administration of oral administration or intravenous injection is used. Therefore, the delivery by vectors is required.

Commonly used nucleic acid vectors include viral vectors and non-viral vectors. Viral vectors have high transfection efficiency, but they lack targeted performance, and have greater safety concerns, low vector capacity and high production cost. Non-viral vectors have the advantages of high safety, easy modification of vector molecules, etc., are suitable for mass production, and have wide application prospects. The application of an LNP (Lipid Nanoparticles) delivery system plays a leading role. The LNP generally consists of ionizable or cationic lipids, phosphonates, cholesterol and pegylated lipids. All of them are amphiphilic molecules with self-assembly performance in structure, and LNPs have gathered significant attention due to the defined and reproducible structure of its component, which enables good reproducibility, easy quality supervision, long in-vivo circulation time, and good biocompatibility, etc. After entering the cells, the nanoparticles need to escape from the endosome/lysosome to release RNA in the cytoplasm, so that it can be expressed to produce the target protein. However, the escape rate of the LNP from the endosome/lysosome is generally low at present. Although DLin-MC3-DMA, as the "gold standard" for evaluation in amino lipids, is the most efficient amino lipid at present, and is approved by FDA for the first siRNA therapeutic drug Patisiran sodium, but only 1%-4% of RNA escapes from the endosome/lysosome. The escape from the endosome/lysosome has become a key step affecting nucleic acid delivery. Therefore, it is of great research significance and practical need to design an amino lipid with good nucleic acid entrapping capacity and high escape capacity from the endosome/lysosome to solve the nucleic acid delivery problem.

SUMMARY

By aiming at the technical problems of low transfection efficiency, cytotoxicity due to positive charges, etc. in the prior art, the disclosure provides an amino lipid and an application thereof.

The objective of the disclosure is achieved through the following technical solution:

In a first aspect, the disclosure provides:

An amino lipid with a structure as shown in Formula (I):

(I)

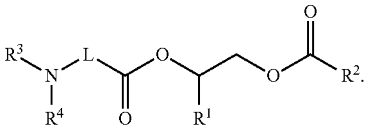

In Formula (I), L is $C_1$-$C_6$ alkylene, $C_1$-$C_6$ alkenylene, $C_1$-$C_6$ alkynylene, $C_3$-$C_6$ cycloalkylene and $C_3$-$C_6$ cycloalkenylene; $R^1$ and $R^2$ are identical or different, and are each independently selected from $C_1$-$C_{20}$ alkyl, $C_1$-$C_{20}$ alkenyl, $C_1$-$C_{20}$ alkynyl, $C_1$-$C_{20}$ cycloalkyl, $C_1$-$C_{20}$ cycloalkenyl and $C_1$-$C_{20}$ cycloalkynyl; the $C_1$-$C_{20}$ alkyl, $C_1$-$C_{20}$ alkenyl, $C_1$-$C_{20}$ alkynyl, $C_1$-$C_{20}$ cycloalkyl, $C_1$-$C_{20}$ cycloalkenyl and $C_1$-$C_{20}$ cycloalkynyl are able to be optionally substituted by H, $C_1$-$C_6$ hydrocarbyl and F;

$R^3$ and $R^4$ are identical or different, and are each independently selected from H, $C_1$-$C_{10}$ alkyl, $C_2$-$C_{10}$ alkenyl and $C_2$-$C_{10}$ alkynyl; the $C_1$-$C_{10}$ alkyl, $C_2$-$C_{10}$ alkenyl and $C_2$-$C_{10}$ alkynyl are able to be optionally substituted by $C_1$-$C_6$ hydrocarbyl; or $R^3$ and $R^4$ are connected to form a 4 to 10-membered heterocyclic ring, the multi-membered heterocyclic ring includes 1 to 6 heteroatoms, and the heteroatoms are selected from N, S and O.

Preferably, $R^1$ is selected from $C_4$-$C_{17}$ alkyl, $C_4$-$C_{17}$ alkenyl, $C_4$-$C_{17}$ alkynyl, $C_4$-$C_{17}$ cycloalkyl, $C_4$-$C_{17}$ cycloalkenyl and $C_4$-$C_{17}$ cycloalkynyl; the $C_4$-$C_{17}$ alkyl, $C_4$-$C_{17}$ alkenyl, $C_4$-$C_{17}$ alkynyl, $C_4$-$C_{17}$ cycloalkyl, $C_4$-$C_{17}$ cycloalkenyl and $C_4$-$C_{17}$ cycloalkynyl are able to be optionally substituted by H, $C_1$-$C_6$ hydrocarbyl and F.

Preferably, the $R^1$ is one selected from E1, E2, E3, E4, E5, E6, E7, E8, E9, E10, E11, E12, E13, E14, E15, E16, E17, E18, E19, E20, E21, E22, E23, E24 or E25:

E1

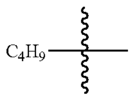

E2

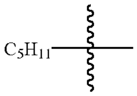

E3

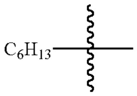

E4

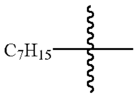

E5

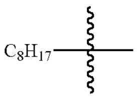

-continued

E6

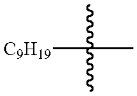

E7

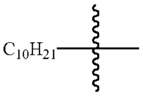

E8

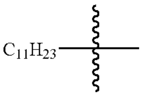

E9

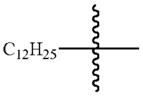

E10

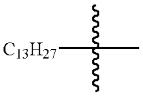

E11

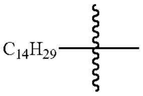

E12

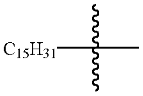

E13

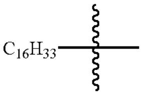

E14

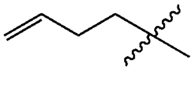

E15

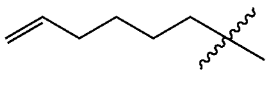

E16

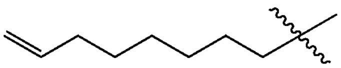

E17

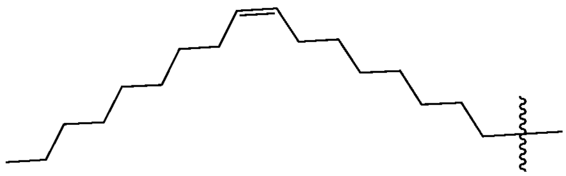

E18

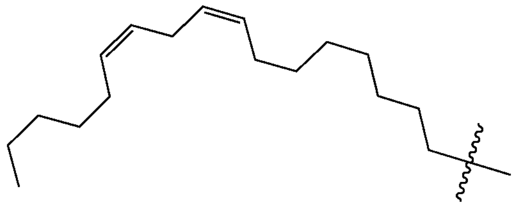

-continued

E19

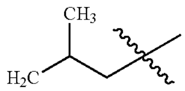

E20

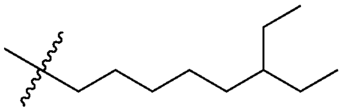

E21

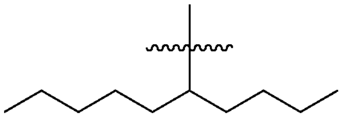

E22

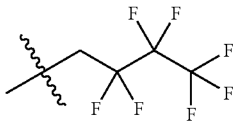

E23

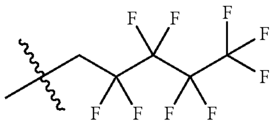

E24

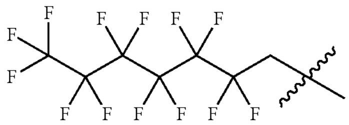

E25

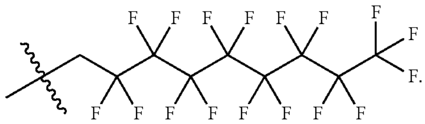

More preferably, the $R^1$ is one selected from E3, E4, E5, E6, E7, E8, E9, E10, E11, E12, E13, E15, E17, E18, E20, E21 or E24.

Preferably, the $R^2$ is selected from $C_5$-$C_{19}$ alkyl, $C_5$-$C_{19}$ alkenyl, $C_5$-$C_{19}$ alkynyl, $C_5$-$C_{19}$ cycloalkyl, $C_5$-$C_{19}$ cycloalkenyl and $C_5$-$C_{19}$ cycloalkynyl; the $C_5$-$C_{19}$ alkyl, $C_5$-$C_{19}$ alkenyl, $C_5$-$C_{19}$ alkynyl, $C_5$-$C_{19}$ cycloalkyl, $C_5$-$C_{19}$ cycloalkenyl and $C_5$-$C_{19}$ cycloalkynyl are able to be optionally substituted by H, $C_1$-$C_6$ hydrocarbyl and F.

Preferably, the $R^2$ is one selected from C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C34, C35, C36, C37, C38, C39, C40, C41, C42, C43, C44, C45, C46, C47, C48, C49, C50, C51, C52, C53, C54, C55, C56, C57, C58, C59, C60, C61, C62, C63, C64, C65, C66, C67, C68, C69, C70, C71, C72, C73, C74, C75, C76, C77, C78, C79, C80, C81, C82, C83, C84, C85, C86, C87, C88, C89, C90, C91, C92, C93, C94, C95, C96, C97, C98, C99, C100, C101, C102, C103, C104, C105, C106, C107, C108, C109, C110, C111, C112, C113, C114, C115, C116, C117, C118, C119, C120, C121, C122, C123, C124, C125, C126, C127, C128, C129, C130, C131, C132, C133, C134, C135, C136, C137, C138, C139, C140, C141, C142, C143, C144, C145, C146, C147:

C1
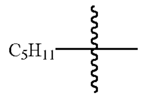
C2
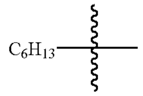
C3
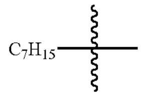
C4
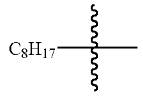
C5
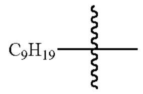
C6
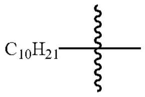
C7
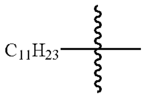
C8
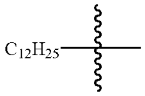
C9
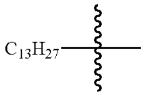
C10
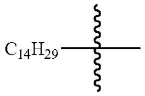
C11
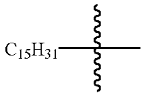
C12
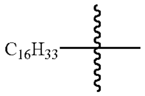
C13
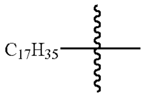
C14
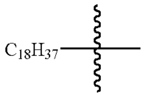
-continued
C15
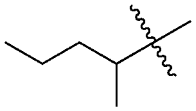
C16
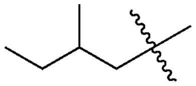
C17
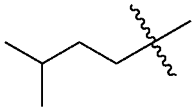
C18
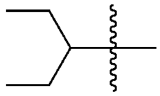
C19
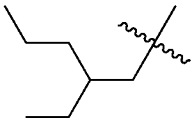
C20
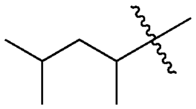
C21
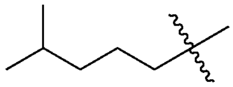
C22
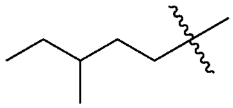
C23
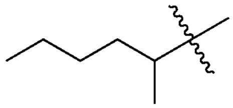
C24
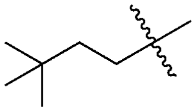
C25
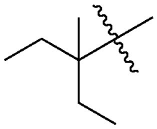
C26
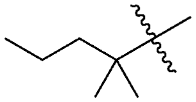
C27
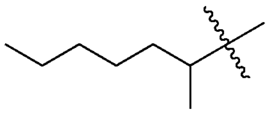

-continued
C28
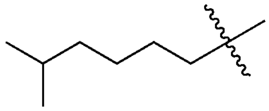
C29
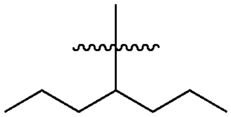
C30
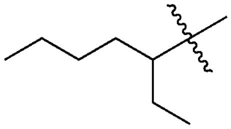
C31
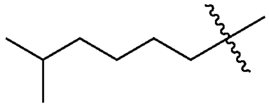
C32
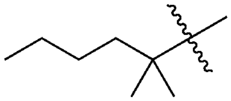
C33
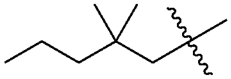
C34
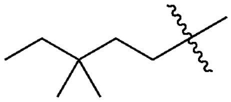
C35
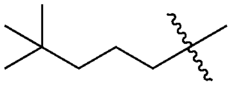
C36
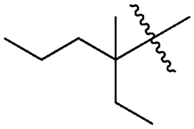
C37
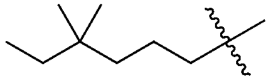
C38
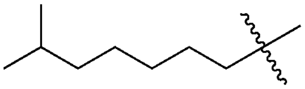
C39
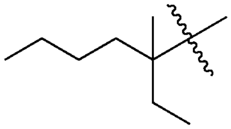
C40
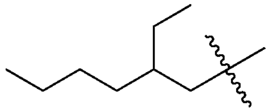
-continued
C41
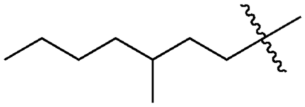
C42
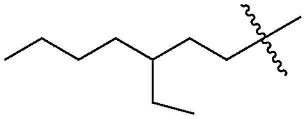
C43
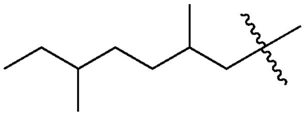
C44
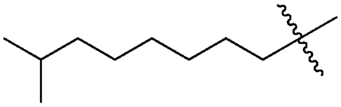
C45
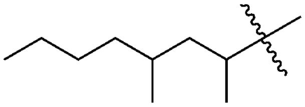
C46
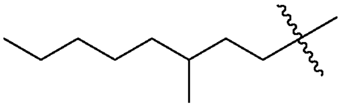
C47
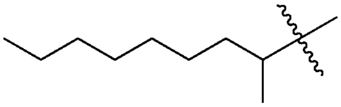
C48
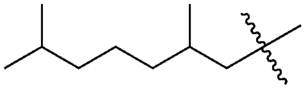
C49
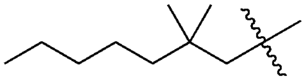
C50
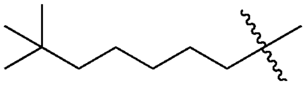
C51
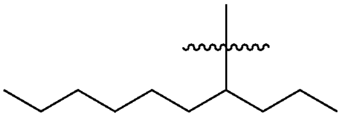
C52
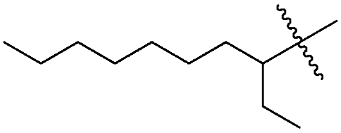
C53
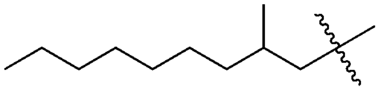

-continued
C54
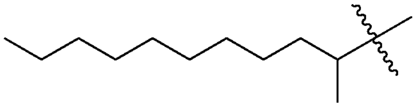
C55
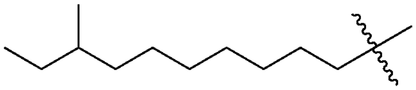
C56
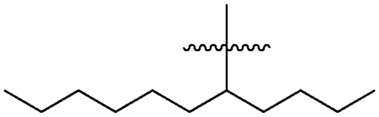
C57
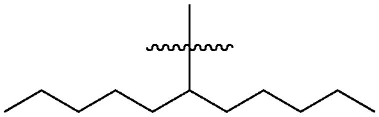
C58
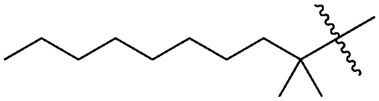
C59
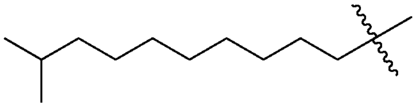
C60
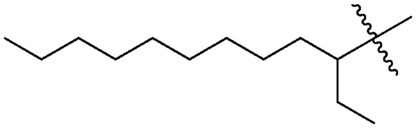
C61
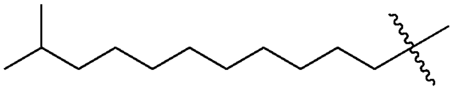
C62
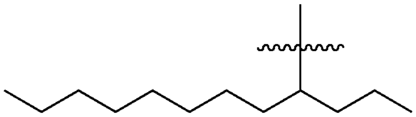
C63
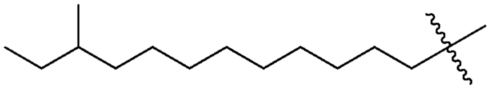
C64
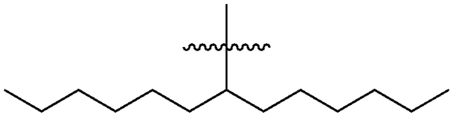
C65
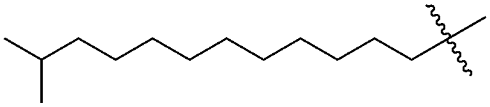
C66
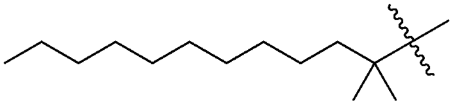
-continued
C67
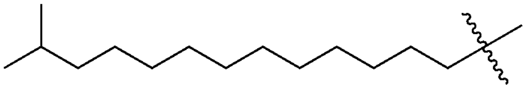
C68
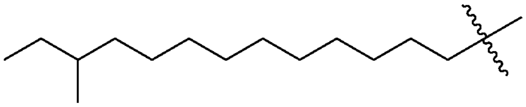
C69
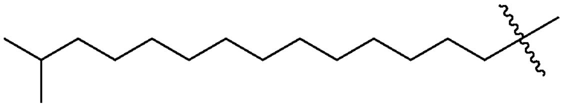
C70
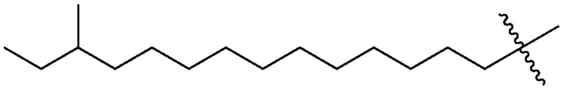
C71
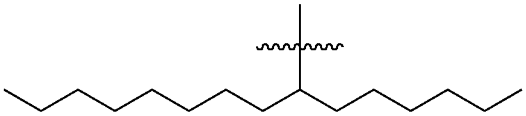
C72
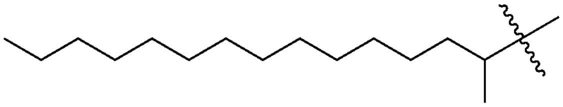
C73
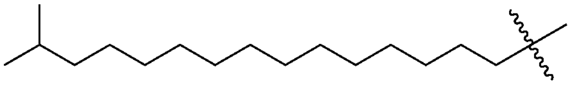
C74
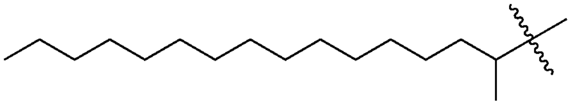
C75
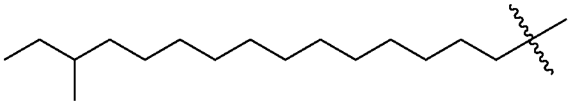
C76
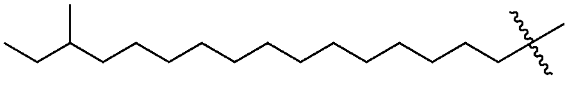
C77
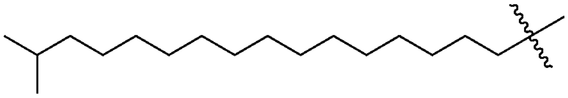

-continued
C78
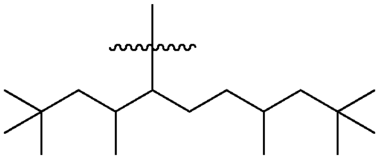
C78
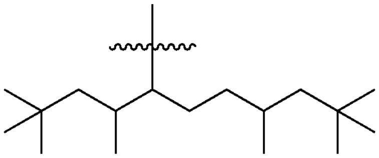
C79
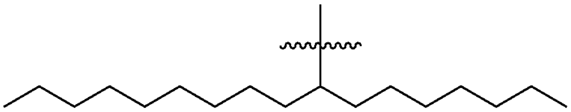
C80
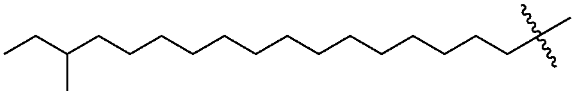
C81
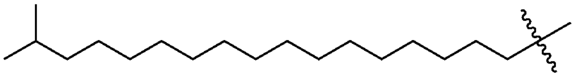
C82
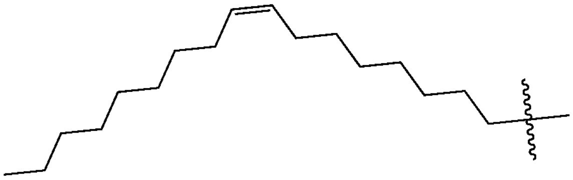
C83
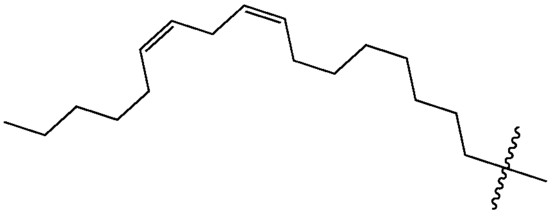
C84
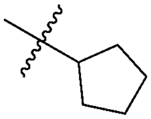
C85
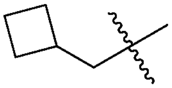
C86
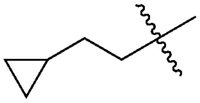
-continued
C87
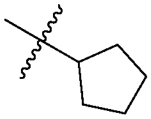
C88
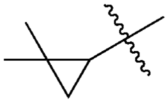
C89
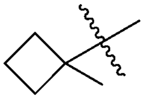
C89
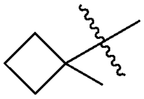
C90
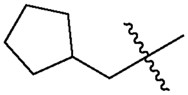
C91
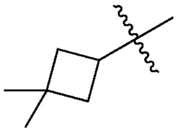
C92
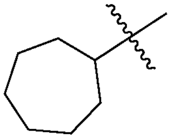
C93
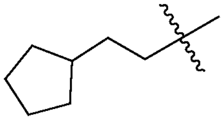
C94
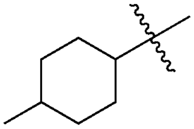
C95
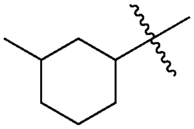
C96
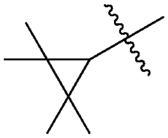
C97
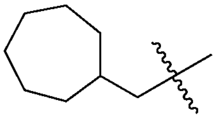

-continued
C98
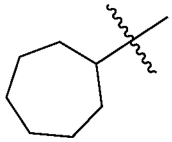
C99
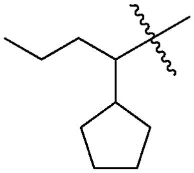
C100
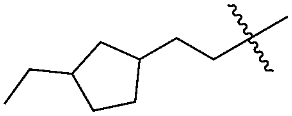
C101
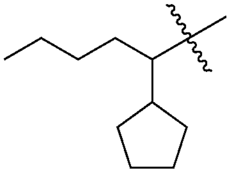
C102
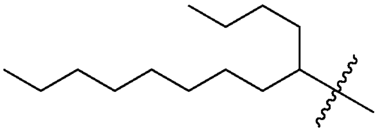
C103
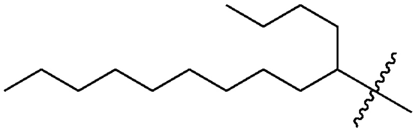
C104
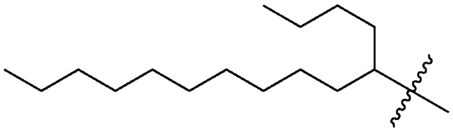
C105
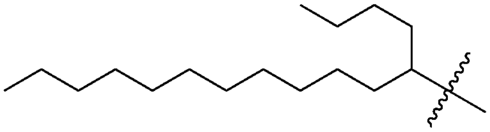
C106
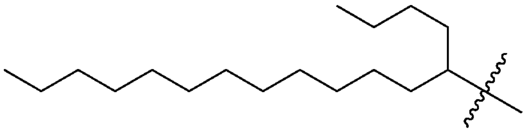
-continued
C107
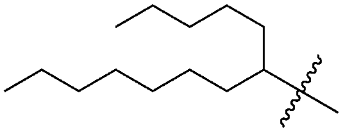
C108
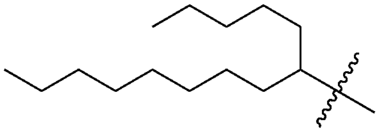
C109
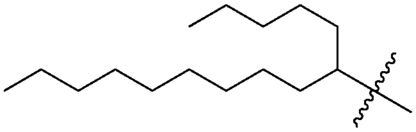
C110
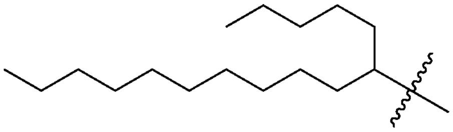
C111
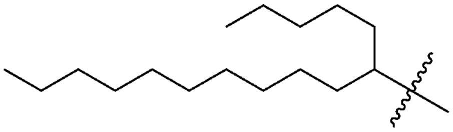
C112
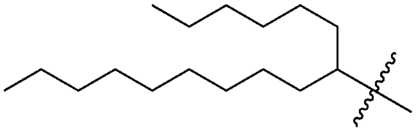
C113
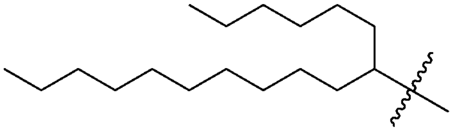
C114
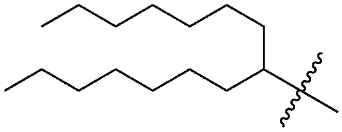
C115
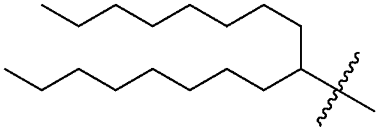
C116
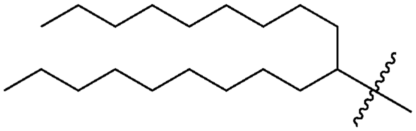
C117
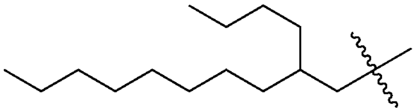

-continued
C118
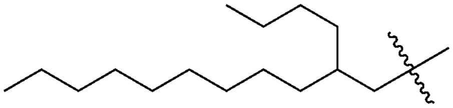
C119
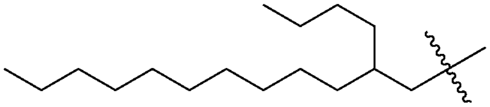
C120
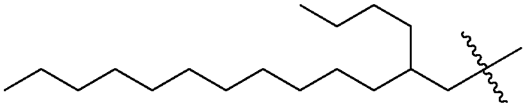
C121
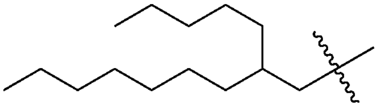
C122
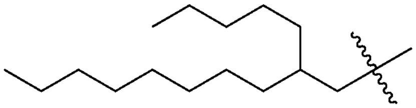
C123
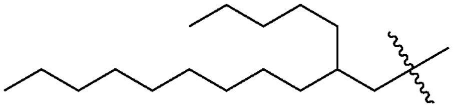
C124
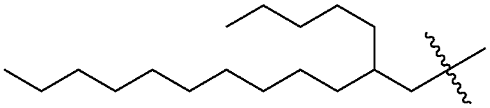
C125
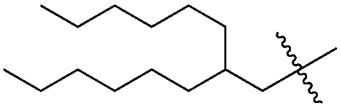
C126
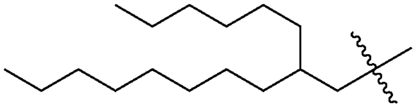
C127
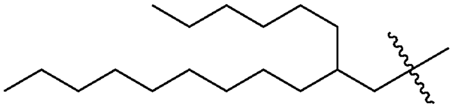
C128
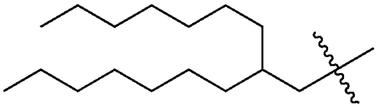
C129
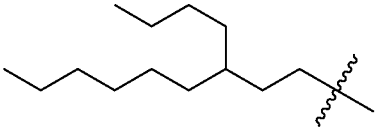
-continued
C130
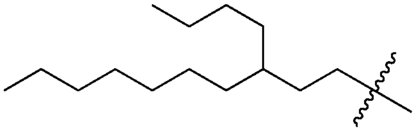
131
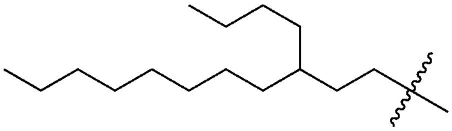
132
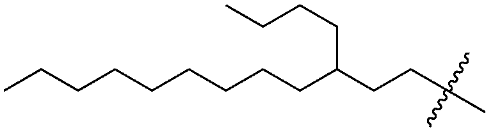
133
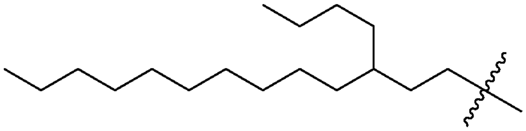
C134
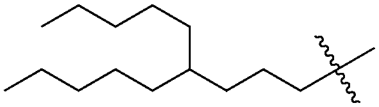
C135
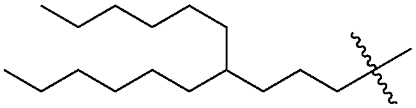
C136
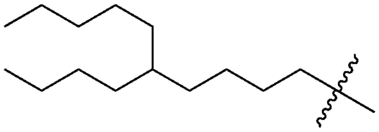
C137
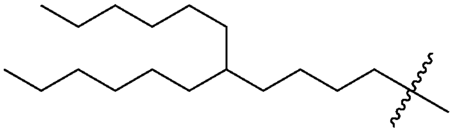
C138
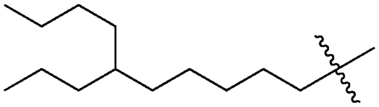
C139
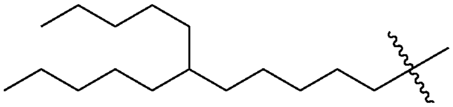
C140
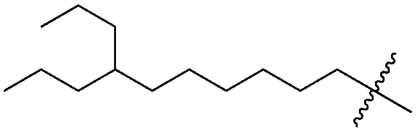

-continued

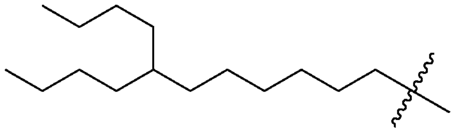
C141

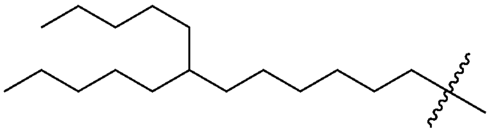
C142

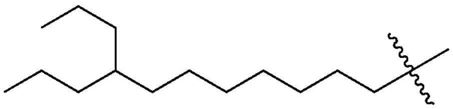
C143

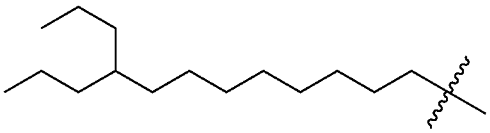
C144

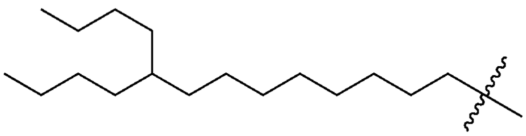
C145

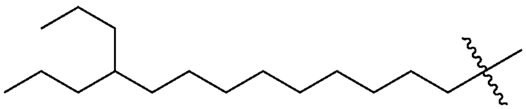
C146

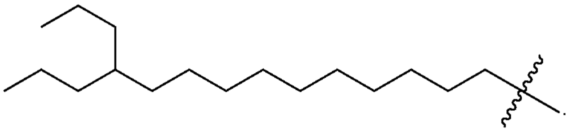
C147

More preferably, the $R^2$ is one selected from C3, C4, C5, C6, C7, C8, C9, C10, C11, C12, C13, C14, C56, C57, C58, C60, C62, C63, C64, C66, C67, C71, C72, C74, C79, C82, C83, C102, C103, C104, C105, C106, C107, C108, C109, C110, C111, C112, C113, C114, C115, C116, C117, C118, C119, C120, C121, C122, C123, C124, C125, C126, C127, C128, C129, C130, C131, C132, C133, C134, C135, C136, C137, C138, C139, C140, C141, C142, C143, C144, C145, C146, C147.

Preferably, $R^3$, $R^4$ and L form an $R^3R^4$—N-L amine-containing carboxylic acid structure of

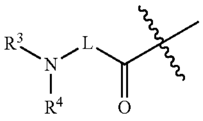
;

and/or $R^3$ and $R^4$ are connected to form a 4 to 10-membered heterocyclic ring, the multi-membered heterocyclic ring includes 1 to 6 heteroatoms, and the heteroatoms are selected from N, S or O.

Preferably,

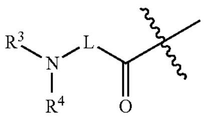

is one selected from A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40:

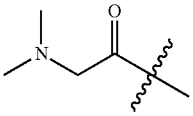
A1

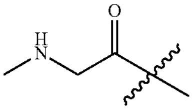
A2

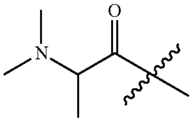
A3

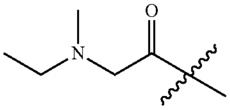
A4

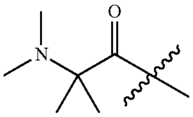
A5

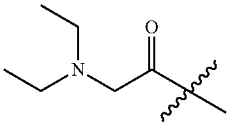
A6

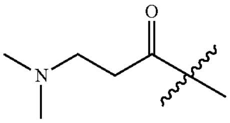
A7

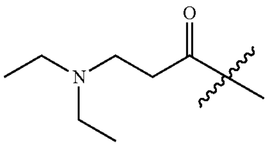
A8

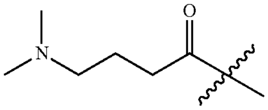
A9

-continued
A10
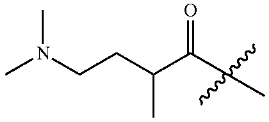
A11
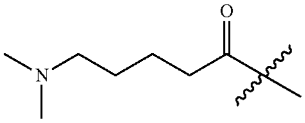
A12
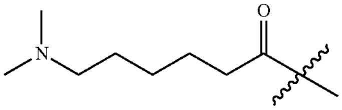
A13
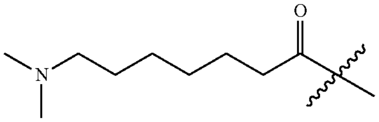
A14
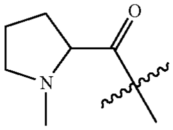
A15
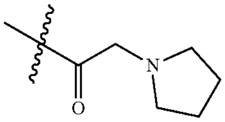
A16
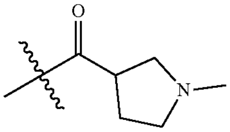
A17
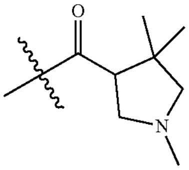
A18
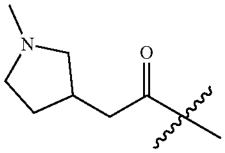
A19
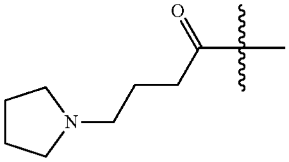
A20
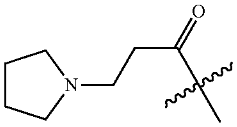
-continued
A21
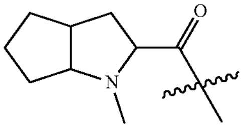
A22
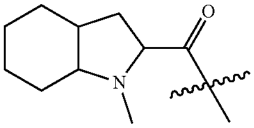
A23
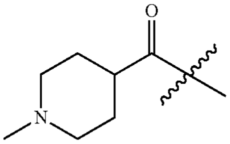
A24
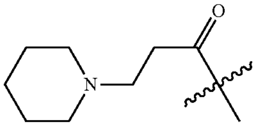
A25
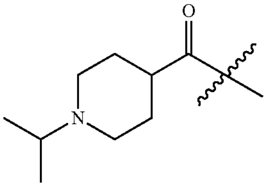
A26
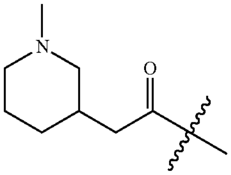
A27
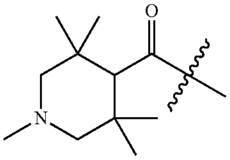
A28
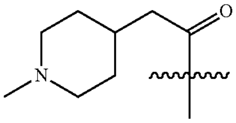
A29
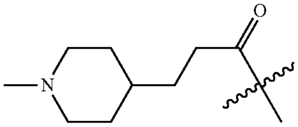
A30
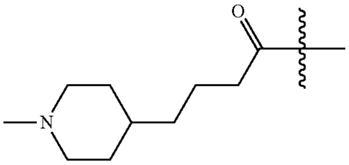

-continued
A31
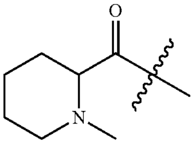
A32
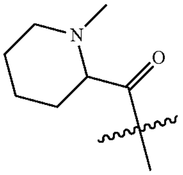
A33
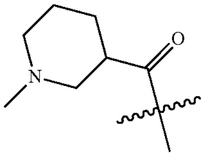
A34
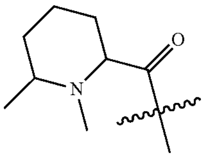
A35
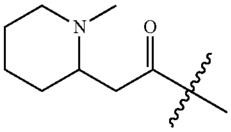
A36
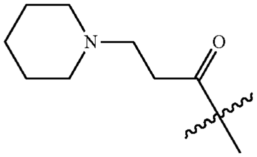
A37
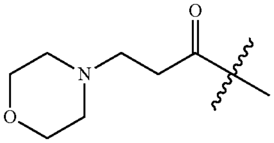
A38
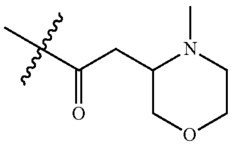
A39
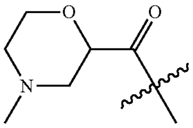
A40
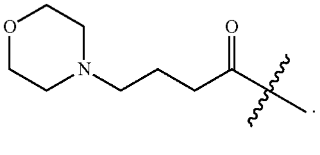
More preferably,
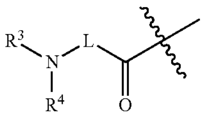
is one selected from A1, A7, A8, A9, A10, A11, A12, A13, A14, A15, A16, A23, A24, A28, A33 and A37:
A1
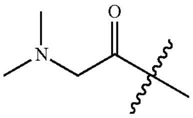
A7
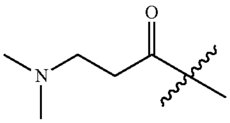
A8
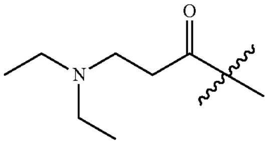
A9
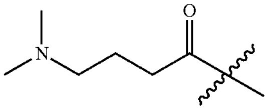
A10
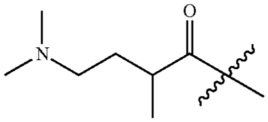
A11
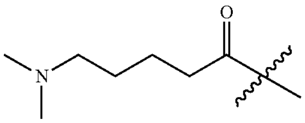
A12
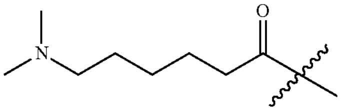
A13
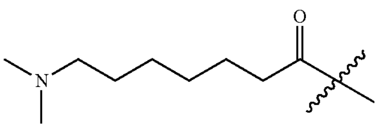
A14
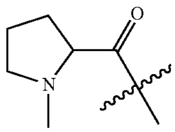
A15
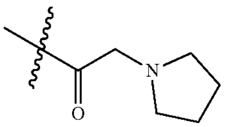

-continued
A16
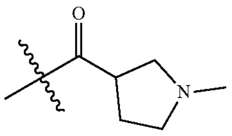
A23
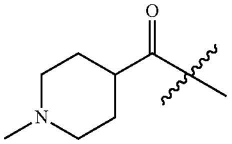
A24
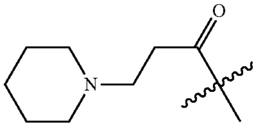
-continued
A28
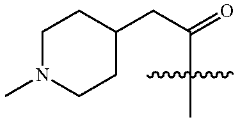
A33
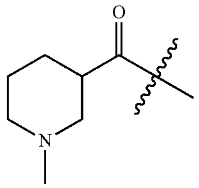
A37
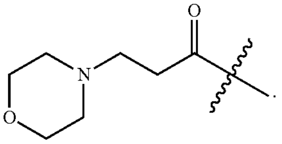
Preferably, the amino lipid is one selected from compounds as shown by the following structures:
E3C79A11
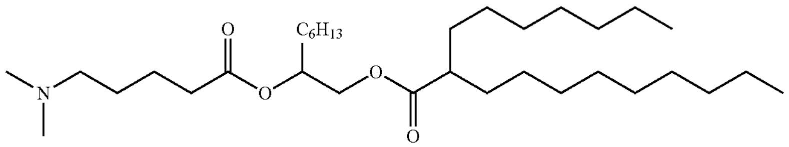
E4C79A9
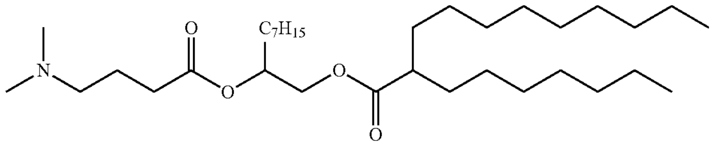
E5C71A11
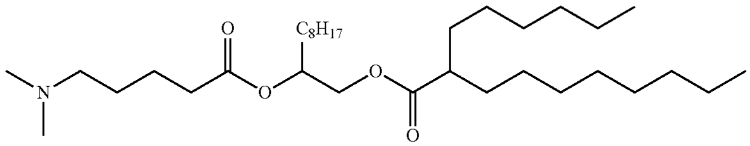
E5C79A11
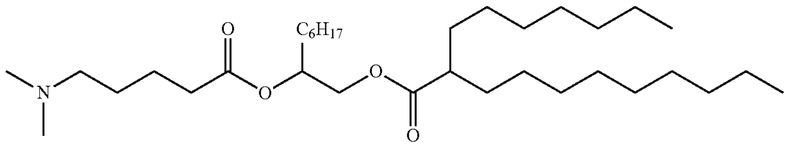
E5C82A23
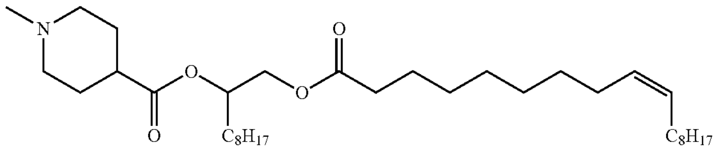
E6C71A11
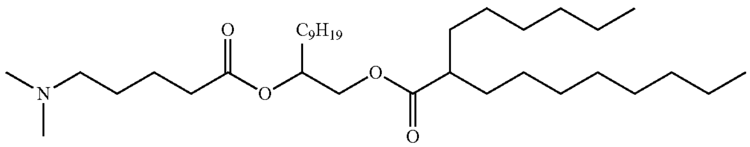

-continued
E6C71A12
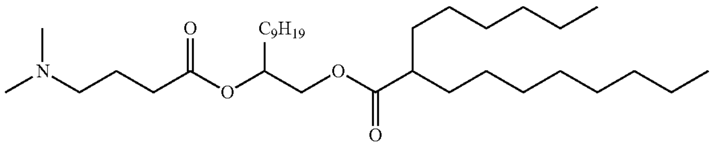
E6C79A12
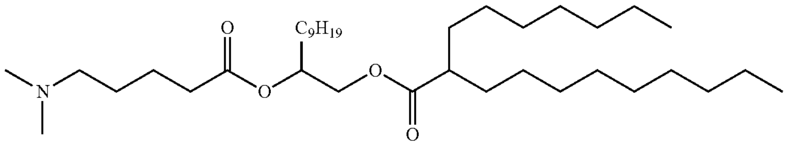
E7C71A9
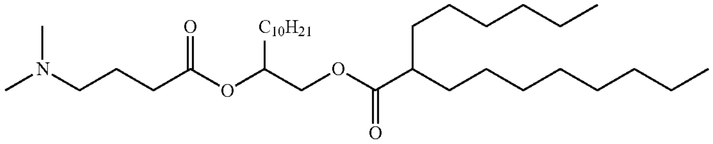
E7C71A11
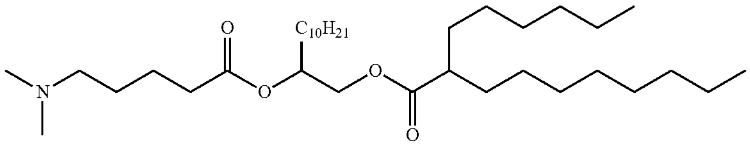
E7C79A9
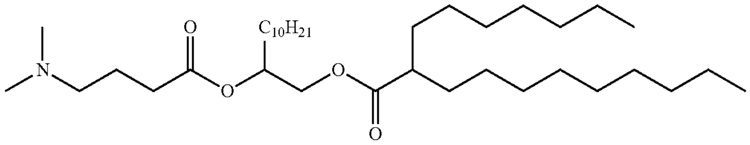
E7C79A11
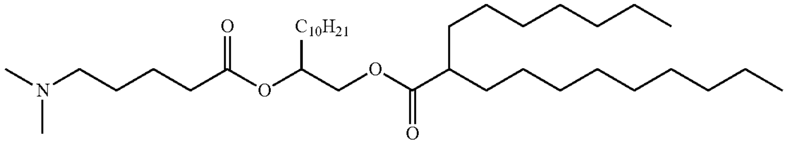
E8C71A9
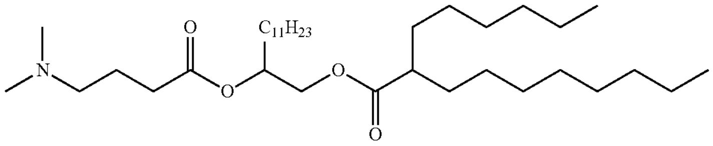
E8C71A23
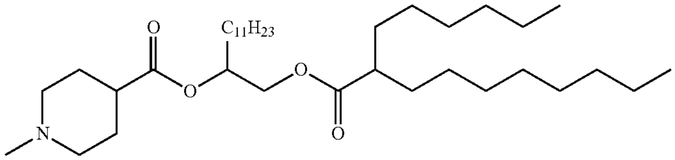
E9C64A9
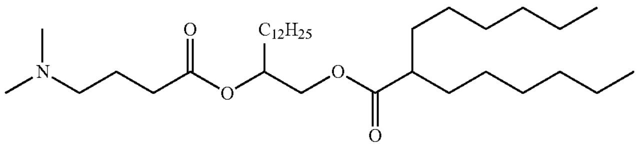

-continued
E21C71A23
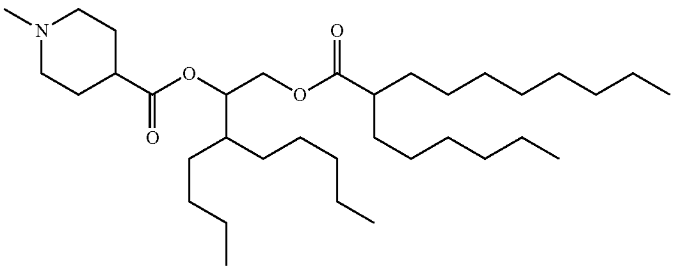
E3C116A9
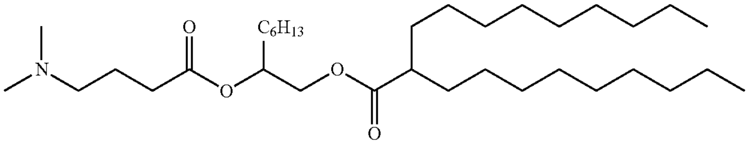
E3C116A11
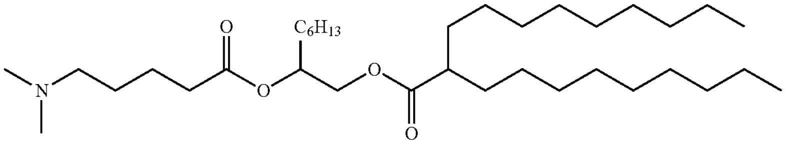
E5C114A9
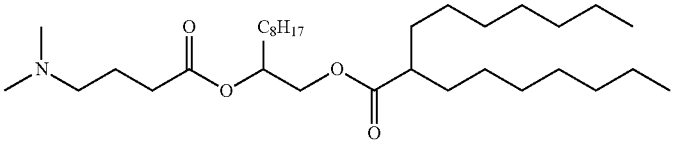
E5C115A9
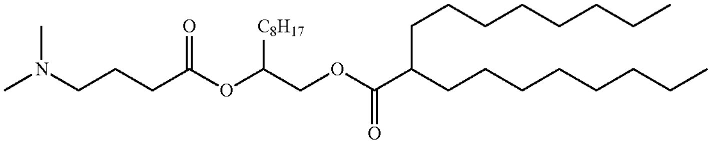
E5C116A9
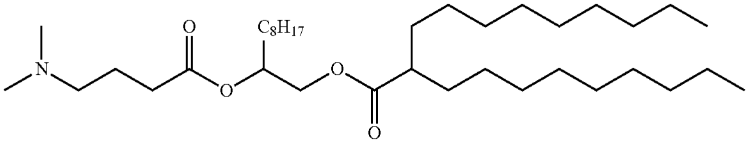
E5C114A11
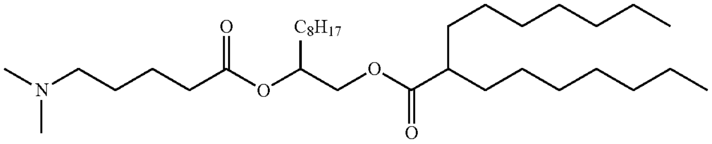
E5C115A11
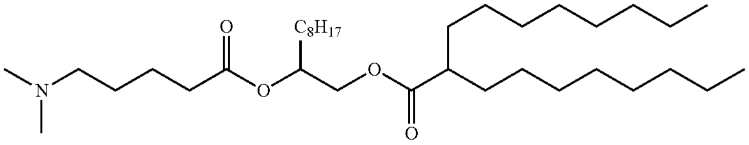
E5C116A11
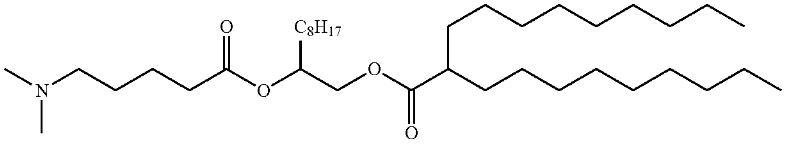

-continued
E7C114A9
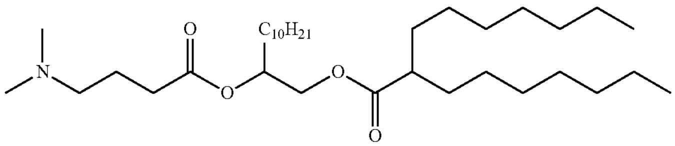
E7C115A9
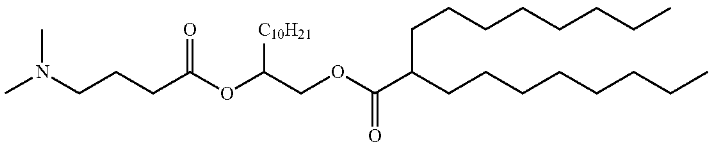
E7C116A9
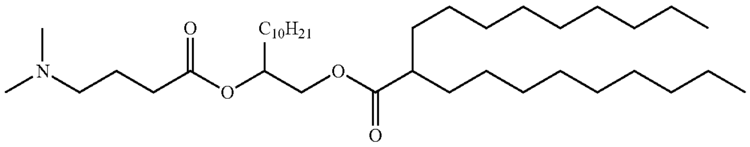
E7C114A11
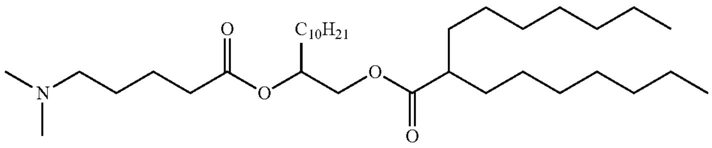
E7C115A11
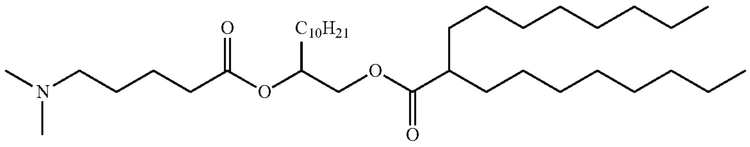
E7C116A11
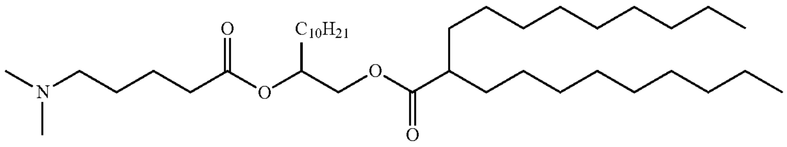
E8C114A9
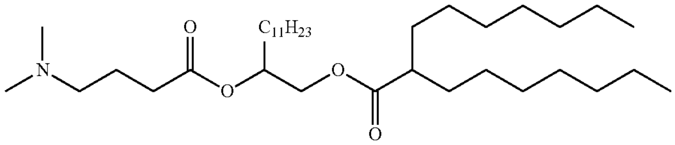
E8C115A11
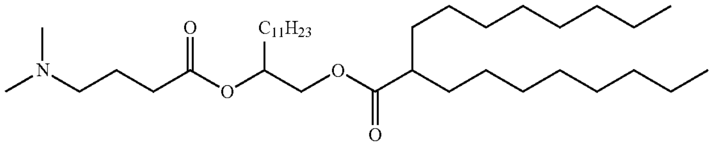
E8C116A9
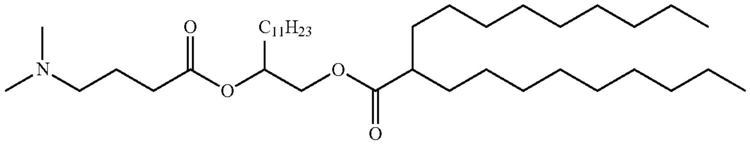
E8C114A11
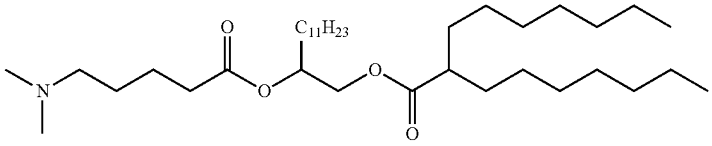

-continued
E8C115A11
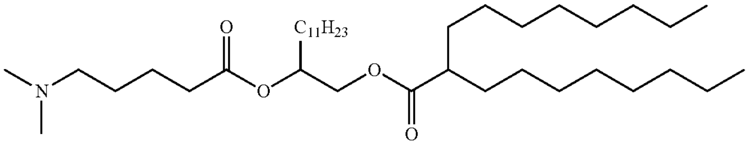
E8C116A11
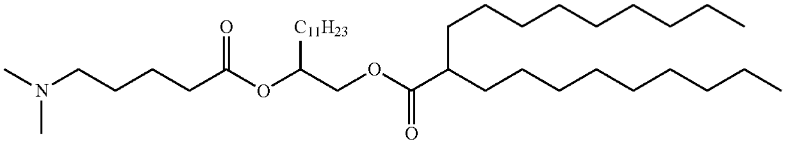
E9C114A9
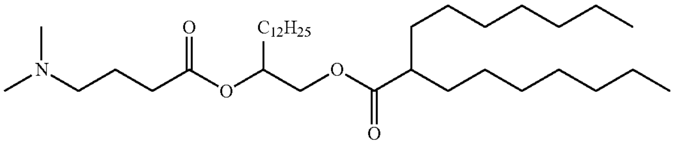
E9C115A9
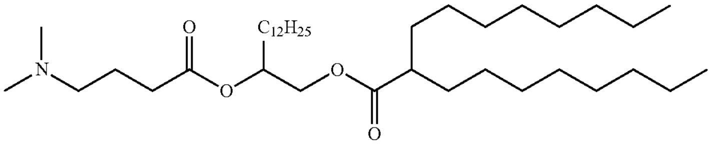
E9C116A9
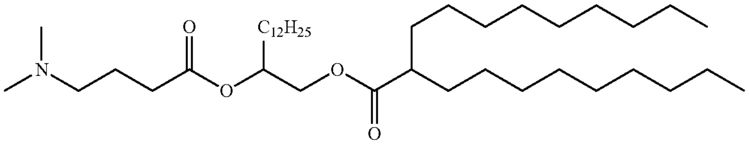
E9C114A11
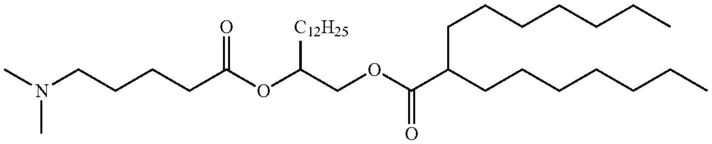
E9C115A11
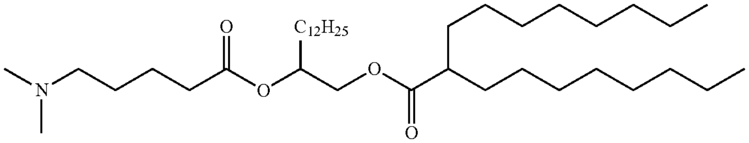
E9C116A11
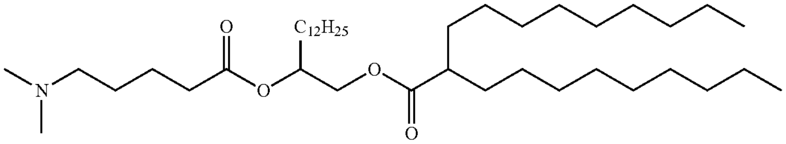
E10C114A9
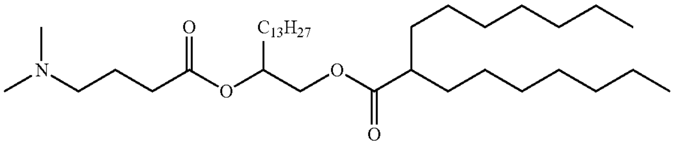
E10C115A9
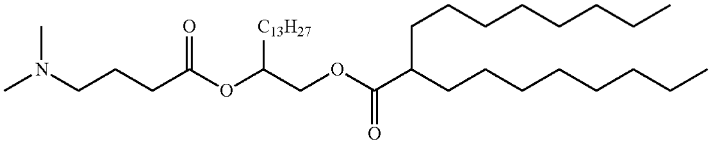

-continued
E10C114A11
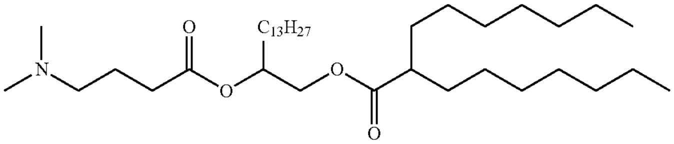
E10C115A11
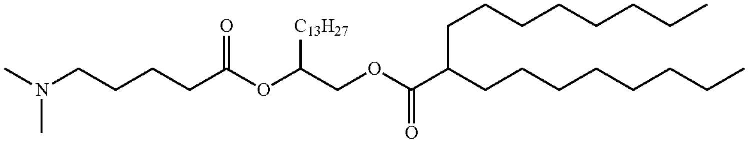
E11C114A9
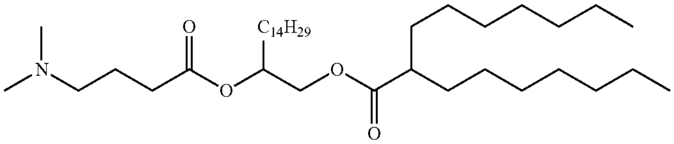
E11C115A9
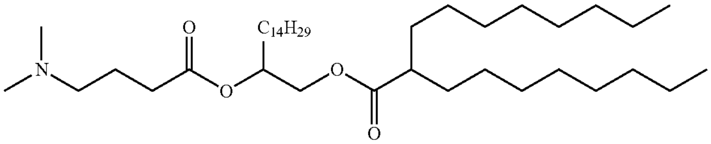
E11C114A11
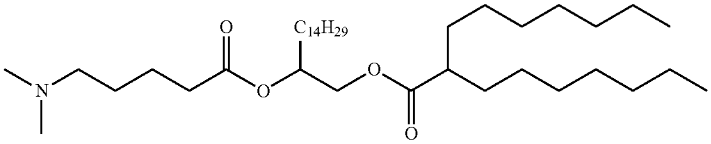
E11C115A11
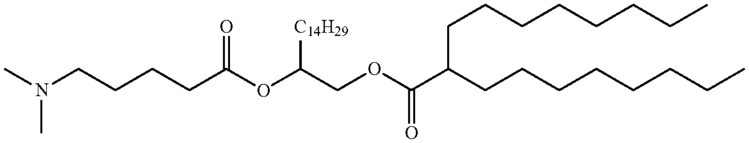
E8C64A12
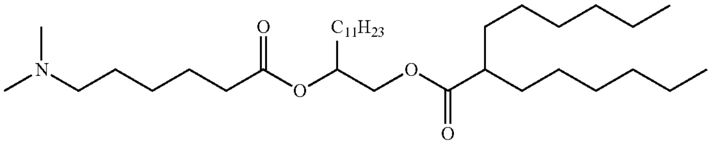
E10C64A12
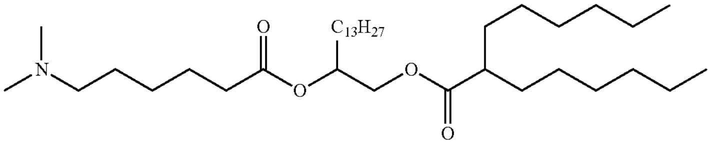
E11C64A12
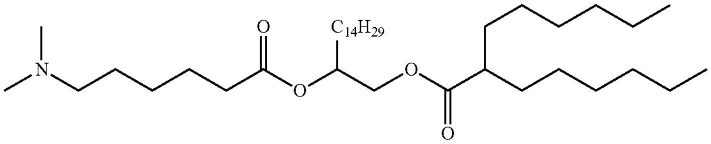
E7C71A12
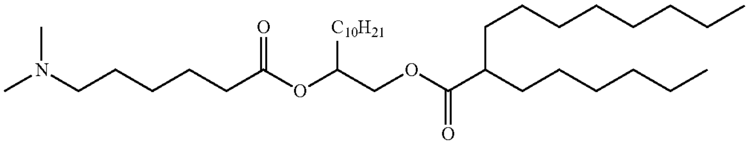

-continued
E8C71A12
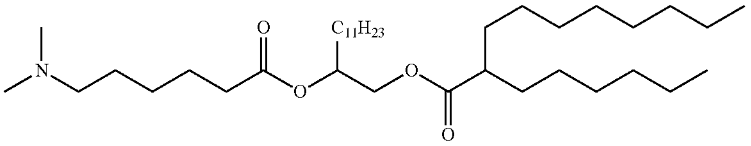
E9C71A12
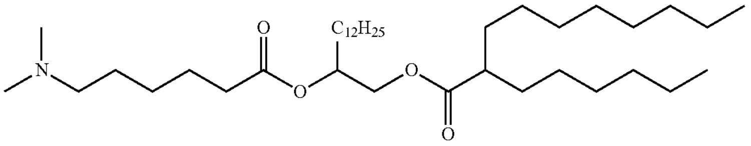
E10C71A12
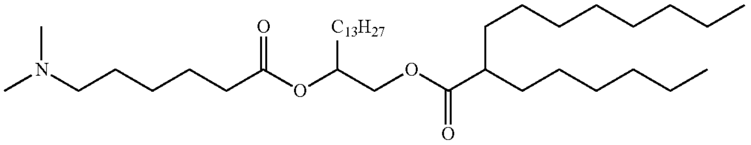
E11C71A12
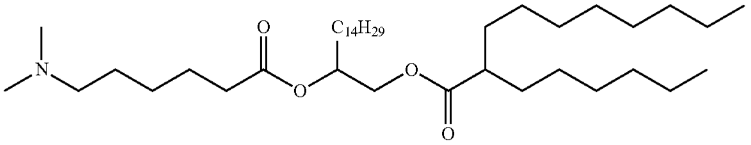
E7C114A12
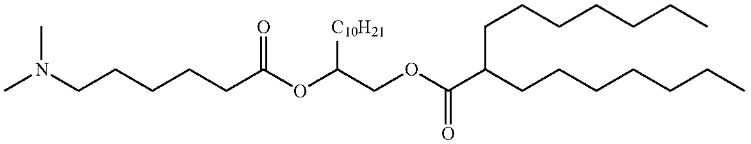
E8C114A12
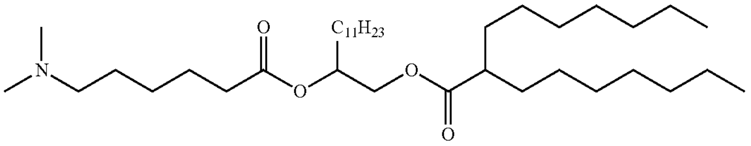
E9C114A12
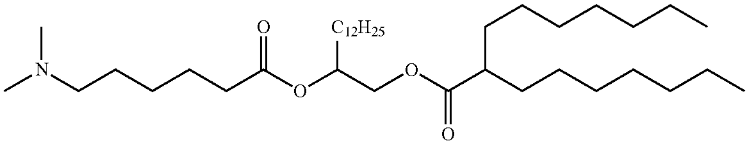
E10C114A12
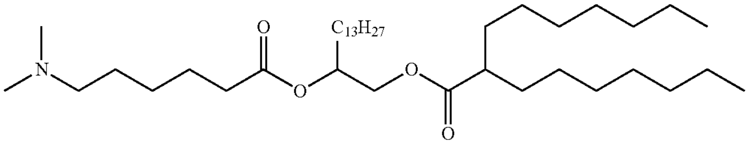
E11C114A12
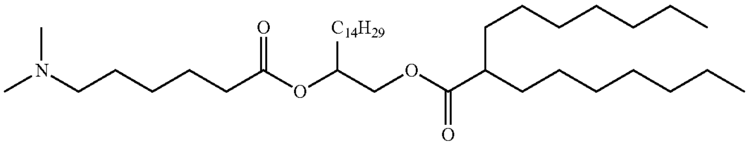
E7C115A12
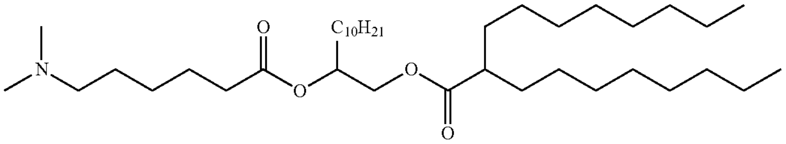

-continued
E8C115A12
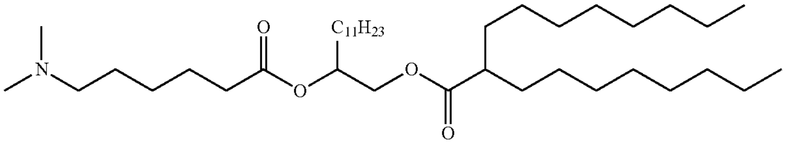
E9C115A12
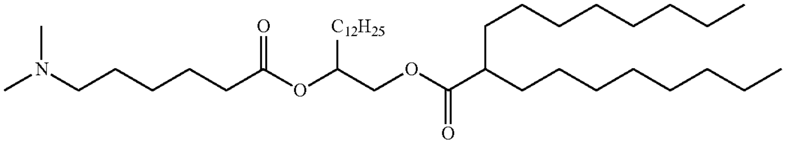
E10C115A12
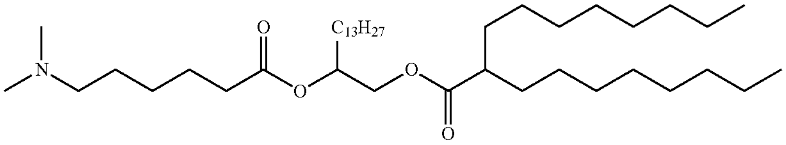
E11C115A12
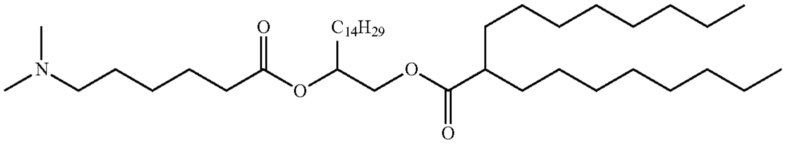
E7C116A12
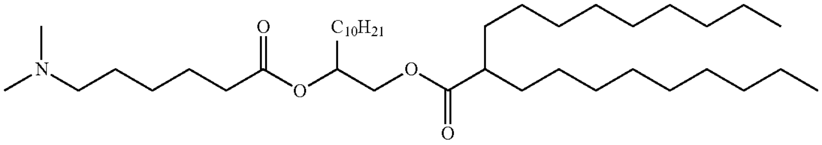
E8C116A12
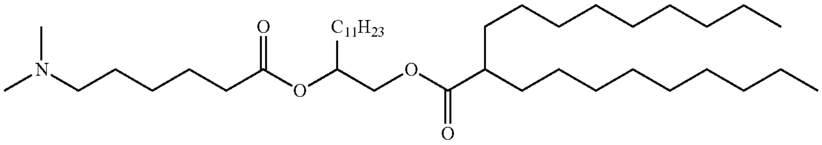
E9C116A12
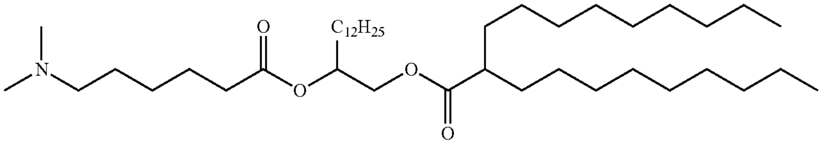
E10C116A12
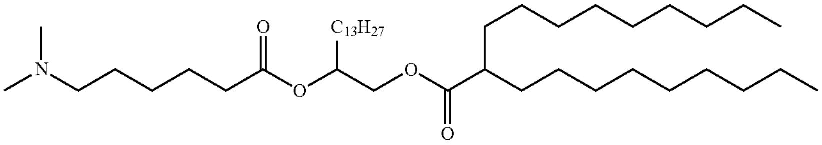
E11C116A12
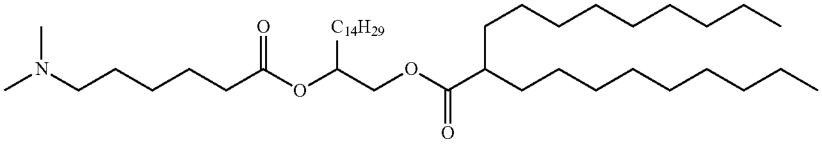
E9C126A12
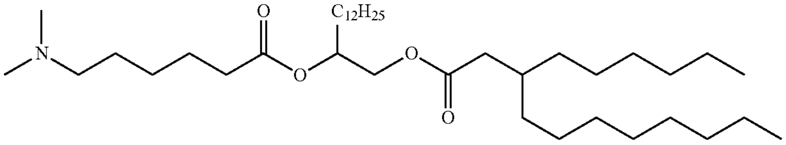

-continued
E7C128A12
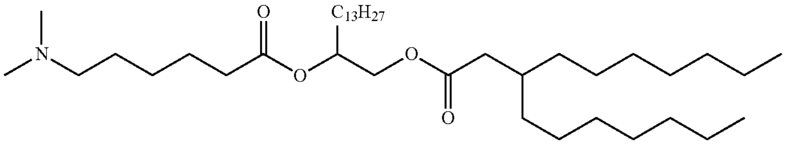
E9C128A12
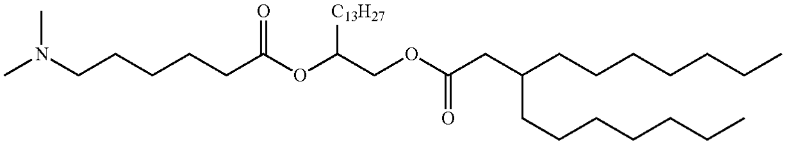
E11C128A12
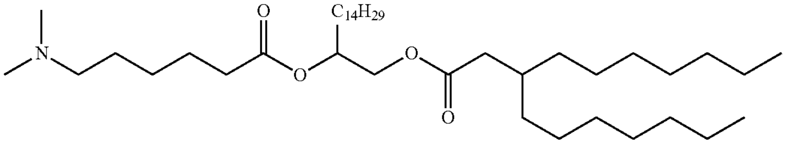
E9C134A12
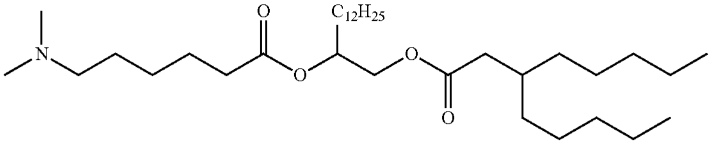
E11C134A12
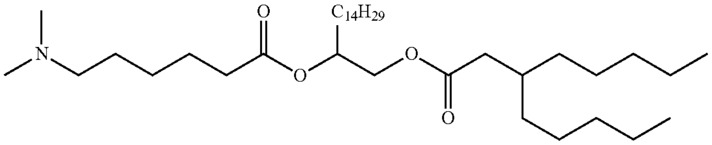
E10C135A12
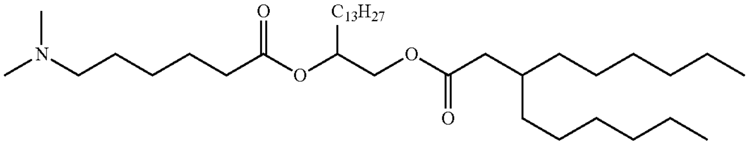
E11C135A12
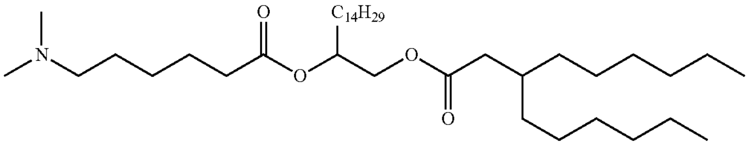
E7C137A12
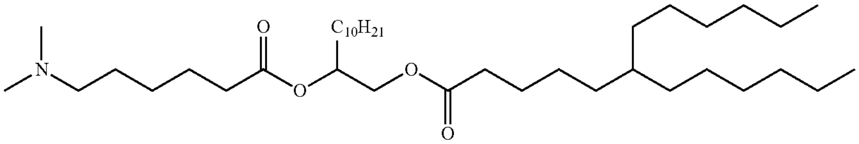
E9C137A12
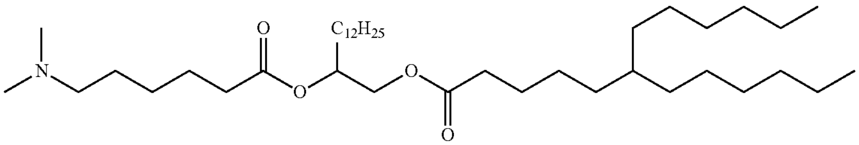
E7C139A12
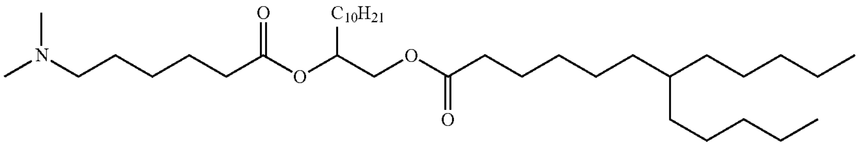

-continued
E7C71A13
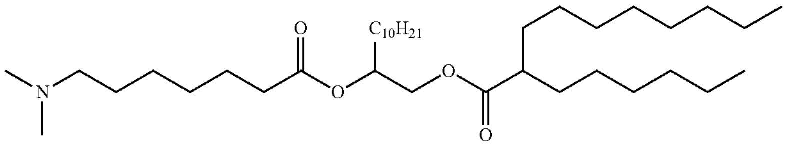
E8C71A13
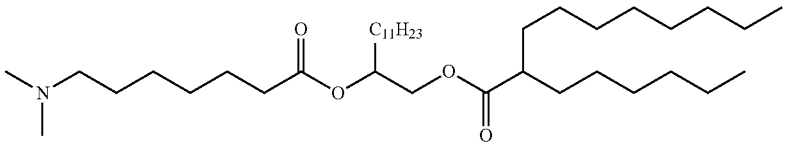
E9C71A13
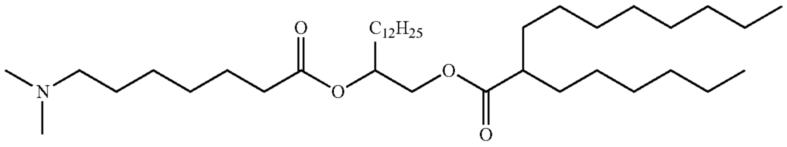
E10C71A13
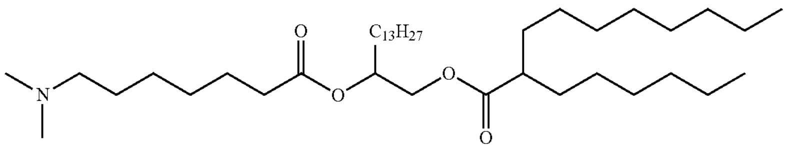
E11C71A13
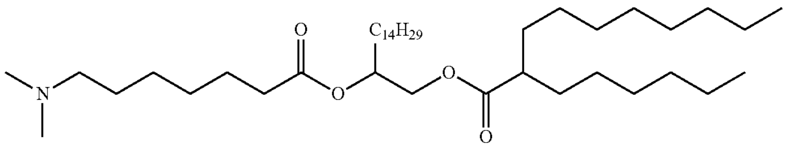
E7C115A13
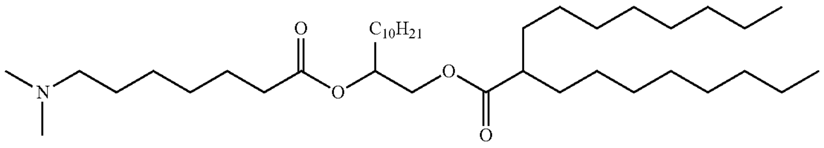
E7C116A13
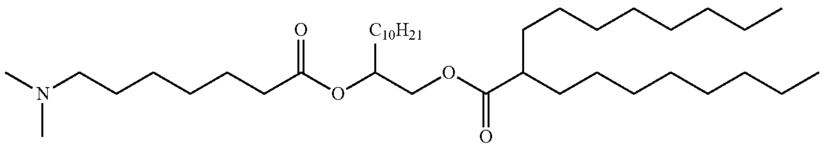
E9C114A13
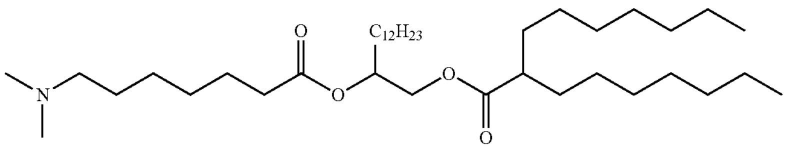

In a second aspect, the disclosure provides:

a preparation method of the amino lipid according to the first aspect of the disclosure, including the following steps:

S1: taking a solvent-free reaction on a compound of $R^2COOH$ and an epoxide compound under the catalysis of $FeCl_3$/Py;

S2: adding $R^3R^4NLCOOH$ into the reaction system of S1, and taking a reaction under the condition of existence of a condensation agent to obtain the amino lipid.

The reaction process is described as follows:

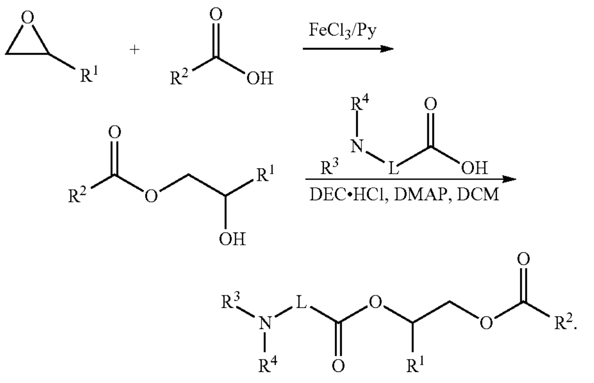

Preferably, the method includes the following steps:

(1) the first intermediate was obtained through the reaction of an epoxide compound with a compound expressed by $R^2COOH$ at room temperature under the catalysis of $FeCl_3$ and Py; and (2) the first intermediate was separated, a catalytic amount of DMAP was added under the effect of a condensation agent so that the first intermediate and COOH of $R^3R^4NLCOOH$ took a second reaction at room temperature to obtain the amino lipid compound as shown in Formula I. The condensation agent used in the preparation method was EDC·HCl, DCC, etc.

In a third aspect, the disclosure provides:

an application of the amino lipid according to the first aspect of the disclosure, and a pharmaceutically acceptable salt, prodrug or stereoisomer of the amino lipid in the preparation of drugs for gene therapy, genetic vaccination, antisense therapy or RNA interference therapy.

Preferably, the drug is used for treating cancer or genetic diseases.

Preferably, the tumor includes but is not limited to gastric cancer, liver cancer, esophagus cancer, colorectal cancer, pancreatic cancer, cerebral cancer, lymph cancer, leukemia, bladder cancer or prostatic cancer. The genetic diseases include but are not limited to hemophilia, thalassemia or Gaucher diseases.

Preferably, the drug is used for treating cancer, allergy, toxicity and pathogen infection.

Preferably, the application is the application for preparation of nucleic acid transfer drugs.

Preferably, the nucleic acid is RNA, including but not limited to mRNA, antisense oligonucleotide, DNA, plasmid, rRNA, miRNA, RNA, siRNA and snRNA.

In a fourth aspect, the disclosure provides:

a nanoparticle delivery system having a raw material of the amino lipid according to the first aspect of the disclosure.

Compared with the prior art, the disclosure has the following technical effects:

The ionizable amino lipid as shown in Formula (I)

(I)

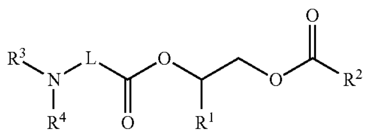

disclosed by the disclosure or the pharmaceutically acceptable salt thereof achieves mild reaction conditions in an amino lipid construction process, does not need protection or deprotection, and realizes high atom economy. In in-vitro and in-vivo delivery study, the excellent capability of delivering the nucleic acid to cells is shown. The amino lipid compound has two ester bonds. Due to the introduction of the ester group, the degradation ability of cationic polymers is obviously enhanced, the cell toxicity is greatly reduced, meanwhile, the release of delivery targets such as target drugs or genes can be facilitated, and the delivery efficiency is further improved. The preparation method of the amino lipid compound has the advantages of easy acquisition of raw materials, mild reaction conditions, good reaction selectivity, high reaction yield, low instrument equipment requirement and simple operation.

DETAILED DESCRIPTION

Figure 1:
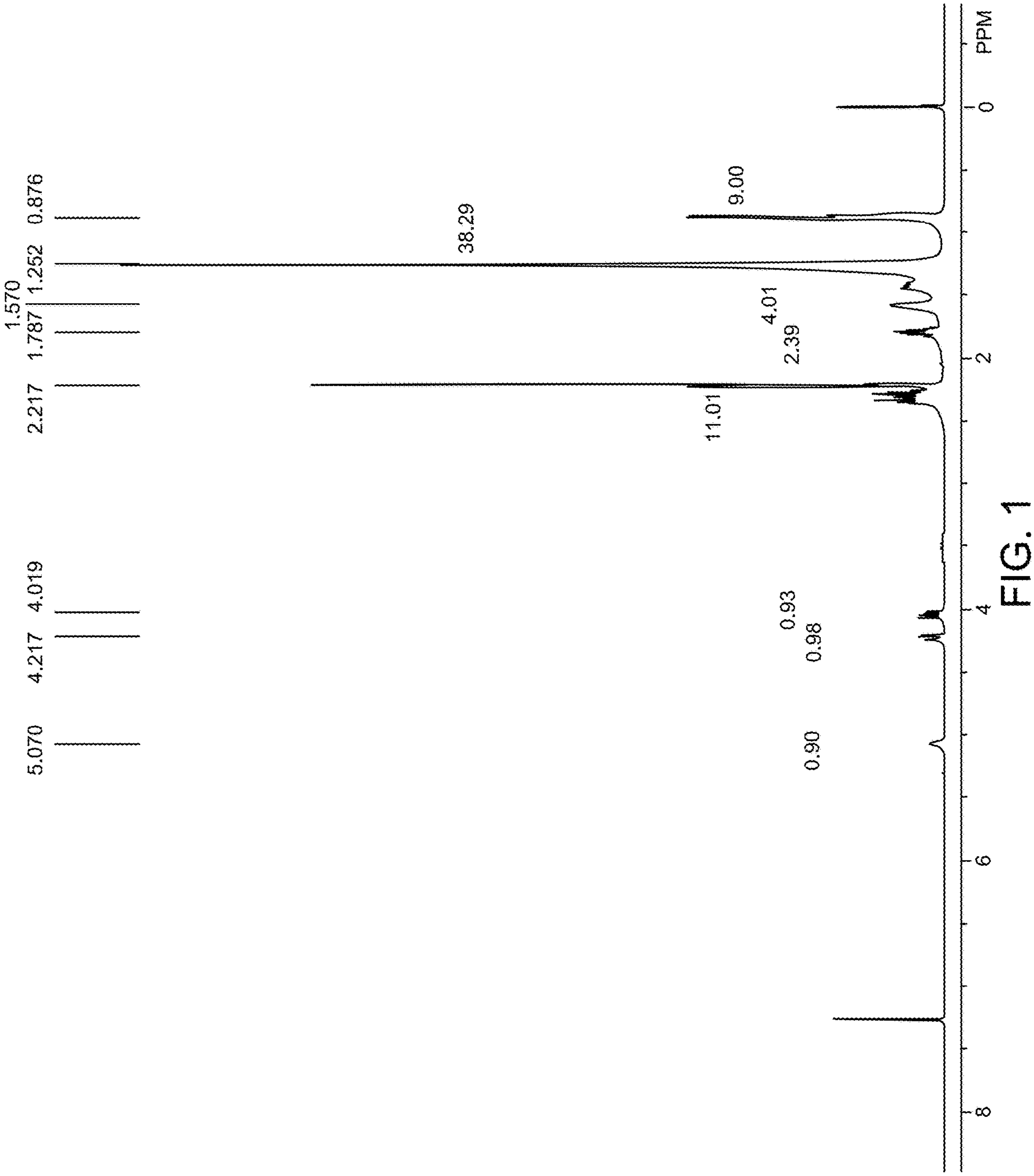
FIG. 1 is a $^1$H-NMR spectrum of E7C71A9 in Embodiment 5.

Specific implementations of the disclosure are further described below. It needs to be noted that the description of these implementations provided is intended to help to understand the disclosure, but not intended to limit the scope of the disclosure. Furthermore, the technical features involved in the various implementations of the disclosure described below can be combined with each other as long as they do not conflict with each other.

Test methods used in following experimental examples are all conventional methods unless otherwise specified. Used materials, reagents, etc. are commercially available materials and reagents unless otherwise specified.

The term “optionally substituted”, as used herein, means that one or more hydrogen atoms attached to an atom or group is independently unsubstituted or substituted by one or more, for example, one, two, three or four, substituents. When an atom or group is substituted by a plurality of substituents, the plurality of substituents may be identical or different.

Abbreviations Herein:

| | |
|---|---|
| RNA | Ribonucleic acid |
| DSPC | Distearoyl phosphatidyl choline |
| DOPE | Dioleoyl phosphatidyl ethanolamine |
| DOPC | Dioleoyl phosphatidyl choline |
| DOPS | Dioleoyl phosphatidyl serine |
| DSPE | Distearoyl phosphatidyl ethanolamine |
| PEG2000-DMG | (1-(monomethoxypolyethylene glycol)-2,3 dimyristoyl-glycerol |
| kD | Kilodalton |
| PBS | Phosphate buffer solution |

In the following embodiments, a general structure formula of the amino lipid is shown in Formula (I)

(I)

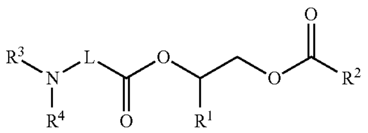

unless otherwise specified. For the amino lipid structures represented by serial numbers, E1-E25 are the above defined $R^1$ substituents, C1-C147 are the above defined $R^2$ substituents, and A1-A40 are the above defined

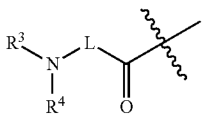

groups. For example, the structure formula of E7C71A1 is

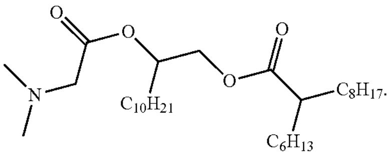

Embodiment 1: Parallel Synthesis and Characterization of E7C71Ay Series Amino Lipid Compound Library

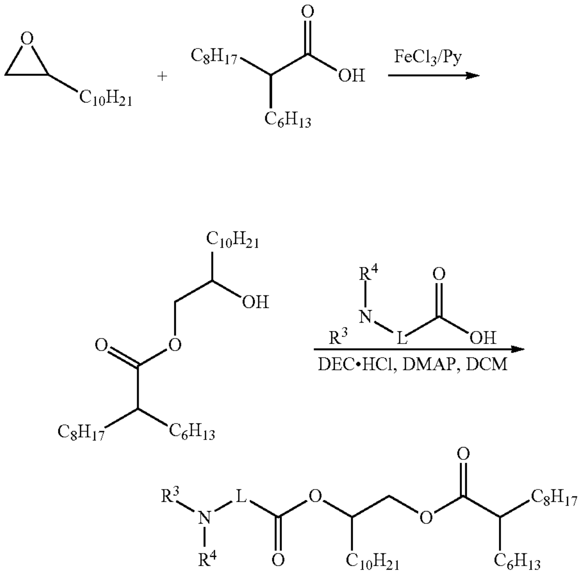

$FeCl_3$ (4 mg, 0.005 mmol), Py (1 μL, 0.0025 mmol), 2-hexyldecanoic acid (0.3 mL, 1 mmol) and 1,2-cyclododecane epoxide (0.27 mL, 1.2 mmol) were sequentially added into a 25 mL reaction tube, and then the reaction was stirred at room temperature overnight to obtain Step I (1 mmol). 10 mL of DCM was added to prepare 0.1 M of a Step I solution.

The Step I solution was respectively transferred into a 1.5 mL 96-well plate (0.1 mL for each, 0.01 mmol) by a pipette, a DCM solution (0.1 mL, 0.02 mmol, 0.2 M) of tertiary amine group-containing carboxylic acid, DIPEA, a DCM solution (0.2 mL, 0.04 mmol, 0.2 M) of EDC·HCl and a DCM solution (0.1 mL, 0.005 mmol, 0.05 M) of DMAP were respectively added into each well, then the mixture was stirred for 6 h at room temperature, and no Step I raw material was observed by TLC detection. After the reactions were completed, the solution was volatilized at room temperature to dryness, and 15 amino lipid compounds E7C71Ay were obtained. Mass spectrometric detection was performed, and the results were collected as shown in Table 1.

TABLE 1

MW/z value of E7C71Ay series amino lipid compound library

| Serial number of compound | Structure | Molecular formula | Molecular weight | Calculated value M | Measured value $(M + H)^+$ |
|---|---|---|---|---|---|
| 1 E7C71A1 | 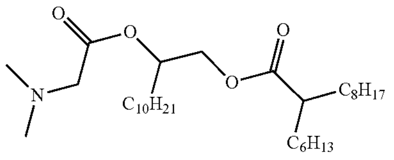 | $C_{32}H_{63}NO_4$ | 525.9 | 525.5 | 526.6 |

TABLE 1-continued
MW/z value of E7C71Ay series amino lipid compound library
| Serial number of compound | | Structure | Molecular formula | Molecular weight | Calculated value M | Measured value $(M + H)^+$ |
|---|---|---|---|---|---|---|
| 2 | E7C71A7 | 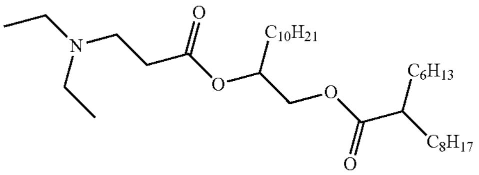 | $C_{35}H_{69}NO_4$ | 567.9 | 567.5 | 568.6 |
| 3 | E7C71A8 | 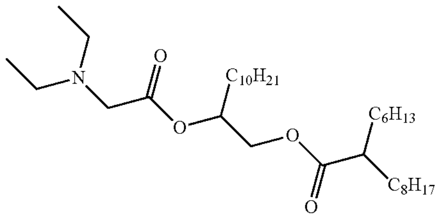 | $C_{34}H_{67}NO_4$ | 553.9 | 553.5 | 554.7 |
| 4 | E7C71A9 | 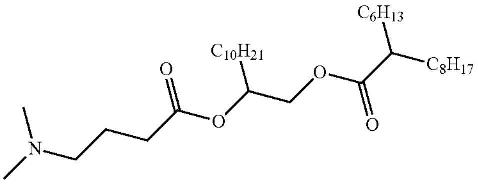 | $C_{34}H_{67}NO_4$ | 553.9 | 553.5 | 554.7 |
| 5 | E7C71A10 | 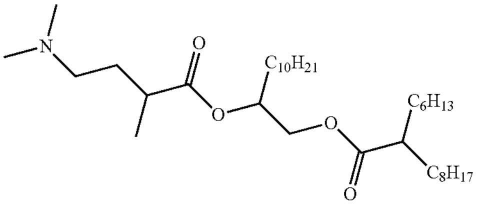 | $C_{35}H_{69}NO_4$ | 567.9 | 567.5 | 568.6 |
| 6 | E7C71A11 | 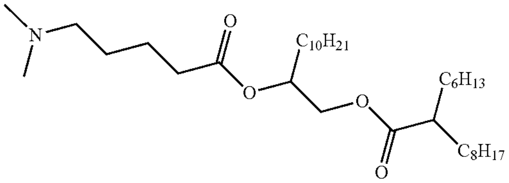 | $C_{35}H_{69}NO_4$ | 567.9 | 567.5 | 568.7 |
| 7 | E7C71A12 | 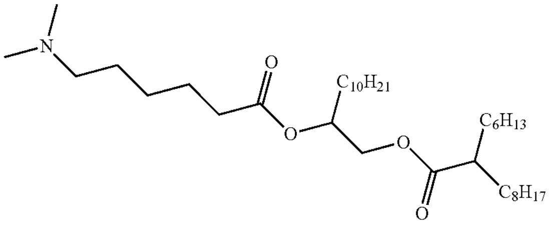 | $C_{36}H_{71}NO_4$ | 582.0 | 581.5 | 582.6 |
| 8 | E7C71A14 | 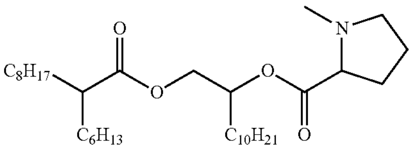 | $C_{34}H_{65}NO_4$ | 551.9 | 551.5 | 552.7 |

TABLE 1-continued
| Serial number of compound | | Structure | Molecular formula | Molecular weight | Calculated value M | Measured value $(M + H)^+$ |
|---|---|---|---|---|---|---|
| 9 | E7C71A15 | 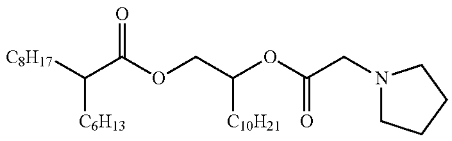 | $C_{34}H_{65}NO_4$ | 551.9 | 551.5 | 552.7 |
| 10 | E7C71A16 | 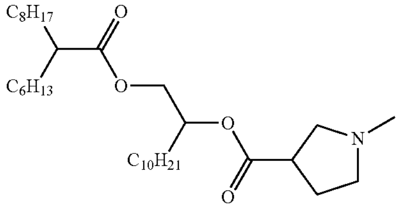 | $C_{34}H_{65}NO_4$ | 551.9 | 551.5 | 552.6 |
| 11 | E7C71A23 | 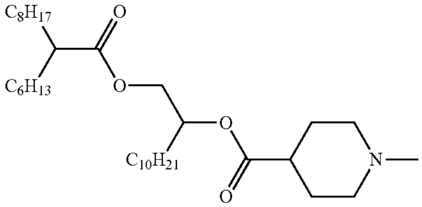 | $C_{35}H_{67}NO_4$ | 565.9 | 565.5 | 566.7 |
| 12 | E7C71A24 | 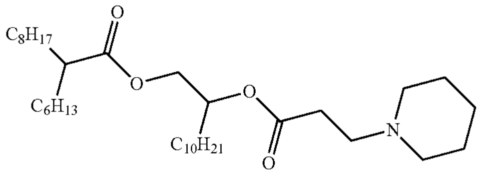 | $C_{36}H_{69}NO_4$ | 580.0 | 579.5 | 580.6 |
| 13 | E7C71A28 | 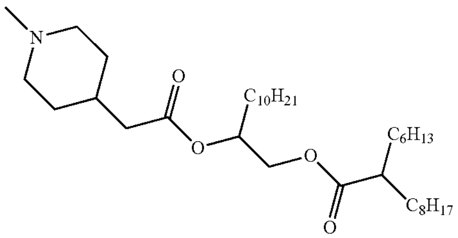 | $C_{36}H_{69}NO_4$ | 580.0 | 579.5 | 580.6 |
| 14 | E7C71A33 | 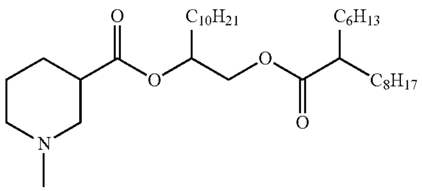 | $C_{35}H_{67}NO_4$ | 565.9 | 565.5 | 566.7 |
| 15 | E7C71A37 | 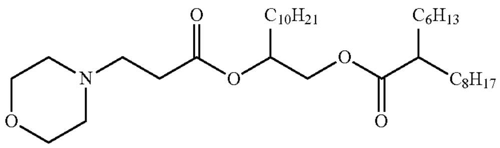 | $C_{35}H_{67}NO_5$ | 581.9 | 581.5 | 582.7 |
MW/z value of E7C71Ay series amino lipid compound library

Embodiment 2:2-Hydroxyhexadecyl Dodecanoate

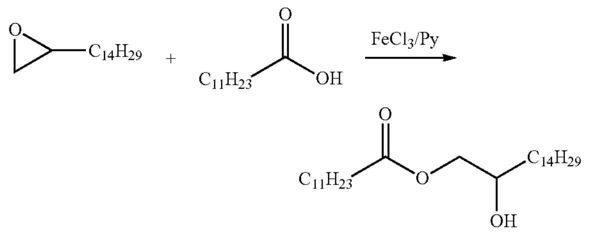

$FeCl_3$ (20 mg, 0.025 mmol), Py (5 μL, 0.0125 mmol), dodecanoic acid (1 g, 5 mmol) and 2-epoxy hexadecane (1.7 mL, 6 mmol) were sequentially added into a 25 mL reaction tube, and then the reaction was stirred at room temperature overnight. Column chromatography gradient elution purification (hexane:EA=20:1 to 5:1) was performed to obtain 2-hydroxyhexadecyl dodecanoate (2.0 g, 90% yield). $^1$H NMR (400 MHz, $CDCl_3$): δ 0.88 (t, 6H), 1.26-1.45 (m, 40H), 1.47 (m, 2H), 1.63 (m, 2H), 2.02 (m, 1H), 2.34 (t, 2H), 3.82 (m, 1H), 3.95 (m, 1H), 4.13 (m, 1H). ESI-MS calculated for $C_{28}H_{57}O_3^+$ [M+H]$^+$ 441.4, found 441.6.

Embodiment 3: 2-((4-(Dimethylamino)Butanoyl)Oxy)Hexadecyl Dodecanoate

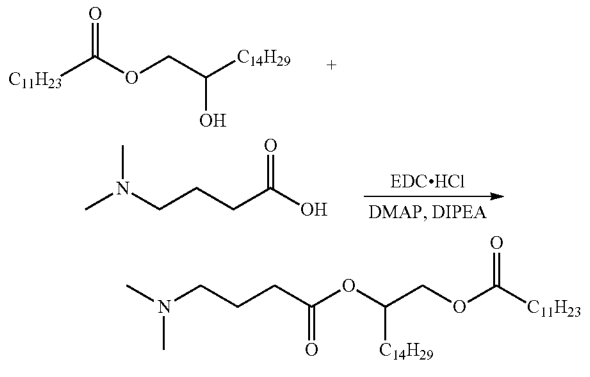

E11C7A9

EDC·HCl (192 mg, 1 mmol), DIPEA (174 μL, 1 mmol), DMAP (3.0 mg, 0.025 mmol), 4-(dimethylamino)butanoic acid (101 mg, 0.6 mmol), 2-hydroxyhexadecyl dodecanoate (220 mg, 0.5 mmol) and DCM (4 mL) were sequentially added into a 10 mL reaction tube. The reaction was stirred at room temperature for 3 h to obtain a compound E11C7A9 (235 mg, 85% yield). $^1$H NMR (400 MHz, $CDCl_3$): δ 0.88 (t, 6H), 1.25-1.45 (m, 40H), 1.58 (m, 4H), 1.78 (m, 2H), 2.23 (s, 6H), 2.30 (m, 6H), 4.01 (m, 1H), 4.21 (m, 1H), 5.08 (m, 1H). $^{13}$C NMR (100 MHz, $CDCl_3$): δ 14.03, 14.08, 22.59, 22.64, 23.35, 25.11, 27.39, 27.43, 29.23, 29.27, 29.29, 29.45, 29.53, 29.59, 30.80, 31.65, 31.85, 31.89, 32.16, 32.39, 47.39, 47.69, 58.86, 64.49, 71.53, 171.87, 173.43. ESI-MS calculated for $C_{34}H_{68}NO_4^+$ [M+H]$^+$ 554.5, found 554.7.

Embodiment 4:2-Hydroxydodecyl-2-Hexyldecanoate

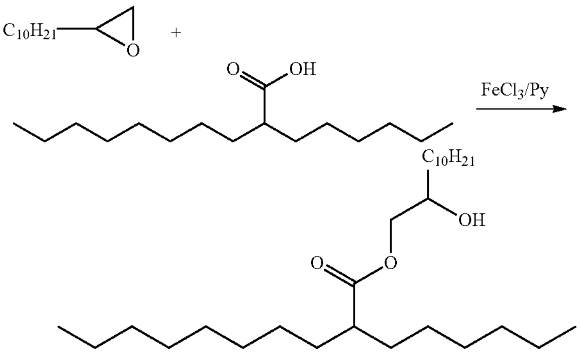

$FeCl_3$ (20 mg, 0.025 mmol), Py (5 μL, 0.0125 mmol), 2-hexyldecanoic acid (1.3 g, 5 mmol) and 1,2-epoxydodecane (1.3 mL, 6 mmol) were sequentially added into a 25 mL reaction tube. Then the reaction was stirred at room temperature overnight, and column chromatography gradient elution purification (hexane:EA=20:1 to 5:1) was performed to obtain the 2-hydroxydodecyl-2-hexyldecanoate (1.9 g, 85% yield). $^1$H NMR (400 MHz, $CDCl_3$): δ 0.88 (t, 9H), 1.26-1.45 (m, 36H), 1.47 (m, 2H), 1.63 (m, 2H), 2.02 (m, 1H), 2.34 (t, 2H), 3.82 (m, 1H), 3.95 (m, 1H), 4.13 (m, 1H). ESI-MS calculated for $C_{28}H_{56}O_3^+$ [M+H]$^+$ 441.4, found 441.5.

Embodiment 5: 2-((4-(Dimethylamino)Butanoyl)Oxy) Dodecyl 2-Hexyldecanoate

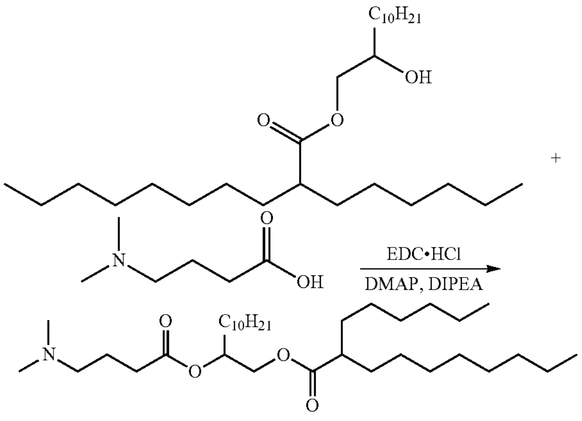

E7C71A9

Figure 2:
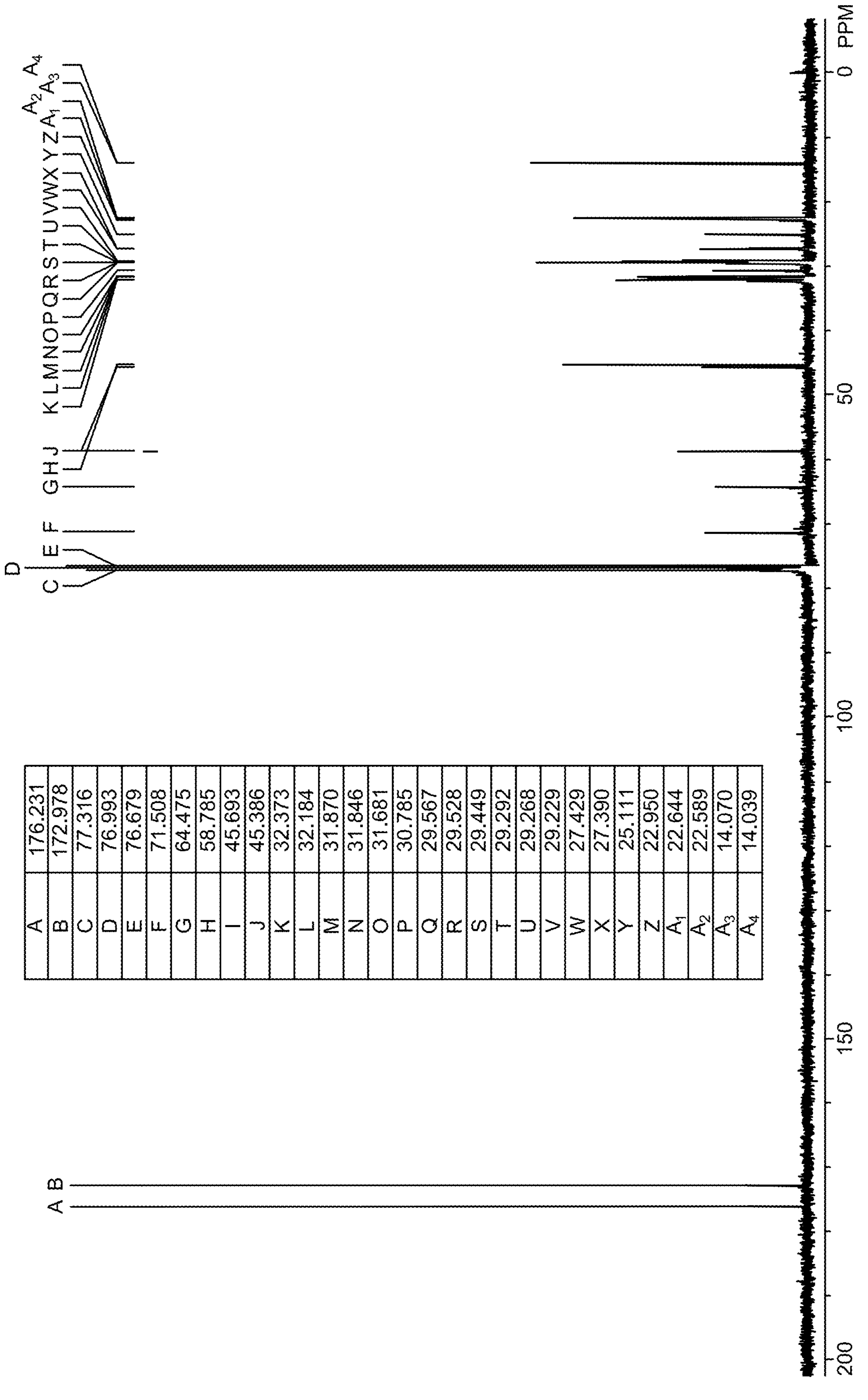
FIG. 2 is a $^{13}$C-NMR spectrum of E7C71A9 in Embodiment 5.

EDC·HCl (192 mg, 1 mmol), DIPEA (174 μL, 1 mmol), DMAP (3.0 mg, 0.025 mmol), 4-(dimethylamino)butanoic acid (101 mg, 0.6 mmol), 2-hydroxydodecyl-2-hexyldecanoate (220 mg, 0.5 mmol) and DCM (4 mL) were sequentially added into a 10 mL reaction tube, and the reaction was stirred at room temperature for 3 h to obtain the compound E7C71A9 (235 mg, 85% yield). $^1$H NMR (400 MHz, $CDCl_3$): δ 0.88 (t, 9H), 1.25-1.45 (m, 38H), 1.58 (m, 4H), 1.79 (m, 2H), 2.12-2.30 (m, 11H), 4.01 (m, 1H), 4.22 (m, 1H), 5.07 (m, 1H) (FIG. 1). $^{13}C$ NMR (100 MHz, $CDCl_3$): δ 14.04, 14.07, 22.59, 22.64, 22.95, 25.11, 27.39, 27.43, 29.23, 29.27, 29.29, 29.45, 29.53, 29.59, 30.79, 31.68, 31.85, 31.87, 32.18, 32.37, 45.3945.69, 58.84, 64.48, 71.51, 172.98, 176.23 (FIG. 2). ESI-MS calculated for $C_{34}H_{67}NO_4^+$ $[M+H]^+$ 554.5, found 554.6.

Embodiment 6: 2-Hydroxydecyl-Octadec-9-Enoate

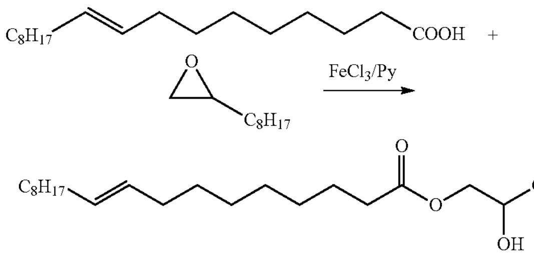

$FeCl_3$ (20 mg, 0.025 mmol), Py (5 μL, 0.0125 mmol), oleic acid (1.6 mL, 5 mmol) and 1,2-epoxydecane (1.1 mL, 6 mmol) are sequentially added into a 25 mL reaction tube, and the reaction was stirred at room temperature overnight. Then column chromatography gradient elution purification (hexane:EA=20:1 to 5:1) was performed to obtain 2-hydroxydecyl-octadec-9-enoate (1.9 g, 85% yield). $^1H$ NMR (400 MHz, $CDCl_3$): δ 0.88 (t, 6H), 1.26-1.45 (m, 34H), 1.63 (m, 2H), 2.17 (m, 4H), 2.33 (m, 2H), 4.09-4.35 (m, 3H), 5.35-5.43 (m, 2H). ESI-MS calculated for $C_{28}H_{55}O_3^+$ $[M+H]^+$ 439.4, found 439.6.

Embodiment 7:1-(Octadec-9-Enoyloxy) Decan-2-Yl 1-Methylpiperidine-4-Carboxylate

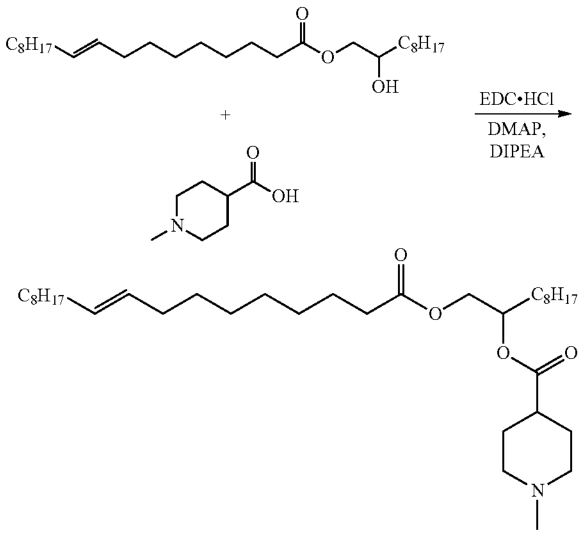

E5C82A23

EDC·HCl (192 mg, 1 mmol), DIPEA (174 μL, 1 mmol), DMAP (3.0 mg, 0.025 mmol), 1-methylpiperidine-4-carboxylic acid (86 mg, 0.6 mmol), 2-hydroxydecyl-octadec-9-enoate (219 mg, 0.5 mmol) and DCM (4 mL) were sequentially added into a 10 mL reaction tube. The reaction was stirred at room temperature for 3 h to obtain the compound E5C82A23 (226 mg, 80% yield). 1H NMR (400 MHz, $CDCl_3$): δ 0.88 (t, 6H), 1.23-1.46 (m, 32H), 1.49 (m, 2H), 1.66 (m, 2H), 1.73-2.03 (m, 4H), 2.11-2.20 (m, 7H), 2.33-2.51 (m, 7H), 4.03 (m, 1H), 4.24 (m, 1H), 5.07 (m, 1H), 5.43 (m, 2H). $^{13}C$ NMR (100 MHz, $CDCl_3$): δ 14.04, 14.06, 22.59, 22.64, 25.01, 25.26, 29.23, 29.25, 29.27, 29.29, 29.45, 29.53, 29.59, 30.80, 31.65, 31.85, 31.90, 32.16, 32.39, 47.39, 47.69, 58.86, 64.49, 71.53, 130.57, 130.63, 171.97, 173.73. ESI-MS calculated for $C_{35}H_{66}NO_4^+$ $[M+H]^+$ 564.5, found 564.6.

Embodiment 8:3,3,4,4,5,5,6,6,7,7,8,8,8-Tridecafluoro-1-Hydroxyoctyl Tetradecanoate

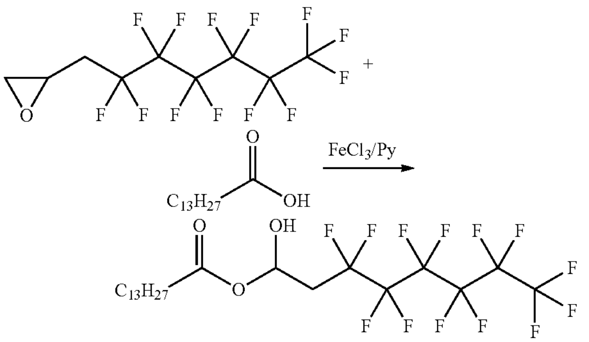

$FeCl_3$ (20 mg, 0.025 mmol), Py (5 μL, 0.0125 mmol), myristic acid (1.1 g, 5 mmol) and 3-(perfluoro-n-hexyl) propenoxide (1.4 mL, 6 mmol) were sequentially added into a 25 mL reaction tube, and the reaction was stirred at room temperature overnight. Then column chromatography gradient elution purification (hexane:EA=20:1 to 5:1) was performed to obtain 3,3,4,4,5,5,6,6,7,7,8,8,8-tridecafluoro-1-hydroxyoctyl tetradecanoate (2.7 g, 90% yield). $^1H$ NMR (400 MHz, $CDCl_3$): δ 0.88 (t, 3H), 1.26-1.45 (m, 20H), 1.63 (m, 2H), 2.03 (m, 2H), 2.36 (t, 2H), 6.68 (t, 1H). ESI-MS calculated for $C_{22}H_{32}F_{13}O_3^+$ $[M+H]^+$ 591.2, found 591.3.

Embodiment 9: 1-((4-(Dimethylamino)Butyryl) Oxy)-3,3,4,4,5,5,6,6,7,7,8,8,8-Tridecafluorooctyl Tetradecanoate

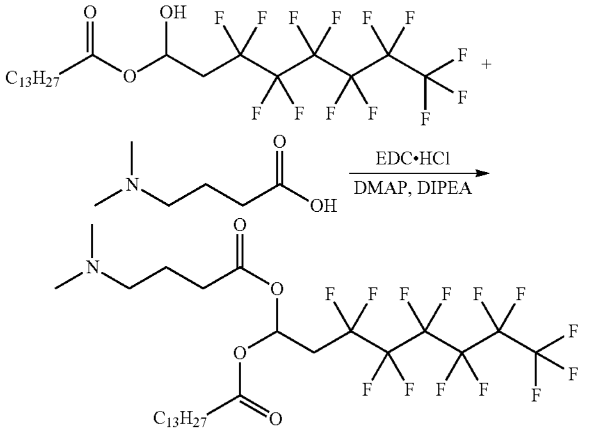

E24C9A9

EDC·HCl (192 mg, 1 mmol), DIPEA (174 μL, 1 mmol), DMAP (3.0 mg, 0.025 mmol), 4-(dimethylamino)butanoic acid (101 mg, 0.6 mmol), 3,3,4,4,5,5,6,6,7,7,8,8,8-tridecafluoro-1-hydroxyoctyl tetradecanooate (295 mg, 0.5 mmol) and DCM (4 mL) were sequentially added into a 10 mL reaction tube, and the reaction was stirred at room temperature for 3 h to obtain the compound E24C9A9 (263.8 mg, 75% yield). $^1$H NMR (400 MHz, $CDCl_3$): δ 0.88 (t, 3H), 1.23-1.60 (m, 20H), 1.66 (m, 2H), 1.88 (m, 2H), 2.05-2.16 (m, 8H), 2.36 (m, 4H), 3.10 (t, 2H), 7.46 (t, 1H). $^{13}$C NMR (100 MHz, $CDCl_3$): δ 14.07, 22.69, 22.95, 25.06, 27.39, 29.25, 29.41, 29.57, 29.59, 30.79, 31.85, 31.87, 32.18, 32.37, 46.39, 46.69, 59.84, 88.37, 109.05, 110.09, 111.89, 112.37, 118.49, 173.67, 176.23. ESI-MS calculated for $C_{28}H_{43}F_{13}NO_4^+$ [M+H]$^+$ 704.3, found 704.5.

Embodiment 10:8-Ethyl-2-Hydroxydecyl Palmitate

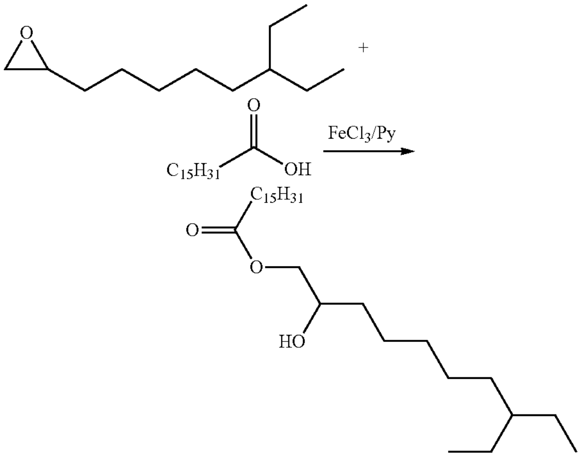

$FeCl_3$ (20 mg, 0.025 mmol), Py (5 μL, 0.0125 mmol), 2-hexyldecanoic acid (1.3 g, 5 mmol) and 2-(6-ethyl octyl) oxirane (1.3 mL, 6 mmol) were sequentially added into a 25 mL reaction tube, and the reaction was stirred at room temperature overnight. Then the column chromatography gradient elution purification (hexane:EA=20:1 to 5:1) was performed to obtain 8-ethyl-2-hydroxydecyl palmitate (2.0 g, 90% yield). $^1$H NMR (400 MHz, $CDCl_3$): δ 0.88 (t, 9H), 1.26-1.45 (m, 37H), 1.47 (m, 2H), 1.63 (m, 2H), 2.02 (m, 1H), 2.34 (t, 2H), 3.82 (m, 1H), 3.95 (m, 1H), 4.13 (m, 1H). ESI-MS calculated for $C_{28}H_{57}O_3^+$ [M+H]$^+$ 441.4, found 441.6.

Embodiment 11:
2-((4-(Dimethylamino)Butyryl)Oxy)-8-Ethyldecyl Palmitate

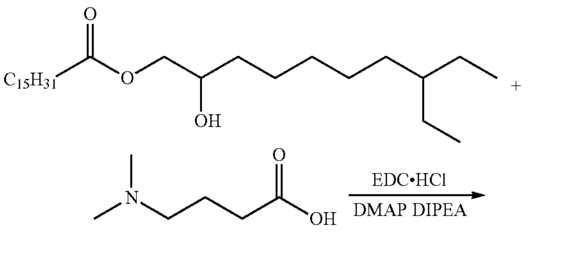

-continued

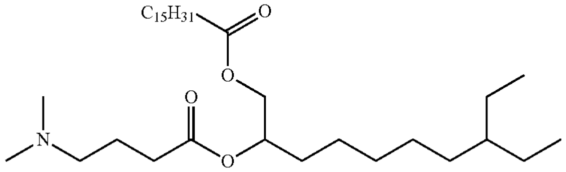

E20C11A9

EDC·HCl (192 mg, 1 mmol), DIPEA (174 μL, 1 mmol), DMAP (3.0 mg, 0.025 mmol), 4-(dimethylamino)butanoic acid (101 mg, 0.6 mmol), 8-ethyl-2-hydroxydecyl palmitate (220 mg, 0.5 mmol) and DCM (4 mL) were sequentially added into a 10 mL reaction tube, and the reaction was stirred at room temperature for 3 h to obtain the compound E20C11A9 (221 mg, 80%). $^1$H NMR (400 MHz, $CDCl_3$): δ 0.88 (t, 9H), 1.25-1.45 (m, 37H), 1.58 (m, 4H), 1.78 (m, 2H), 2.23 (s, 6H), 2.30 (m, 6H), 4.01 (m, 1H), 4.21 (m, 1H), 5.08 (m, 1H). $^{13}$C NMR (100 MHz, $CDCl_3$): δ 12.01, 12.08, 14.09, 22.59, 22.64, 22.95, 25.11, 27.39, 27.43, 29.23, 29.25, 29.31, 29.44, 29.56, 29.59, 30.80, 31.64, 31.83, 31.87, 32.21, 32.33, 46.48, 46.89, 59.45, 65.36, 71.70, 173.48, 176.73. ESI-MS calculated for $C_{34}H_{68}NO_4^+$ [M+H]$^+$ 554.5, found 554.7.

Embodiment 12: In-Vitro Evaluation of Amino Lipid Compound as mRNA Vector

Cell line: HeLa cell line

Culture medium: 1640 (Lipofectamine3000) supplemented with 10% fetal calf serum

Screening form: 96-well plate cell transfection

Detection: fluorescence intensity detection by a multifunctional microplate reader. According to manufacturer's instructions, Lipofectamine3000 was used as a positive control group.

Method: an 8-channel pipette was used for sample addition. The shown content is the content of a single well of a 96-well plate.

1. Synthesis was performed with reference to the route described in Embodiment 1 to obtain a series of amino lipid compounds. The amino lipid compounds were mixed with DSPC, cholesterol and PEG2000-DMG according to a mole ratio of 50:10:38.5:1.5 in absolute ethyl alcohol. The Luc-mRNA was dissolved into a sodium acetate buffer solution (25 nM, pH=5.0). The mixed lipid solution was taken out by a multi-channel pipette tip, and was added into the Luc-mRNA solution to be sufficiently mixed. A proportion ratio of the ethyl alcohol solution to the sodium acetate buffer solution (25 nM, pH=5.0) was controlled to be 1:3, and a nanoparticle solution was prepared. A mass ratio of the amino lipid compound to luciferase mRNA (Luc mRNA) was about 10:1, and the mRNA consumption in each well was 100 ng.

2. After the lipid nanoparticle solution was incubated for 30 min at room temperature, 100 μL of fresh resuspended HeLa cells (1x10$^4$ cells) were added into each well of a 96-well all-white ELISA plate. Then, the lipid nanoparticle solution was added into the 96-well plate (10 μL for each well) by a pipette. The solution was placed into a 37° C. incubator containing 5% $CO_2$ to be incubated.

3. After 16 h to 20 h of cell initial transfection, a substrate ONE-Glo™ Luciferase was added into cells at 100 μL/well, and after 2 min, detection was performed by a multifunctional or multimode microplate reader.

4. The relative transfection efficiency was calculated as follows:

Relative transfection efficiency (%)=fluorescence intensity of LNP/fluorescence intensity of Lipofectamine3000×100%.

Result: the transfection efficiency of parts of compounds on Luc-mRNA of the HeLa cells is shown in Table 2.

TABLE 2 relative transfection efficiency of 4345 kinds of compounds on Luc-mRNA of the HeLa cells

| | A9 | A10 | A11 | A12 | A14 | A15 | A16 | A23 | A24 | A28 | A33 |
|---|---|---|---|---|---|---|---|---|---|---|---|
| E3C10 | 0.2 | 0.4 | 0.4 | 0.1 | 0.1 | 0.1 | 0.2 | 0.1 | 0.2 | 0.1 | 0.1 |
| E3C11 | 0.1 | 0.2 | 0.4 | 0.2 | 0.3 | 0.1 | 0.2 | 0.3 | 0.2 | 0.3 | 0.1 |
| E3C12 | 0.2 | 0.2 | 0.6 | 0.2 | 0.2 | 0.4 | 0.2 | 0.6 | 0.2 | 0.4 | 0.4 |
| E3C13 | 0.5 | 0.8 | 1.9 | 1.2 | 0.6 | 0.2 | 0.4 | 0.7 | 0.4 | 0.6 | 0.2 |
| E3C14 | 1.0 | 1.3 | 3.3 | 1.4 | 0.6 | 0.4 | 0.2 | 0.8 | 0.6 | 0.4 | 0.6 |
| E3C56 | 0.4 | 0.3 | 0.6 | 0.4 | 0.2 | 0.2 | 0.4 | 0.6 | 0.4 | 0.6 | 0.2 |
| E3C57 | 0.2 | 0.7 | 0.2 | 0.5 | 0.6 | 0.2 | 0.6 | 0.2 | 0.4 | 0.3 | 0.2 |
| E3C58 | 0.7 | 1.0 | 0.7 | 0.2 | 0.6 | 0.2 | 0.4 | 0.6 | 0.2 | 0.6 | 0.9 |
| E3C60 | 0.0 | 0.2 | 0.7 | 0.2 | 0.2 | 0.6 | 0.7 | 0.4 | 0.4 | 0.2 | 0.2 |
| E3C62 | 0.0 | 0.0 | 0.5 | 0.0 | 0.6 | 0.2 | 0.4 | 0.6 | 0.3 | 0.6 | 0.6 |
| E3C63 | 0.0 | 0.0 | 0.2 | 0.0 | 0.6 | 0.2 | 0.4 | 0.8 | 0.4 | 0.6 | 0.4 |
| E3C64 | 0.2 | 0.2 | 0.7 | 0.2 | 0.6 | 0.2 | 0.2 | 0.3 | 0.6 | 0.2 | 0.4 |
| E3C66 | 0.2 | 0.2 | 1.0 | 0.5 | 0.4 | 0.4 | 0.7 | 0.6 | 0.4 | 0.6 | 0.8 |
| E3C67 | 0.2 | 0.7 | 1.0 | 0.5 | 0.6 | 0.2 | 0.4 | 0.6 | 0.4 | 0.5 | 0.4 |
| E3C71 | 0.0 | 0.5 | 0.5 | 0.0 | 0.6 | 0.5 | 0.9 | 0.8 | 0.8 | 0.7 | 0.4 |
| E3C72 | 0.5 | 0.2 | 0.7 | 0.2 | 0.6 | 0.5 | 0.6 | 0.6 | 0.4 | 0.8 | 0.4 |
| E3C74 | 0.7 | 1.0 | 0.2 | 0.5 | 0.8 | 0.2 | 0.4 | 0.7 | 0.8 | 0.6 | 0.7 |
| E3C79 | 0.8 | 1.2 | 4.6 | 3.8 | 0.6 | 0.5 | 0.4 | 0.6 | 0.4 | 0.6 | 0.2 |
| E3C82 | 0.1 | 0.3 | 0.3 | 0.1 | 0.3 | 0.3 | 0.2 | 0.3 | 0.2 | 0.3 | 0.1 |
| E3C83 | 0.1 | 0.1 | 0.3 | 0.2 | 0.1 | 0.1 | 0.5 | 0.7 | 0.7 | 0.3 | 0.1 |
| E4C10 | 0.1 | 0.2 | 0.2 | 0.1 | 0.1 | 0.1 | 0.2 | 0.1 | 0.2 | 0.1 | 0.1 |
| E4C11 | 0.1 | 0.2 | 0.4 | 0.2 | 0.3 | 0.1 | 0.2 | 0.3 | 0.2 | 0.3 | 0.1 |
| E4C12 | 0.3 | 1.0 | 1.5 | 0.9 | 0.1 | 0.1 | 0.4 | 0.1 | 0.4 | 0.1 | 0.1 |
| E4C13 | 0.7 | 1.7 | 2.7 | 1.2 | 0.3 | 0.6 | 0.2 | 0.3 | 0.2 | 0.3 | 0.1 |
| E4C14 | 0.3 | 0.4 | 0.7 | 0.3 | 0.1 | 0.2 | 0.1 | 0.3 | 0.1 | 0.2 | 0.2 |
| E4C56 | 0.6 | 0.4 | 0.8 | 0.6 | 0.3 | 0.1 | 0.2 | 0.8 | 0.2 | 0.3 | 0.1 |
| E4C57 | 0.2 | 0.6 | 0.2 | 0.4 | 0.3 | 0.2 | 0.1 | 0.4 | 0.3 | 0.2 | 0.3 |
| E4C58 | 0.6 | 0.8 | 0.6 | 0.5 | 0.3 | 0.7 | 0.5 | 0.3 | 0.2 | 0.3 | 0.1 |
| E4C60 | 0.0 | 0.2 | 0.6 | 0.5 | 0.8 | 0.3 | 0.8 | 0.1 | 0.2 | 0.5 | 0.2 |
| E4C62 | 0.0 | 0.0 | 0.4 | 0.0 | 0.8 | 0.3 | 0.5 | 0.3 | 0.6 | 0.6 | 0.2 |
| E4C63 | 0.0 | 0.0 | 0.2 | 0.0 | 0.3 | 0.8 | 0.5 | 0.2 | 0.2 | 0.2 | 0.2 |
| E4C64 | 0.2 | 0.2 | 0.6 | 0.2 | 0.3 | 0.1 | 0.2 | 0.3 | 0.2 | 0.7 | 0.6 |
| E4C66 | 0.2 | 0.2 | 0.8 | 0.4 | 0.3 | 0.1 | 0.2 | 0.4 | 0.2 | 0.6 | 0.2 |
| E4C67 | 0.2 | 0.6 | 0.8 | 0.4 | 0.3 | 0.1 | 0.6 | 0.2 | 0.3 | 0.2 | 0.2 |
| E4C71 | 0.0 | 0.4 | 0.4 | 0.0 | 0.2 | 0.6 | 0.2 | 0.3 | 0.2 | 0.9 | 0.2 |
| E4C72 | 0.8 | 0.4 | 1.2 | 0.4 | 0.3 | 0.1 | 0.2 | 0.2 | 0.2 | 0.3 | 0.8 |
| E4C74 | 2.4 | 3.7 | 5.1 | 4.3 | 0.3 | 0.1 | 0.2 | 0.4 | 0.6 | 0.3 | 0.1 |
| E4C79 | 2.9 | 4.5 | 6.1 | 5.1 | 0.6 | 0.1 | 0.3 | 0.3 | 0.1 | 0.6 | 0.1 |
| E4C82 | 0.1 | 0.3 | 0.3 | 0.1 | 0.2 | 0.1 | 0.1 | 0.4 | 0.1 | 0.2 | 0.1 |
| E4C83 | 0.1 | 0.1 | 0.3 | 0.2 | 0.2 | 0.1 | 0.1 | 0.2 | 0.1 | 0.2 | 0.1 |
| E5C10 | 0.2 | 0.4 | 0.4 | 0.1 | 0.1 | 0.1 | 0.4 | 0.1 | 0.4 | 0.1 | 0.1 |
| E5C11 | 0.8 | 1.0 | 2.9 | 1.3 | 0.3 | 0.1 | 0.2 | 0.3 | 0.2 | 0.3 | 0.1 |
| E5C12 | 0.5 | 0.7 | 1.8 | 1.1 | 0.1 | 0.1 | 0.4 | 0.1 | 0.4 | 0.1 | 0.1 |
| E5C13 | 0.9 | 1.2 | 3.3 | 1.4 | 0.3 | 0.7 | 0.2 | 0.3 | 0.2 | 0.3 | 0.4 |
| E5C14 | 0.2 | 0.3 | 0.8 | 0.4 | 0.1 | 0.2 | 0.1 | 0.3 | 0.1 | 0.6 | 0.6 |
| E5C56 | 0.7 | 0.4 | 0.9 | 0.7 | 0.3 | 0.1 | 0.2 | 0.9 | 0.2 | 0.9 | 0.3 |
| E5C57 | 0.2 | 0.7 | 0.2 | 0.4 | 0.3 | 0.2 | 0.1 | 0.4 | 0.3 | 0.6 | 0.9 |
| E5C58 | 0.7 | 0.9 | 0.7 | 0.2 | 0.1 | 0.4 | 0.2 | 0.3 | 0.2 | 0.9 | 0.3 |
| E5C60 | 0.0 | 0.2 | 0.7 | 0.2 | 0.3 | 0.1 | 0.3 | 0.1 | 0.2 | 0.3 | 0.3 |
| E5C62 | 0.0 | 0.0 | 0.4 | 0.0 | 0.3 | 0.1 | 0.2 | 0.3 | 0.7 | 0.9 | 0.3 |
| E5C63 | 0.0 | 0.0 | 0.2 | 0.0 | 0.1 | 0.3 | 0.2 | 0.2 | 0.2 | 0.3 | 0.3 |
| E5C64 | 0.2 | 0.2 | 0.7 | 0.2 | 0.8 | 0.1 | 0.2 | 0.3 | 0.2 | 0.9 | 0.9 |
| E5C66 | 0.2 | 0.2 | 0.5 | 0.4 | 0.3 | 0.4 | 0.2 | 0.4 | 0.2 | 0.3 | 0.1 |
| E5C67 | 0.2 | 0.7 | 0.5 | 0.4 | 0.3 | 0.1 | 0.7 | 0.2 | 0.3 | 0.1 | 0.1 |
| E5C71 | 0.6 | 0.9 | 4.0 | 0.6 | 0.2 | 0.7 | 0.2 | 0.3 | 0.2 | 0.3 | 0.1 |
| E5C72 | 0.5 | 0.8 | 3.6 | 0.6 | 0.3 | 0.1 | 0.2 | 0.2 | 0.2 | 0.3 | 0.9 |
| E5C74 | 0.6 | 3.2 | 4.3 | 0.7 | 0.3 | 0.1 | 0.2 | 0.4 | 0.7 | 0.3 | 0.1 |
| E5C79 | 0.8 | 3.8 | 5.2 | 0.8 | 0.7 | 0.1 | 0.3 | 0.3 | 0.1 | 0.7 | 0.1 |
| E5C82 | 0.2 | 0.7 | 0.7 | 0.2 | 0.4 | 0.4 | 0.2 | 0.9 | 0.2 | 0.3 | 0.6 |
| E5C83 | 0.1 | 0.1 | 0.3 | 0.2 | 0.2 | 0.1 | 0.1 | 0.2 | 0.1 | 0.2 | 0.1 |
| E6C9 | 0.2 | 0.4 | 0.4 | 0.1 | 0.1 | 0.1 | 0.4 | 0.1 | 0.4 | 0.1 | 0.1 |
| E6C10 | 0.9 | 1.9 | 1.4 | 0.6 | 0.2 | 0.5 | 0.1 | 0.2 | 0.1 | 0.2 | 0.1 |
| E6C11 | 0.8 | 1.7 | 1.3 | 0.9 | 0.2 | 0.1 | 0.1 | 0.2 | 0.1 | 0.2 | 0.1 |
| E6C12 | 0.2 | 0.6 | 0.8 | 0.8 | 0.1 | 0.7 | 0.3 | 0.1 | 0.3 | 0.1 | 0.1 |
| E6C13 | 0.5 | 0.9 | 1.4 | 1.0 | 0.5 | 0.6 | 0.3 | 0.2 | 0.1 | 0.2 | 0.2 |

TABLE 2-continued

| relative transfection efficiency of 4345 kinds of compounds on Luc-mRNA of the HeLa cells | | | | | | | | | | | |
|---|---|---|---|---|---|---|---|---|---|---|---|
| | A9 | A10 | A11 | A12 | A14 | A15 | A16 | A23 | A24 | A28 | A33 |
| E6C14 | 0.6 | 0.8 | 1.2 | 0.5 | 0.2 | 0.3 | 0.2 | 0.2 | 0.1 | 0.1 | 0.1 |
| E6C56 | 0.4 | 0.3 | 0.5 | 0.4 | 0.5 | 0.2 | 0.3 | 0.5 | 0.1 | 0.2 | 0.1 |
| E6C57 | 0.1 | 0.4 | 0.1 | 0.3 | 0.5 | 0.3 | 0.2 | 0.3 | 0.2 | 0.1 | 0.2 |
| E6C58 | 0.4 | 0.5 | 0.4 | 0.1 | 0.2 | 0.7 | 0.3 | 0.2 | 0.1 | 0.2 | 0.1 |
| E6C60 | 0.0 | 0.1 | 0.4 | 0.1 | 0.5 | 0.2 | 0.5 | 0.1 | 0.1 | 0.2 | 0.1 |
| E6C62 | 0.0 | 0.0 | 0.3 | 0.0 | 0.2 | 0.1 | 0.8 | 0.2 | 0.4 | 0.2 | 0.6 |
| E6C63 | 0.0 | 0.0 | 0.1 | 0.0 | 0.1 | 0.2 | 0.1 | 0.1 | 0.1 | 0.1 | 0.1 |
| E6C64 | 0.1 | 0.1 | 0.4 | 0.1 | 0.2 | 0.1 | 0.1 | 0.2 | 0.1 | 0.2 | 0.2 |
| E6C66 | 0.1 | 0.1 | 0.5 | 0.3 | 0.2 | 0.1 | 0.1 | 0.3 | 0.4 | 0.2 | 0.1 |
| E6C67 | 1.2 | 1.8 | 7.1 | 6.0 | 0.2 | 0.1 | 0.4 | 0.8 | 0.2 | 0.1 | 0.5 |
| E6C71 | 2.6 | 0.9 | 3.5 | 3.0 | 0.1 | 0.8 | 0.3 | 0.4 | 0.3 | 0.4 | 0.1 |
| E6C72 | 0.5 | 0.3 | 3.2 | 0.2 | 0.6 | 0.1 | 0.3 | 0.3 | 0.3 | 0.4 | 0.9 |
| E6C74 | 0.6 | 2.8 | 3.8 | 1.1 | 0.2 | 0.1 | 0.3 | 0.7 | 0.8 | 0.4 | 0.1 |
| E6C79 | 0.8 | 3.4 | 4.6 | 1.3 | 0.4 | 0.1 | 0.4 | 0.4 | 0.1 | 0.8 | 0.1 |
| E6C82 | 0.1 | 0.4 | 0.4 | 0.1 | 0.3 | 0.5 | 0.3 | 0.8 | 0.3 | 0.4 | 0.7 |
| E6C83 | 0.1 | 0.1 | 0.4 | 0.3 | 0.2 | 0.1 | 0.3 | 0.4 | 0.3 | 0.4 | 0.1 |
| E7C8 | 0.2 | 0.4 | 0.4 | 0.1 | 0.1 | 0.1 | 0.4 | 0.1 | 0.4 | 0.1 | 0.1 |
| E7C9 | 1.2 | 0.9 | 1.4 | 1.0 | 0.1 | 0.1 | 0.6 | 0.1 | 0.6 | 0.1 | 0.1 |
| E7C10 | 0.7 | 0.5 | 0.8 | 0.6 | 0.4 | 0.4 | 0.2 | 0.4 | 0.8 | 0.4 | 0.4 |
| E7C11 | 1.1 | 0.8 | 1.2 | 0.9 | 0.3 | 0.6 | 0.2 | 0.3 | 0.2 | 0.3 | 0.6 |
| E7C12 | 0.6 | 0.3 | 0.8 | 0.8 | 0.4 | 0.2 | 0.3 | 0.2 | 0.3 | 0.6 | 0.1 |
| E7C13 | 0.4 | 0.9 | 1.4 | 1.0 | 0.3 | 0.5 | 0.2 | 0.3 | 0.2 | 0.3 | 0.3 |
| E7C14 | 0.6 | 0.4 | 0.7 | 0.5 | 0.6 | 0.2 | 0.1 | 0.3 | 0.1 | 0.2 | 0.2 |
| E7C56 | 0.5 | 0.3 | 0.7 | 0.5 | 0.3 | 0.1 | 0.2 | 0.7 | 0.2 | 0.3 | 0.1 |
| E7C57 | 0.2 | 0.5 | 0.2 | 0.3 | 0.3 | 0.2 | 0.1 | 0.3 | 0.3 | 0.6 | 0.3 |
| E7C58 | 0.5 | 0.7 | 0.5 | 0.2 | 0.6 | 0.3 | 0.2 | 0.3 | 0.2 | 0.3 | 0.6 |
| E7C60 | 0.0 | 0.2 | 0.5 | 0.2 | 0.3 | 0.2 | 0.3 | 0.6 | 0.2 | 0.3 | 0.4 |
| E7C62 | 0.0 | 0.0 | 0.3 | 0.0 | 0.3 | 0.6 | 0.8 | 0.3 | 0.5 | 0.3 | 0.8 |
| E7C63 | 0.0 | 0.0 | 0.2 | 0.0 | 0.4 | 0.3 | 0.2 | 0.2 | 0.2 | 0.4 | 0.1 |
| E7C64 | 0.2 | 0.2 | 0.5 | 0.2 | 0.3 | 0.4 | 0.2 | 0.3 | 0.8 | 0.3 | 0.3 |
| E7C66 | 0.2 | 0.2 | 0.7 | 0.3 | 0.3 | 0.1 | 0.2 | 0.3 | 0.5 | 0.3 | 0.1 |
| E7C67 | 1.1 | 5.6 | 5.3 | 1.4 | 0.8 | 0.1 | 0.5 | 0.8 | 0.3 | 0.1 | 0.6 |
| E7C71 | 1.5 | 2.8 | 2.7 | 0.7 | 0.2 | 0.5 | 0.2 | 0.3 | 0.4 | 0.3 | 0.2 |
| E7C72 | 0.5 | 0.8 | 0.8 | 0.6 | 0.8 | 0.1 | 0.7 | 0.2 | 0.2 | 0.8 | 0.7 |
| E7C74 | 2.0 | 3.0 | 2.9 | 2.4 | 0.3 | 0.1 | 0.2 | 0.8 | 0.5 | 0.3 | 0.1 |
| E7C79 | 2.3 | 3.7 | 3.5 | 2.9 | 0.5 | 0.1 | 0.3 | 0.3 | 0.1 | 0.5 | 0.2 |
| E7C82 | 0.2 | 0.5 | 0.5 | 0.2 | 0.3 | 0.3 | 0.2 | 0.7 | 0.2 | 0.3 | 0.5 |
| E7C83 | 0.2 | 0.2 | 0.5 | 0.3 | 0.3 | 0.1 | 0.9 | 0.3 | 0.6 | 0.3 | 0.1 |
| E8C7 | 0.1 | 0.1 | 0.3 | 0.2 | 0.1 | 0.0 | 0.1 | 0.1 | 0.3 | 0.1 | 0.0 |
| E8C8 | 0.2 | 0.3 | 0.3 | 0.2 | 0.2 | 0.1 | 0.1 | 0.2 | 0.1 | 0.2 | 0.1 |
| E8C9 | 0.3 | 0.2 | 0.4 | 0.3 | 0.1 | 0.1 | 0.6 | 0.1 | 0.6 | 0.1 | 0.1 |
| E8C10 | 0.5 | 0.4 | 0.6 | 0.4 | 0.4 | 0.4 | 0.2 | 0.4 | 0.8 | 0.4 | 0.4 |
| E8C11 | 0.8 | 0.6 | 0.9 | 0.7 | 0.3 | 0.6 | 0.2 | 0.3 | 0.2 | 0.3 | 0.6 |
| E8C12 | 0.4 | 0.4 | 0.6 | 0.6 | 0.4 | 0.2 | 0.3 | 0.6 | 0.3 | 0.6 | 0.1 |
| E8C13 | 0.9 | 0.6 | 1.0 | 0.7 | 0.4 | 0.7 | 0.2 | 0.4 | 0.2 | 0.4 | 0.4 |
| E8C14 | 3.9 | 2.9 | 4.4 | 3.3 | 0.8 | 0.2 | 0.1 | 0.4 | 0.3 | 0.2 | 0.2 |
| E8C56 | 0.5 | 0.3 | 0.7 | 0.5 | 0.4 | 0.1 | 0.4 | 0.6 | 0.2 | 0.4 | 0.3 |
| E8C57 | 0.2 | 0.5 | 0.2 | 0.3 | 0.4 | 0.2 | 0.1 | 0.5 | 0.6 | 0.8 | 0.4 |
| E8C58 | 0.5 | 0.7 | 0.5 | 0.2 | 0.8 | 0.5 | 0.2 | 0.4 | 0.2 | 0.4 | 0.8 |
| E8C60 | 0.0 | 0.2 | 0.5 | 0.2 | 0.4 | 0.3 | 0.4 | 0.8 | 0.2 | 0.4 | 0.6 |
| E8C62 | 0.5 | 0.8 | 0.8 | 0.6 | 0.4 | 0.8 | 0.6 | 0.4 | 0.7 | 0.4 | 0.2 |
| E8C63 | 0.7 | 0.6 | 0.6 | 0.8 | 0.6 | 0.4 | 0.2 | 0.2 | 0.2 | 0.6 | 0.8 |
| E8C64 | 0.7 | 0.7 | 0.6 | 0.9 | 0.4 | 0.6 | 0.2 | 0.4 | 0.4 | 0.4 | 0.4 |
| E8C66 | 0.7 | 0.6 | 0.6 | 0.8 | 0.4 | 0.1 | 0.2 | 0.5 | 0.7 | 0.4 | 0.6 |
| E8C67 | 0.5 | 0.5 | 0.8 | 0.6 | 0.3 | 0.1 | 0.7 | 0.6 | 0.4 | 0.1 | 0.8 |
| E8C71 | 3.6 | 0.6 | 3.1 | 4.5 | 0.1 | 0.7 | 0.2 | 0.4 | 0.6 | 0.4 | 0.3 |
| E8C72 | 3.3 | 0.5 | 2.8 | 4.1 | 0.7 | 0.1 | 0.2 | 0.2 | 0.2 | 0.4 | 0.4 |
| E8C74 | 3.9 | 0.7 | 3.3 | 4.9 | 0.2 | 0.1 | 0.2 | 0.6 | 0.7 | 0.4 | 0.3 |
| E8C79 | 4.7 | 3.8 | 6.0 | 5.8 | 0.4 | 0.1 | 0.4 | 0.4 | 0.1 | 0.7 | 0.3 |
| E8C82 | 0.2 | 0.5 | 0.5 | 0.2 | 0.5 | 0.4 | 0.2 | 0.2 | 0.2 | 0.4 | 0.6 |
| E8C83 | 0.2 | 0.2 | 0.5 | 0.3 | 0.4 | 0.1 | 0.2 | 0.4 | 0.8 | 0.4 | 0.3 |
| E9C3 | 0.0 | 0.0 | 0.0 | 0.0 | 0.0 | 0.0 | 0.0 | 0.0 | 0.0 | 0.0 | 0.0 |
| E9C4 | 0.0 | 0.0 | 0.0 | 0.0 | 0.0 | 0.0 | 0.0 | 0.0 | 0.0 | 0.0 | 0.0 |
| E9C5 | 0.0 | 0.0 | 0.0 | 0.0 | 0.0 | 0.0 | 0.0 | 0.0 | 0.0 | 0.0 | 0.0 |
| E9C6 | 0.1 | 0.2 | 0.2 | 0.1 | 0.1 | 0.1 | 0.2 | 0.1 | 0.2 | 0.1 | 0.1 |
| E9C7 | 0.2 | 0.3 | 0.3 | 0.3 | 0.2 | 0.2 | 0.1 | 0.2 | 0.4 | 0.2 | 0.2 |
| E9C8 | 0.6 | 0.9 | 0.8 | 0.7 | 0.1 | 0.1 | 0.4 | 0.1 | 0.4 | 0.1 | 0.1 |
| E9C9 | 0.5 | 0.8 | 0.8 | 0.6 | 0.1 | 0.1 | 0.6 | 0.1 | 0.6 | 0.1 | 0.1 |
| E9C10 | 0.6 | 0.6 | 0.4 | 0.8 | 0.4 | 0.4 | 0.2 | 0.4 | 0.8 | 0.4 | 0.4 |
| E9C11 | 0.5 | 0.8 | 0.7 | 0.6 | 0.3 | 0.6 | 0.2 | 0.3 | 0.2 | 0.3 | 0.6 |
| E9C12 | 0.8 | 0.6 | 0.4 | 0.7 | 0.4 | 0.2 | 0.3 | 0.2 | 0.3 | 0.6 | 0.1 |
| E9C13 | 0.5 | 0.6 | 0.5 | 0.5 | 0.3 | 0.5 | 0.2 | 0.3 | 0.2 | 0.3 | 0.3 |
| E9C14 | 0.6 | 3.0 | 0.5 | 0.4 | 0.6 | 0.2 | 0.1 | 0.3 | 0.1 | 0.2 | 0.2 |
| E9C56 | 0.7 | 3.6 | 0.6 | 0.5 | 0.3 | 0.1 | 0.2 | 0.7 | 0.2 | 0.3 | 0.1 |
| E9C57 | 0.9 | 4.3 | 0.8 | 0.6 | 0.3 | 0.2 | 0.1 | 0.3 | 0.3 | 0.6 | 0.3 |

TABLE 2-continued

| relative transfection efficiency of 4345 kinds of compounds on Luc-mRNA of the HeLa cells | | | | | | | | | | | |
|---|---|---|---|---|---|---|---|---|---|---|---|
| | A9 | A10 | A11 | A12 | A14 | A15 | A16 | A23 | A24 | A28 | A33 |
| E9C58 | 1.3 | 6.6 | 1.2 | 1.0 | 0.6 | 0.3 | 0.2 | 0.3 | 0.2 | 0.3 | 0.6 |
| E9C60 | 0.8 | 4.1 | 0.7 | 0.6 | 0.3 | 0.2 | 0.3 | 0.6 | 0.2 | 0.3 | 0.4 |
| E9C62 | 0.8 | 3.8 | 0.7 | 0.6 | 0.3 | 0.6 | 0.8 | 0.3 | 0.5 | 0.3 | 0.8 |
| E9C63 | 0.9 | 4.5 | 0.8 | 0.7 | 0.4 | 0.3 | 0.2 | 0.2 | 0.2 | 0.4 | 0.1 |
| E9C64 | 1.1 | 5.4 | 1.0 | 0.8 | 0.3 | 0.4 | 0.2 | 0.3 | 0.8 | 0.3 | 0.3 |
| E9C66 | 1.7 | 8.3 | 1.5 | 1.2 | 0.3 | 0.1 | 0.2 | 0.3 | 0.5 | 0.3 | 0.1 |
| E9C67 | 0.8 | 4.1 | 0.7 | 0.6 | 0.8 | 0.1 | 0.5 | 0.8 | 0.3 | 0.1 | 0.6 |
| E9C71 | 0.8 | 3.8 | 0.7 | 0.6 | 0.2 | 0.5 | 0.2 | 0.3 | 0.4 | 0.3 | 0.2 |
| E9C72 | 0.9 | 4.5 | 0.8 | 0.7 | 0.8 | 0.1 | 0.2 | 0.2 | 0.2 | 0.3 | 0.7 |
| E9C74 | 1.1 | 5.4 | 3.1 | 0.8 | 0.3 | 0.1 | 0.2 | 0.8 | 0.5 | 0.3 | 0.1 |
| E9C79 | 0.6 | 3.2 | 1.8 | 0.5 | 0.5 | 0.1 | 0.3 | 0.3 | 0.1 | 0.5 | 0.2 |
| E9C82 | 0.2 | 0.5 | 0.5 | 0.2 | 0.3 | 0.3 | 0.2 | 0.7 | 0.2 | 0.3 | 0.5 |
| E9C83 | 0.2 | 0.2 | 0.5 | 0.3 | 0.3 | 0.1 | 0.2 | 0.3 | 0.6 | 0.3 | 0.1 |
| E10C3 | 0.0 | 0.0 | 0.0 | 0.0 | 0.0 | 0.0 | 0.0 | 0.0 | 0.0 | 0.0 | 0.0 |
| E10C4 | 0.0 | 0.0 | 0.0 | 0.0 | 0.0 | 0.0 | 0.0 | 0.0 | 0.0 | 0.0 | 0.0 |
| E10C5 | 0.2 | 0.1 | 0.1 | 0.1 | 0.1 | 0.2 | 0.0 | 0.1 | 0.1 | 0.2 | 0.0 |
| E10C6 | 0.2 | 0.2 | 0.2 | 0.1 | 0.3 | 0.2 | 0.1 | 0.1 | 0.1 | 0.1 | 0.3 |
| E10C7 | 0.2 | 0.3 | 0.2 | 0.2 | 0.1 | 0.1 | 0.1 | 0.3 | 0.1 | 0.1 | 0.2 |
| E10C8 | 0.7 | 0.8 | 0.6 | 0.5 | 0.3 | 0.6 | 0.8 | 0.3 | 0.5 | 0.3 | 0.8 |
| E10C9 | 0.4 | 0.4 | 0.3 | 0.3 | 0.4 | 0.3 | 0.2 | 0.2 | 0.2 | 0.4 | 0.1 |
| E10C10 | 0.5 | 0.4 | 0.6 | 0.4 | 0.4 | 0.4 | 0.2 | 0.4 | 0.8 | 0.4 | 0.4 |
| E10C11 | 0.8 | 0.6 | 0.9 | 0.7 | 0.3 | 0.6 | 0.2 | 0.3 | 0.2 | 0.3 | 0.6 |
| E10C12 | 0.4 | 0.4 | 0.6 | 0.6 | 0.4 | 0.2 | 0.3 | 0.6 | 0.3 | 0.6 | 0.1 |
| E10C13 | 0.9 | 0.6 | 0.6 | 0.7 | 0.4 | 0.7 | 0.2 | 0.4 | 0.2 | 0.4 | 0.4 |
| E10C14 | 3.9 | 2.9 | 4.4 | 3.3 | 0.8 | 0.2 | 0.1 | 0.4 | 0.3 | 0.2 | 0.2 |
| E10C56 | 0.5 | 0.3 | 0.7 | 0.5 | 0.4 | 0.1 | 0.4 | 0.6 | 0.2 | 0.4 | 0.3 |
| E10C57 | 0.2 | 0.5 | 0.2 | 0.3 | 0.4 | 0.2 | 0.1 | 0.5 | 0.6 | 0.8 | 0.4 |
| E10C58 | 0.5 | 0.7 | 0.5 | 0.2 | 0.8 | 0.5 | 0.2 | 0.4 | 0.2 | 0.4 | 0.8 |
| E10C60 | 0.0 | 0.2 | 0.5 | 0.2 | 0.4 | 0.3 | 0.4 | 0.8 | 0.2 | 0.4 | 0.6 |
| E10C62 | 0.5 | 0.8 | 0.8 | 0.6 | 0.4 | 0.8 | 0.6 | 0.4 | 0.7 | 0.4 | 0.2 |
| E10C63 | 0.7 | 0.6 | 0.6 | 0.8 | 0.6 | 0.4 | 0.2 | 0.2 | 0.2 | 0.6 | 0.8 |
| E10C64 | 0.7 | 0.7 | 0.6 | 0.6 | 0.4 | 0.6 | 0.2 | 0.4 | 0.4 | 0.4 | 0.4 |
| E10C66 | 0.7 | 0.6 | 0.6 | 0.8 | 0.4 | 0.1 | 0.2 | 0.5 | 0.7 | 0.4 | 0.6 |
| E10C67 | 0.5 | 0.5 | 0.8 | 0.6 | 0.3 | 0.1 | 0.7 | 0.6 | 0.4 | 0.1 | 0.8 |
| E10C71 | 0.6 | 0.4 | 1.8 | 1.2 | 0.1 | 0.7 | 0.2 | 0.4 | 0.6 | 0.4 | 0.3 |
| E10C72 | 1.9 | 0.3 | 1.6 | 0.8 | 0.7 | 0.1 | 0.2 | 0.2 | 0.2 | 0.4 | 0.4 |
| E10C74 | 2.3 | 1.3 | 2.0 | 0.6 | 0.2 | 0.1 | 0.2 | 0.6 | 0.7 | 0.4 | 0.3 |
| E10C79 | 2.8 | 2.3 | 3.6 | 1.5 | 0.4 | 0.1 | 0.4 | 0.4 | 0.1 | 0.7 | 0.3 |
| E10C82 | 0.2 | 0.5 | 0.5 | 0.2 | 0.5 | 0.4 | 0.2 | 0.2 | 0.2 | 0.4 | 0.6 |
| E10C83 | 0.2 | 0.2 | 0.5 | 0.3 | 0.4 | 0.1 | 0.2 | 0.4 | 0.8 | 0.4 | 0.3 |
| E11C6 | 0.2 | 0.4 | 0.4 | 0.1 | 0.1 | 0.1 | 0.4 | 0.1 | 0.4 | 0.1 | 0.1 |
| E11C7 | 1.9 | 2.4 | 12.8 | 2.0 | 0.8 | 0.4 | 0.3 | 0.8 | 0.9 | 0.8 | 0.8 |
| E11C8 | 0.6 | 0.9 | 0.8 | 0.7 | 0.1 | 0.1 | 0.4 | 0.1 | 0.4 | 0.1 | 0.1 |
| E11C9 | 0.5 | 0.8 | 0.8 | 0.6 | 0.1 | 0.1 | 0.6 | 0.1 | 0.6 | 0.1 | 0.1 |
| E11C10 | 0.6 | 0.6 | 0.4 | 0.8 | 0.4 | 0.4 | 0.2 | 0.4 | 0.8 | 0.4 | 0.4 |
| E11C11 | 0.5 | 0.8 | 0.7 | 0.6 | 0.3 | 0.6 | 0.2 | 0.3 | 0.2 | 0.3 | 0.6 |
| E11C12 | 0.8 | 0.6 | 0.4 | 0.7 | 0.4 | 0.2 | 0.3 | 0.2 | 0.3 | 0.6 | 0.1 |
| E11C13 | 0.5 | 0.6 | 0.5 | 0.5 | 0.3 | 0.5 | 0.2 | 0.3 | 0.2 | 0.3 | 0.3 |
| E11C14 | 0.6 | 0.8 | 0.5 | 0.4 | 0.6 | 0.2 | 0.1 | 0.3 | 0.1 | 0.2 | 0.2 |
| E11C56 | 0.7 | 0.4 | 0.6 | 0.5 | 0.3 | 0.1 | 0.2 | 0.7 | 0.2 | 0.3 | 0.1 |
| E11C57 | 0.6 | 0.7 | 4.3 | 0.6 | 0.3 | 0.2 | 0.1 | 0.3 | 0.3 | 0.6 | 0.3 |
| E11C58 | 0.9 | 1.2 | 6.6 | 1.0 | 0.6 | 0.3 | 0.2 | 0.3 | 0.2 | 0.3 | 0.6 |
| E11C60 | 0.6 | 0.7 | 4.1 | 0.6 | 0.3 | 0.2 | 0.3 | 0.6 | 0.2 | 0.3 | 0.4 |
| E11C62 | 0.5 | 0.7 | 3.8 | 0.6 | 0.3 | 0.6 | 0.8 | 0.3 | 0.5 | 0.3 | 0.8 |
| E11C63 | 0.4 | 0.8 | 0.6 | 0.5 | 0.4 | 0.3 | 0.2 | 0.2 | 0.2 | 0.4 | 0.1 |
| E11C64 | 0.8 | 1.4 | 0.7 | 0.6 | 0.3 | 0.4 | 0.2 | 0.3 | 0.8 | 0.3 | 0.3 |
| E11C66 | 1.2 | 2.1 | 1.0 | 0.9 | 0.3 | 0.1 | 0.2 | 0.3 | 0.5 | 0.3 | 0.1 |
| E11C67 | 1.0 | 0.5 | 0.5 | 0.4 | 0.8 | 0.1 | 0.5 | 0.8 | 0.3 | 0.1 | 0.6 |
| E11C71 | 1.4 | 0.7 | 0.7 | 0.6 | 0.2 | 0.5 | 0.2 | 0.3 | 0.4 | 0.3 | 0.2 |
| E11C72 | 1.6 | 0.8 | 0.8 | 0.7 | 0.8 | 0.1 | 0.2 | 0.2 | 0.2 | 0.3 | 0.7 |
| E11C74 | 1.4 | 0.7 | 2.1 | 0.6 | 0.3 | 0.1 | 0.2 | 0.8 | 0.5 | 0.3 | 0.1 |
| E11C79 | 1.4 | 0.7 | 2.1 | 0.6 | 0.5 | 0.1 | 0.3 | 0.3 | 0.1 | 0.5 | 0.2 |
| E11C82 | 0.2 | 0.5 | 0.5 | 0.2 | 0.3 | 0.3 | 0.2 | 0.7 | 0.2 | 0.3 | 0.5 |
| E11C83 | 0.2 | 0.2 | 0.5 | 0.3 | 0.3 | 0.1 | 0.2 | 0.3 | 0.6 | 0.3 | 0.1 |
| E12C3 | 0.0 | 0.0 | 0.0 | 0.0 | 0.0 | 0.0 | 0.0 | 0.0 | 0.0 | 0.0 | 0.0 |
| E12C4 | 0.2 | 0.2 | 0.1 | 0.3 | 0.1 | 0.1 | 0.1 | 0.1 | 0.3 | 0.2 | 0.2 |
| E12C5 | 0.2 | 0.3 | 0.3 | 0.2 | 0.1 | 0.2 | 0.1 | 0.1 | 0.1 | 0.1 | 0.3 |
| E12C6 | 0.2 | 1.4 | 4.4 | 0.1 | 0.1 | 0.1 | 0.3 | 0.1 | 0.3 | 0.1 | 0.1 |
| E12C7 | 0.6 | 0.4 | 0.6 | 0.7 | 0.6 | 0.3 | 0.2 | 0.6 | 0.8 | 0.8 | 0.4 |
| E12C8 | 0.4 | 0.6 | 0.6 | 0.5 | 0.1 | 0.1 | 0.3 | 0.1 | 0.3 | 0.1 | 0.1 |
| E12C9 | 0.4 | 0.6 | 0.5 | 0.4 | 0.1 | 0.1 | 0.4 | 0.1 | 0.4 | 0.1 | 0.1 |
| E12C10 | 0.4 | 0.4 | 0.3 | 0.5 | 0.3 | 0.3 | 0.1 | 0.3 | 0.6 | 0.4 | 0.2 |
| E12C11 | 0.4 | 0.5 | 0.5 | 0.4 | 0.2 | 0.4 | 0.1 | 0.2 | 0.1 | 0.3 | 0.3 |
| E12C12 | 0.5 | 0.4 | 0.3 | 0.5 | 0.3 | 0.1 | 0.2 | 0.1 | 0.2 | 0.6 | 0.0 |
| E12C13 | 0.4 | 0.4 | 0.4 | 0.3 | 0.2 | 0.4 | 0.1 | 0.2 | 0.1 | 0.3 | 0.2 |

TABLE 2-continued

| relative transfection efficiency of 4345 kinds of compounds on Luc-mRNA of the HeLa cells | | | | | | | | | | | |
|---|---|---|---|---|---|---|---|---|---|---|---|
| | A9 | A10 | A11 | A12 | A14 | A15 | A16 | A23 | A24 | A28 | A33 |
| E12C14 | 0.4 | 0.6 | 0.4 | 0.2 | 0.4 | 0.1 | 0.1 | 0.2 | 0.1 | 0.2 | 0.1 |
| E12C56 | 0.5 | 0.3 | 0.4 | 0.4 | 0.2 | 0.1 | 0.1 | 0.5 | 0.1 | 0.3 | 0.0 |
| E12C57 | 0.4 | 0.5 | 0.7 | 0.4 | 0.2 | 0.1 | 0.1 | 0.2 | 0.2 | 0.6 | 0.1 |
| E12C58 | 0.6 | 0.8 | 0.6 | 0.7 | 0.4 | 0.2 | 0.1 | 0.2 | 0.1 | 0.3 | 0.3 |
| E12C60 | 0.4 | 0.5 | 0.7 | 0.4 | 0.2 | 0.1 | 0.2 | 0.4 | 0.1 | 0.3 | 0.2 |
| E12C62 | 0.4 | 0.5 | 0.7 | 0.4 | 0.2 | 0.4 | 0.6 | 0.2 | 0.4 | 0.3 | 0.4 |
| E12C63 | 0.3 | 0.6 | 0.4 | 0.3 | 0.3 | 0.2 | 0.1 | 0.1 | 0.1 | 0.4 | 0.0 |
| E12C64 | 0.5 | 1.9 | 0.5 | 0.4 | 0.2 | 0.3 | 0.1 | 0.2 | 0.6 | 0.3 | 0.1 |
| E12C66 | 0.8 | 2.9 | 0.7 | 0.6 | 0.2 | 0.1 | 0.1 | 0.2 | 0.4 | 0.3 | 0.0 |
| E12C67 | 0.4 | 1.5 | 0.4 | 0.3 | 0.6 | 0.1 | 0.4 | 0.6 | 0.2 | 0.1 | 0.3 |
| E12C71 | 1.9 | 0.9 | 0.5 | 0.4 | 0.1 | 0.4 | 0.1 | 0.2 | 0.3 | 0.3 | 0.1 |
| E12C72 | 2.3 | 0.9 | 0.6 | 0.5 | 0.5 | 0.1 | 0.1 | 0.1 | 0.1 | 0.3 | 0.3 |
| E12C74 | 1.9 | 0.7 | 1.5 | 0.4 | 0.2 | 0.1 | 0.1 | 0.5 | 0.4 | 0.3 | 0.0 |
| E12C79 | 1.9 | 0.8 | 1.5 | 0.4 | 0.4 | 0.1 | 0.2 | 0.2 | 0.1 | 0.5 | 0.1 |
| E12C82 | 0.1 | 0.3 | 0.3 | 0.1 | 0.2 | 0.2 | 0.1 | 0.3 | 0.1 | 0.1 | 0.2 |
| E12C83 | 0.1 | 0.1 | 0.3 | 0.2 | 0.1 | 0.0 | 0.1 | 0.1 | 0.3 | 0.1 | 0.0 |
| E13C3 | 0.2 | 0.3 | 0.3 | 0.2 | 0.1 | 0.1 | 0.2 | 0.1 | 0.2 | 0.1 | 0.1 |
| E13C4 | 0.4 | 0.4 | 0.3 | 0.5 | 0.3 | 0.3 | 0.1 | 0.3 | 0.6 | 0.4 | 0.4 |
| E13C5 | 1.4 | 1.4 | 3.8 | 0.4 | 0.2 | 0.4 | 0.1 | 0.2 | 0.1 | 0.3 | 0.6 |
| E13C6 | 0.2 | 0.8 | 0.6 | 0.1 | 0.1 | 0.1 | 0.3 | 0.1 | 0.3 | 0.1 | 0.1 |
| E13C7 | 0.6 | 0.4 | 0.6 | 0.7 | 0.6 | 0.3 | 0.2 | 0.6 | 0.8 | 0.8 | 0.8 |
| E13C8 | 0.4 | 0.6 | 0.6 | 0.5 | 0.1 | 0.1 | 0.3 | 0.1 | 0.3 | 0.1 | 0.1 |
| E13C9 | 0.4 | 0.6 | 0.5 | 0.4 | 0.2 | 0.2 | 0.8 | 0.2 | 0.8 | 0.3 | 0.3 |
| E13C10 | 0.4 | 0.4 | 0.3 | 0.5 | 0.6 | 0.6 | 0.2 | 0.6 | 0.4 | 0.8 | 0.8 |
| E13C11 | 0.4 | 0.5 | 0.5 | 0.4 | 0.4 | 0.8 | 0.2 | 0.4 | 0.2 | 0.5 | 0.3 |
| E13C12 | 0.5 | 0.4 | 0.3 | 0.5 | 0.6 | 0.3 | 0.5 | 0.3 | 0.5 | 0.9 | 0.2 |
| E13C13 | 0.4 | 0.4 | 0.4 | 0.3 | 0.4 | 0.7 | 0.2 | 0.4 | 0.2 | 0.5 | 0.6 |
| E13C14 | 0.4 | 0.6 | 0.4 | 0.3 | 0.8 | 0.2 | 0.1 | 0.4 | 0.1 | 0.3 | 0.3 |
| E13C56 | 0.5 | 0.3 | 0.4 | 0.4 | 0.4 | 0.1 | 0.2 | 0.7 | 0.2 | 0.5 | 0.2 |
| E13C57 | 0.4 | 0.5 | 0.7 | 0.4 | 0.4 | 0.2 | 0.1 | 0.5 | 0.4 | 0.9 | 0.5 |
| E13C58 | 0.6 | 0.8 | 0.6 | 0.7 | 0.8 | 0.5 | 0.2 | 0.4 | 0.2 | 0.5 | 0.6 |
| E13C60 | 0.4 | 0.5 | 0.7 | 0.4 | 0.4 | 0.3 | 0.4 | 0.8 | 0.2 | 0.5 | 0.8 |
| E13C62 | 0.4 | 2.5 | 0.7 | 0.4 | 0.4 | 0.8 | 0.6 | 0.4 | 0.7 | 0.5 | 0.9 |
| E13C63 | 0.3 | 3.8 | 0.4 | 0.3 | 0.6 | 0.4 | 0.2 | 0.2 | 0.2 | 0.8 | 0.2 |
| E13C64 | 0.5 | 1.9 | 0.5 | 0.4 | 0.4 | 0.6 | 0.2 | 0.4 | 0.8 | 0.5 | 0.5 |
| E13C66 | 0.8 | 2.5 | 0.7 | 0.6 | 0.2 | 0.1 | 0.1 | 0.2 | 0.4 | 0.3 | 0.1 |
| E13C67 | 0.4 | 2.9 | 3.4 | 0.3 | 0.6 | 0.1 | 0.4 | 0.6 | 0.2 | 0.1 | 0.6 |
| E13C71 | 0.5 | 2.5 | 0.5 | 0.4 | 0.1 | 0.4 | 0.1 | 0.2 | 0.3 | 0.3 | 0.2 |
| E13C72 | 0.6 | 0.8 | 0.6 | 0.5 | 0.5 | 0.1 | 0.5 | 0.7 | 0.1 | 0.3 | 0.7 |
| E13C74 | 0.3 | 0.4 | 0.1 | 0.2 | 0.1 | 0.0 | 0.1 | 0.3 | 0.2 | 0.1 | 0.0 |
| E13C79 | 0.3 | 0.3 | 0.4 | 0.2 | 0.2 | 0.0 | 0.6 | 0.1 | 0.0 | 0.3 | 0.1 |
| E13C82 | 0.1 | 0.3 | 0.3 | 0.1 | 0.2 | 0.2 | 0.1 | 0.3 | 0.1 | 0.1 | 0.2 |
| E13C83 | 0.1 | 0.1 | 0.3 | 0.2 | 0.1 | 0.0 | 0.1 | 0.1 | 0.3 | 0.1 | 0.0 |
| E15C10 | 0.4 | 0.8 | 0.8 | 0.2 | 0.2 | 0.2 | 0.4 | 0.2 | 0.4 | 0.2 | 0.2 |
| E15C11 | 0.2 | 0.4 | 0.8 | 0.4 | 0.6 | 0.2 | 0.4 | 0.6 | 0.4 | 0.6 | 0.2 |
| E15C12 | 0.2 | 0.2 | 0.6 | 0.2 | 0.2 | 0.4 | 0.2 | 0.6 | 0.2 | 0.4 | 0.4 |
| E15C13 | 0.5 | 0.8 | 0.4 | 0.8 | 0.7 | 0.2 | 0.4 | 0.6 | 0.4 | 0.6 | 0.2 |
| E15C14 | 0.8 | 0.4 | 0.6 | 0.6 | 0.6 | 0.4 | 0.2 | 0.8 | 0.6 | 0.4 | 0.6 |
| E15C56 | 0.4 | 0.3 | 0.6 | 0.4 | 0.1 | 0.2 | 0.4 | 0.6 | 0.4 | 0.6 | 0.2 |
| E15C57 | 0.2 | 0.7 | 0.2 | 0.5 | 0.6 | 0.2 | 0.6 | 0.2 | 0.7 | 0.6 | 0.2 |
| E15C58 | 0.7 | 0.6 | 0.7 | 0.2 | 0.6 | 0.2 | 0.7 | 0.6 | 0.2 | 0.6 | 0.2 |
| E15C60 | 0.0 | 0.2 | 0.7 | 0.2 | 0.2 | 0.6 | 0.4 | 0.4 | 0.4 | 0.2 | 0.2 |
| E15C62 | 0.0 | 0.0 | 0.5 | 0.0 | 0.6 | 0.5 | 0.9 | 0.6 | 0.4 | 0.6 | 0.6 |
| E15C63 | 0.0 | 0.0 | 0.2 | 0.0 | 0.3 | 0.5 | 0.3 | 0.8 | 0.8 | 0.6 | 0.2 |
| E15C64 | 0.2 | 0.2 | 0.7 | 0.2 | 0.6 | 0.2 | 0.2 | 0.6 | 0.6 | 0.2 | 0.2 |
| E15C66 | 0.2 | 0.2 | 1.4 | 0.5 | 0.4 | 0.4 | 0.4 | 0.6 | 0.4 | 0.6 | 0.2 |
| E15C67 | 0.2 | 0.7 | 1.0 | 0.5 | 0.6 | 0.2 | 0.4 | 0.6 | 0.4 | 0.6 | 0.2 |
| E15C71 | 0.0 | 0.5 | 0.5 | 0.0 | 0.9 | 0.8 | 0.4 | 0.8 | 0.4 | 0.6 | 0.2 |
| E15C72 | 0.5 | 0.2 | 0.7 | 0.2 | 0.6 | 0.2 | 0.6 | 0.6 | 0.2 | 0.8 | 0.2 |
| E15C74 | 0.7 | 1.0 | 0.2 | 0.5 | 0.8 | 0.5 | 0.7 | 0.6 | 0.4 | 0.6 | 0.2 |
| E15C79 | 0.8 | 1.2 | 4.6 | 3.8 | 0.6 | 0.5 | 0.3 | 0.6 | 0.4 | 0.6 | 0.2 |
| E15C82 | 0.2 | 0.6 | 0.6 | 0.2 | 0.6 | 0.5 | 0.9 | 0.6 | 0.4 | 0.6 | 0.2 |
| E15C83 | 0.2 | 0.2 | 0.6 | 0.4 | 0.2 | 0.2 | 0.4 | 0.6 | 0.4 | 0.6 | 0.2 |
| E17C3 | 0.1 | 0.2 | 0.1 | 0.2 | 0.2 | 0.2 | 0.1 | 0.2 | 0.1 | 0.2 | 0.2 |
| E17C4 | 0.1 | 0.1 | 0.2 | 0.1 | 0.2 | 0.2 | 0.1 | 0.2 | 0.1 | 0.1 | 0.3 |
| E17C5 | 0.1 | 0.2 | 0.2 | 0.7 | 0.4 | 0.3 | 0.2 | 0.2 | 0.1 | 0.2 | 0.2 |
| E17C6 | 0.2 | 0.2 | 0.2 | 0.6 | 0.2 | 0.5 | 0.1 | 0.1 | 0.2 | 0.1 | 0.2 |
| E17C7 | 0.1 | 0.3 | 0.5 | 0.6 | 0.4 | 0.6 | 0.1 | 0.2 | 0.4 | 0.2 | 0.2 |
| E17C8 | 0.1 | 0.2 | 0.2 | 0.4 | 0.2 | 0.9 | 0.2 | 0.2 | 0.1 | 0.1 | 0.1 |
| E17C9 | 0.1 | 0.2 | 0.2 | 0.3 | 0.5 | 0.6 | 0.4 | 0.3 | 0.2 | 0.0 | 0.2 |
| E17C10 | 0.3 | 0.2 | 0.3 | 0.4 | 0.2 | 0.4 | 0.2 | 0.4 | 0.2 | 0.1 | 0.4 |
| E17C11 | 0.3 | 0.5 | 0.3 | 0.4 | 0.2 | 0.2 | 0.4 | 0.8 | 0.4 | 0.7 | 0.4 |
| E17C12 | 0.4 | 0.4 | 0.2 | 0.7 | 0.4 | 0.1 | 0.8 | 0.6 | 0.4 | 0.8 | 0.8 |
| E17C13 | 0.1 | 0.5 | 0.3 | 0.4 | 0.9 | 0.2 | 0.4 | 0.4 | 0.8 | 0.3 | 0.5 |
| E17C14 | 0.4 | 0.3 | 0.2 | 0.4 | 0.2 | 0.8 | 0.4 | 0.7 | 0.9 | 0.7 | 0.3 |

TABLE 2-continued

| relative transfection efficiency of 4345 kinds of compounds on Luc-mRNA of the HeLa cells | | | | | | | | | | | |
|---|---|---|---|---|---|---|---|---|---|---|---|
| | A9 | A10 | A11 | A12 | A14 | A15 | A16 | A23 | A24 | A28 | A33 |
| E17C56 | 0.1 | 0.2 | 0.4 | 0.3 | 0.2 | 0.8 | 0.8 | 0.9 | 0.4 | 0.2 | 0.2 |
| E17C57 | 0.1 | 0.4 | 0.2 | 0.2 | 0.4 | 0.8 | 0.5 | 0.3 | 0.8 | 0.1 | 0.4 |
| E17C58 | 0.1 | 0.4 | 0.2 | 0.4 | 0.8 | 0.4 | 0.4 | 0.9 | 0.4 | 0.2 | 0.4 |
| E17C60 | 0.4 | 0.2 | 0.4 | 0.2 | 0.4 | 0.4 | 0.4 | 0.8 | 0.4 | 0.1 | 0.4 |
| E17C62 | 0.7 | 0.4 | 0.5 | 0.3 | 0.4 | 0.4 | 0.7 | 0.4 | 0.8 | 0.9 | 0.2 |
| E17C63 | 0.4 | 0.2 | 0.3 | 0.2 | 0.7 | 0.8 | 0.9 | 0.4 | 0.8 | 0.7 | 0.2 |
| E17C64 | 0.4 | 0.2 | 0.2 | 0.4 | 0.4 | 0.5 | 0.8 | 0.9 | 0.4 | 0.2 | 0.2 |
| E17C66 | 0.6 | 0.4 | 2.2 | 1.2 | 0.4 | 0.4 | 0.2 | 0.4 | 0.8 | 0.1 | 0.4 |
| E17C67 | 1.9 | 0.3 | 2.0 | 0.8 | 0.1 | 0.2 | 0.2 | 0.4 | 0.2 | 0.1 | 0.4 |
| E17C71 | 2.8 | 1.6 | 2.3 | 0.6 | 0.1 | 0.4 | 0.2 | 0.4 | 0.2 | 0.8 | 0.4 |
| E17C72 | 3.3 | 2.7 | 4.3 | 1.5 | 0.4 | 0.2 | 0.4 | 0.2 | 0.4 | 0.2 | 0.2 |
| E17C74 | 0.4 | 0.4 | 0.8 | 0.1 | 0.7 | 0.4 | 0.5 | 0.3 | 0.4 | 0.2 | 0.2 |
| E17C79 | 0.2 | 0.4 | 0.3 | 0.2 | 0.4 | 0.2 | 0.3 | 0.2 | 0.7 | 0.4 | 0.2 |
| E17C82 | 0.2 | 0.1 | 0.1 | 0.2 | 0.2 | 0.2 | 0.1 | 0.2 | 0.1 | 0.2 | 0.1 |
| E17C83 | 0.2 | 0.1 | 0.2 | 0.4 | 0.1 | 0.7 | 0.4 | 0.5 | 0.3 | 0.4 | 0.1 |
| E18C3 | 0.1 | 0.1 | 0.2 | 0.1 | 0.1 | 0.3 | 0.4 | 0.6 | 0.4 | 0.6 | 0.1 |
| E18C4 | 0.1 | 0.1 | 0.2 | 0.0 | 0.2 | 0.2 | 0.6 | 0.6 | 0.4 | 0.6 | 0.1 |
| E18C5 | 0.4 | 0.4 | 0.8 | 0.1 | 0.4 | 0.3 | 0.9 | 0.1 | 0.7 | 0.4 | 0.2 |
| E18C6 | 0.1 | 0.2 | 0.3 | 0.4 | 0.4 | 0.8 | 0.8 | 0.3 | 0.9 | 0.1 | 0.4 |
| E18C7 | 0.4 | 0.5 | 0.3 | 0.2 | 0.3 | 0.2 | 0.3 | 0.4 | 0.4 | 0.1 | 0.4 |
| E18C8 | 0.1 | 0.4 | 0.2 | 0.5 | 0.3 | 0.5 | 0.3 | 0.2 | 0.8 | 0.2 | 0.7 |
| E18C9 | 0.1 | 0.5 | 0.3 | 0.1 | 0.4 | 0.4 | 0.2 | 0.5 | 0.3 | 0.1 | 0.4 |
| E18C10 | 0.1 | 0.3 | 0.2 | 0.4 | 0.4 | 0.5 | 0.3 | 0.4 | 0.2 | 0.4 | 0.4 |
| E18C11 | 0.2 | 0.2 | 0.4 | 0.2 | 0.3 | 0.3 | 0.2 | 0.5 | 0.3 | 0.3 | 0.5 |
| E18C12 | 0.1 | 0.4 | 0.2 | 0.5 | 0.3 | 0.2 | 0.4 | 0.3 | 0.2 | 0.4 | 0.4 |
| E18C13 | 0.4 | 0.4 | 0.2 | 0.4 | 0.2 | 0.4 | 0.2 | 0.2 | 0.4 | 0.1 | 0.5 |
| E18C14 | 0.2 | 0.7 | 0.4 | 0.5 | 0.6 | 0.9 | 0.4 | 0.7 | 0.6 | 0.7 | 0.3 |
| E18C56 | 0.2 | 0.4 | 0.2 | 0.3 | 0.4 | 0.3 | 0.8 | 0.9 | 0.4 | 0.2 | 0.2 |
| E18C57 | 0.2 | 0.4 | 0.2 | 0.2 | 0.8 | 0.9 | 0.7 | 0.8 | 0.8 | 0.1 | 0.4 |
| E18C58 | 0.3 | 0.2 | 0.3 | 0.4 | 0.4 | 0.8 | 0.4 | 0.9 | 0.4 | 0.2 | 0.4 |
| E18C60 | 0.3 | 0.5 | 0.3 | 0.4 | 0.6 | 0.2 | 0.4 | 0.8 | 0.4 | 0.5 | 0.4 |
| E18C62 | 0.4 | 0.4 | 0.2 | 0.7 | 0.8 | 0.1 | 0.8 | 0.6 | 0.4 | 0.8 | 0.8 |
| E18C63 | 0.1 | 0.5 | 0.3 | 0.4 | 0.4 | 0.2 | 0.4 | 0.4 | 0.8 | 0.3 | 0.5 |
| E18C64 | 0.4 | 0.3 | 0.2 | 0.4 | 0.3 | 0.8 | 0.4 | 0.7 | 0.4 | 0.7 | 0.3 |
| E18C66 | 0.1 | 0.2 | 0.4 | 0.3 | 0.4 | 0.8 | 0.8 | 0.9 | 0.4 | 0.2 | 0.2 |
| E18C67 | 0.2 | 1.5 | 0.7 | 0.2 | 0.4 | 0.4 | 0.8 | 0.7 | 0.4 | 0.1 | 0.4 |
| E18C71 | 0.5 | 1.8 | 0.7 | 0.4 | 0.8 | 0.2 | 0.2 | 0.4 | 0.2 | 0.1 | 0.4 |
| E18C72 | 1.8 | 0.7 | 1.8 | 0.2 | 0.4 | 0.2 | 0.2 | 0.4 | 0.2 | 0.8 | 0.4 |
| E18C74 | 2.8 | 1.7 | 1.9 | 0.3 | 0.4 | 0.2 | 0.4 | 0.2 | 0.4 | 0.6 | 0.2 |
| E18C79 | 1.7 | 0.7 | 1.3 | 0.2 | 0.9 | 0.8 | 0.9 | 0.4 | 0.8 | 0.6 | 0.4 |
| E18C82 | 0.2 | 0.1 | 0.1 | 0.2 | 0.4 | 0.8 | 0.4 | 0.4 | 0.2 | 0.1 | 0.2 |
| E18C83 | 0.1 | 0.2 | 0.2 | 0.1 | 0.4 | 0.2 | 0.8 | 0.7 | 0.4 | 0.1 | 0.4 |
| E20C9 | 1.4 | 2.2 | 2.1 | 0.9 | 0.1 | 0.1 | 0.4 | 0.1 | 0.4 | 0.1 | 0.1 |
| E20C10 | 1.7 | 1.7 | 1.1 | 1.1 | 0.3 | 0.3 | 0.1 | 0.3 | 0.6 | 0.4 | 0.4 |
| E20C11 | 1.4 | 2.2 | 2.1 | 0.9 | 0.2 | 0.4 | 0.1 | 0.2 | 0.1 | 0.3 | 0.6 |
| E20C12 | 2.2 | 1.7 | 1.1 | 0.9 | 0.6 | 0.3 | 0.5 | 0.3 | 0.5 | 0.6 | 0.1 |
| E20C13 | 0.2 | 0.2 | 0.2 | 0.3 | 0.4 | 0.7 | 0.2 | 0.4 | 0.2 | 0.3 | 0.3 |
| E20C14 | 0.4 | 0.6 | 0.4 | 0.3 | 0.8 | 0.2 | 0.1 | 0.4 | 0.1 | 0.2 | 0.2 |
| E20C56 | 0.5 | 0.3 | 0.4 | 0.2 | 0.4 | 0.1 | 0.9 | 0.7 | 0.2 | 0.3 | 0.1 |
| E20C57 | 0.4 | 0.5 | 0.7 | 0.4 | 0.2 | 0.1 | 0.1 | 0.2 | 0.2 | 0.6 | 0.3 |
| E20C58 | 0.6 | 0.8 | 0.6 | 0.7 | 0.4 | 0.2 | 0.1 | 0.2 | 0.1 | 0.3 | 0.6 |
| E20C60 | 0.4 | 0.5 | 0.7 | 0.9 | 0.4 | 0.3 | 0.4 | 0.8 | 0.2 | 0.4 | 0.4 |
| E20C62 | 0.4 | 0.7 | 0.7 | 0.8 | 0.4 | 0.8 | 0.5 | 0.4 | 0.7 | 0.5 | 0.8 |
| E20C63 | 2.5 | 0.4 | 0.4 | 0.7 | 0.6 | 0.4 | 0.2 | 0.2 | 0.2 | 0.8 | 0.1 |
| E20C64 | 3.8 | 0.3 | 0.5 | 0.8 | 0.4 | 0.6 | 0.2 | 0.4 | 0.5 | 0.5 | 0.3 |
| E20C66 | 1.9 | 0.7 | 0.7 | 0.5 | 0.4 | 0.1 | 0.2 | 0.5 | 0.7 | 0.5 | 0.1 |
| E20C67 | 2.5 | 0.6 | 0.9 | 0.6 | 0.5 | 0.1 | 0.7 | 0.9 | 0.4 | 0.2 | 0.6 |
| E20C71 | 2.9 | 0.9 | 0.5 | 0.8 | 0.2 | 0.7 | 0.2 | 0.4 | 0.6 | 0.5 | 0.2 |
| E20C72 | 2.5 | 0.8 | 0.6 | 0.9 | 0.6 | 0.1 | 0.2 | 0.2 | 0.2 | 0.4 | 0.7 |
| E20C74 | 0.3 | 0.4 | 0.1 | 0.8 | 0.4 | 0.1 | 0.2 | 0.7 | 0.7 | 0.5 | 0.1 |
| E20C79 | 0.3 | 0.3 | 0.4 | 0.8 | 0.7 | 0.1 | 0.4 | 0.4 | 0.1 | 0.7 | 0.2 |
| E20C82 | 0.1 | 0.3 | 0.3 | 0.2 | 0.3 | 0.3 | 0.2 | 0.7 | 0.2 | 0.3 | 0.5 |
| E20C83 | 0.1 | 0.1 | 0.3 | 0.3 | 0.3 | 0.1 | 0.2 | 0.3 | 0.6 | 0.3 | 0.1 |
| E21C9 | 0.2 | 0.3 | 0.3 | 0.2 | 0.1 | 0.1 | 0.2 | 0.1 | 0.2 | 0.1 | 0.1 |
| E21C10 | 0.2 | 0.2 | 0.1 | 0.3 | 0.1 | 0.1 | 0.1 | 0.3 | 0.6 | 0.4 | 0.2 |
| E21C11 | 1.4 | 2.2 | 2.1 | 0.4 | 0.2 | 0.4 | 0.1 | 0.2 | 0.1 | 0.3 | 0.3 |
| E21C12 | 2.2 | 1.7 | 1.1 | 0.5 | 0.3 | 0.1 | 0.2 | 0.1 | 0.2 | 0.6 | 0.0 |
| E21C13 | 1.4 | 1.6 | 1.5 | 0.3 | 0.2 | 0.4 | 0.1 | 0.2 | 0.1 | 0.3 | 0.2 |
| E21C14 | 1.7 | 2.2 | 1.5 | 0.3 | 0.8 | 0.2 | 0.1 | 0.2 | 0.1 | 0.2 | 0.2 |
| E21C56 | 0.5 | 0.3 | 0.4 | 0.4 | 0.4 | 0.1 | 0.2 | 0.5 | 0.1 | 0.3 | 0.1 |
| E21C57 | 0.4 | 0.5 | 0.7 | 0.4 | 0.4 | 0.2 | 0.2 | 0.5 | 0.4 | 0.7 | 0.5 |

TABLE 2-continued relative transfection efficiency of 4345 kinds of compounds on Luc-mRNA of the HeLa cells

| | A9 | A10 | A11 | A12 | A14 | A15 | A16 | A23 | A24 | A28 | A33 |
|---|---|---|---|---|---|---|---|---|---|---|---|
| E21C58 | 0.6 | 0.8 | 0.6 | 0.7 | 0.8 | 0.5 | 0.5 | 0.4 | 0.2 | 0.5 | 0.4 |
| E21C60 | 0.2 | 0.3 | 0.7 | 0.4 | 0.4 | 0.1 | 0.4 | 0.8 | 0.2 | 0.4 | 0.8 |
| E21C62 | 1.2 | 0.6 | 0.7 | 0.4 | 0.4 | 0.4 | 0.7 | 0.4 | 0.7 | 0.5 | 0.3 |
| E21C63 | 1.9 | 0.9 | 0.4 | 0.3 | 0.6 | 0.2 | 0.2 | 0.2 | 0.2 | 0.8 | 0.2 |
| E21C64 | 0.9 | 0.9 | 0.5 | 0.2 | 0.8 | 0.7 | 0.2 | 0.4 | 0.4 | 0.5 | 0.5 |
| E21C66 | 1.2 | 0.7 | 0.4 | 0.8 | 0.5 | 0.2 | 0.2 | 0.5 | 0.7 | 0.3 | 0.2 |
| E21C67 | 1.5 | 0.8 | 0.7 | 0.4 | 0.8 | 0.2 | 0.7 | 0.8 | 0.4 | 0.2 | 0.2 |
| E21C71 | 1.2 | 0.5 | 0.2 | 0.5 | 0.3 | 0.9 | 0.2 | 0.4 | 0.6 | 0.5 | 0.4 |
| E21C72 | 0.3 | 0.4 | 0.3 | 0.6 | 0.7 | 0.2 | 0.2 | 0.2 | 0.2 | 0.4 | 0.9 |
| E21C74 | 0.5 | 0.8 | 0.2 | 0.4 | 0.4 | 0.1 | 0.2 | 0.9 | 0.7 | 0.5 | 0.2 |
| E21C79 | 0.5 | 0.6 | 0.8 | 0.4 | 0.4 | 0.1 | 0.2 | 0.2 | 0.1 | 0.5 | 0.2 |
| E21C82 | 0.2 | 0.5 | 0.5 | 0.2 | 0.3 | 0.3 | 0.1 | 0.3 | 0.1 | 0.1 | 0.2 |
| E21C83 | 0.2 | 0.2 | 0.5 | 0.3 | 0.3 | 0.1 | 0.1 | 0.1 | 0.3 | 0.1 | 0.0 |
| E24C9 | 0.2 | 0.3 | 0.3 | 0.2 | 0.1 | 0.1 | 0.2 | 0.1 | 0.2 | 0.1 | 0.1 |
| E24C10 | 0.2 | 0.2 | 0.1 | 0.3 | 0.1 | 0.4 | 0.2 | 0.7 | 0.6 | 0.4 | 0.2 |
| E24C11 | 0.5 | 0.8 | 0.8 | 0.2 | 0.1 | 0.4 | 0.1 | 0.5 | 0.1 | 0.3 | 0.3 |
| E24C12 | 0.8 | 0.6 | 0.4 | 0.2 | 0.1 | 0.1 | 0.2 | 0.4 | 0.2 | 0.6 | 0.0 |
| E24C13 | 0.6 | 0.6 | 0.6 | 0.3 | 0.2 | 0.9 | 0.1 | 0.5 | 0.1 | 0.3 | 0.2 |
| E24C14 | 0.6 | 0.9 | 0.6 | 0.3 | 0.4 | 0.3 | 0.1 | 0.2 | 0.0 | 0.1 | 0.1 |
| E24C56 | 0.2 | 0.1 | 0.2 | 0.4 | 0.2 | 0.2 | 0.1 | 0.6 | 0.1 | 0.1 | 0.0 |
| E24C57 | 0.2 | 0.2 | 0.3 | 0.4 | 0.2 | 0.1 | 0.0 | 0.2 | 0.2 | 0.6 | 0.3 |
| E24C58 | 0.6 | 0.3 | 0.2 | 0.7 | 0.4 | 0.2 | 0.1 | 0.2 | 0.1 | 0.3 | 0.6 |
| E24C60 | 0.2 | 0.1 | 0.1 | 0.2 | 0.2 | 0.2 | 0.2 | 0.4 | 0.1 | 0.3 | 0.4 |
| E24C62 | 0.2 | 0.5 | 0.3 | 0.5 | 0.2 | 0.5 | 0.6 | 0.2 | 0.4 | 0.3 | 0.8 |
| E24C63 | 0.2 | 0.7 | 0.2 | 0.4 | 0.4 | 0.2 | 0.1 | 0.1 | 0.1 | 0.4 | 0.1 |
| E24C64 | 0.3 | 0.4 | 0.2 | 0.5 | 0.2 | 0.4 | 0.1 | 0.2 | 0.6 | 0.3 | 0.3 |
| E24C66 | 0.4 | 0.5 | 0.1 | 0.3 | 0.2 | 0.1 | 0.1 | 0.2 | 0.4 | 0.3 | 0.1 |
| E24C67 | 0.2 | 0.6 | 0.7 | 0.1 | 0.7 | 0.1 | 0.9 | 0.6 | 0.2 | 0.1 | 0.6 |
| E24C71 | 0.3 | 0.5 | 0.1 | 0.1 | 0.2 | 0.5 | 0.3 | 0.2 | 0.3 | 0.3 | 0.2 |
| E24C72 | 0.3 | 0.2 | 0.1 | 0.1 | 0.7 | 0.1 | 0.3 | 0.1 | 0.1 | 0.3 | 0.7 |
| E24C74 | 0.5 | 0.3 | 0.1 | 0.2 | 0.5 | 0.2 | 0.3 | 0.5 | 0.4 | 0.3 | 0.1 |
| E24C79 | 0.5 | 0.2 | 0.3 | 0.2 | 0.9 | 0.2 | 0.5 | 0.2 | 0.1 | 0.5 | 0.2 |
| E24C82 | 0.4 | 0.5 | 0.5 | 0.2 | 0.9 | 0.8 | 0.2 | 0.3 | 0.1 | 0.1 | 0.2 |
| E24C83 | 0.4 | 0.2 | 0.5 | 0.3 | 0.7 | 0.2 | 0.2 | 0.1 | 0.3 | 0.1 | 0.0 |
| Lip3000 | | | | | | 1.0 | | | | | |

Embodiment 13: Transfection of Lipid Nanoparticles Prepared from Amino Compounds on BMDC Primary Cells Preparation method: the same as that described in Embodiment 7.

Animal preparation: 6-week-old female C57BL/6 mice with the body weight about 20 g were selected. The feeding environment was an SPF stage feeding room. Animal tests were strictly performed according to the guide of the national health institute and the animal ethics requirements.

Cell acquisition: C57BL/6 mice were killed through cervical dislocation, and were soaked for 5 min in 75% ethyl alcohol. Dissection was performed to obtain thigh and calf tibiae of the mice. Attached muscles were removed to expose sclerotin. Then, bone marrow in tibiae was blown out by using a 1 mL injector sucked with PBS. After the bone marrow was blown away, impurities were filtered away by a 50 μm filter screen. A red blood cell lysis buffer (3-4 mL) was added into an obtained filtrate. Then, after placement for 5 min, 800 g centrifugation was performed for 5 min to remove the supernatant. The obtained cells were placed into a 1640 culture medium (containing 10% fetal calf serum, 20 ng/mL GMCSF and 10 ng/ml IL4) to be resuspended, and were inoculated into a 6-well plate at an inoculation density of 100000 cells/ml culture medium. The materials were placed into a 37° C. cell incubator containing 5% $CO_2$. Half liquid change was performed once every 2 days. Suspended cells and loose wall attached cells were collected on the seventh day, and were per well, and the volume of a culture medium was 100 μL.

Cell transfection: lipid nanoparticles coated with luciferase mRNA were added into a 96-well all-white ELISA plate laid with primary cells. The adding volume of the mRNA lipid nanoparticles in each well was controlled to be 10 μL. Then, the materials were put into a 37° C. incubator containing 5% $CO_2$ for 16 h.

Transfection efficiency detection: 20 μL of a substrate ONE-Glo™ Luciferase was added into each well of a 96-well all-white ELISA plate. After 1 min, detection was performed by a multifunctional or multimode microplate reader. The expression intensity of the LucmRNA transfection of representative amino lipid compounds on BMDC was as shown in Table 3. DLin-MC3 was used as a control, a plurality of amino lipids had similar expression intensity to MC3, and a plurality of amino lipids had the expression intensity obviously superior to that of the positive control.

TABLE 3
Transfection expression intensity of 98 amino lipid compounds on BMDC
| Serial number | Serial number of amino lipid | Structure | Fluorescence intensity |
| --- | --- | --- | --- |
| 1 | E3C 79A10 | 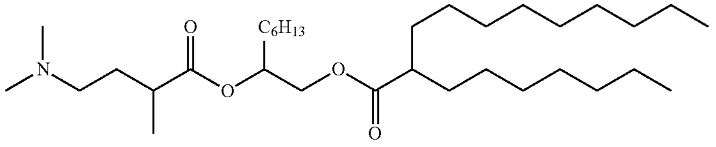 | 7.4E+04 |
| 2 | E3C 79A11 | 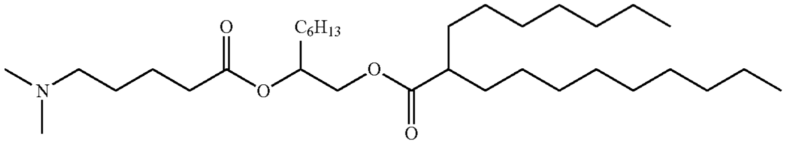 | 9.0E+04 |
| 3 | E3C 79A12 | 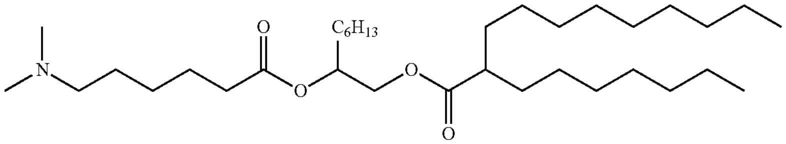 | 6.7E+04 |
| 4 | E4C 72A11 | 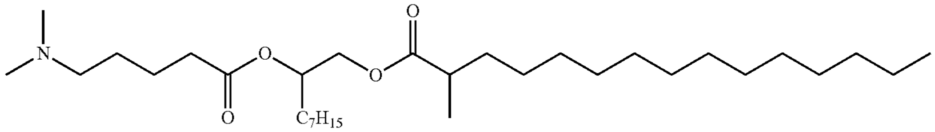 | 5.8E+04 |
| 5 | E4C 74A9 | 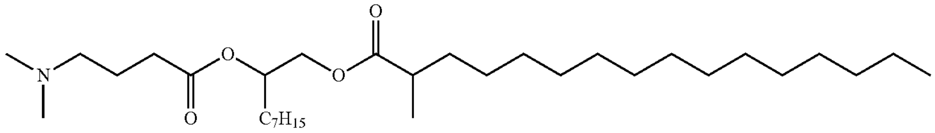 | 6.9E+04 |
| 6 | E4C 74A10 | 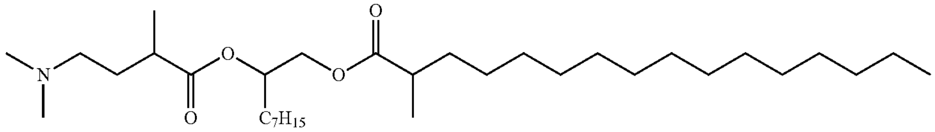 | 4.7E+04 |
| 7 | E4C 74A11 | 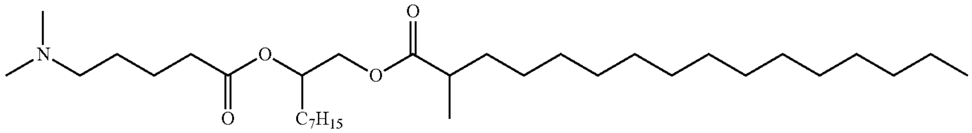 | 6.0E+04 |
| 8 | E4C 79A9 | 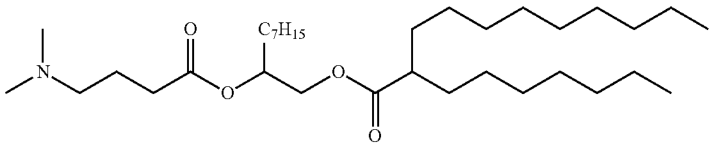 | 2.2E+04 |
| 9 | E4C 79A10 | 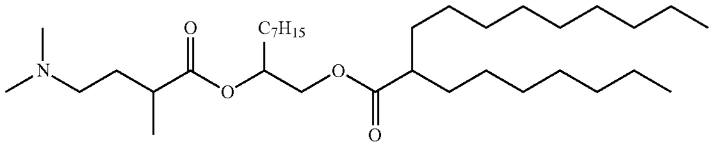 | 1.3E+04 |

TABLE 3-continued
Transfection expression intensity of 98 amino lipid compounds on BMDC
| Serial number | Serial number of amino lipid | Structure | Fluorescence intensity |
|---|---|---|---|
| 10 | E4C 79A11 | 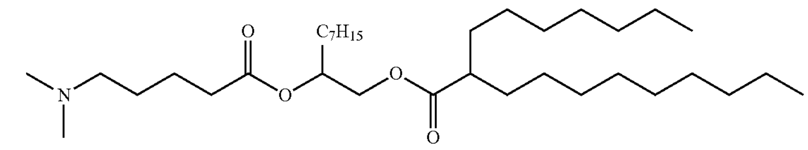 | 3.4E+04 |
| 11 | E4C 79A12 | 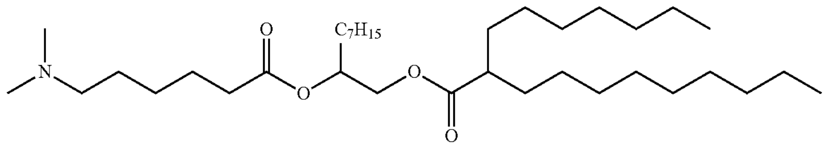 | 2.5E+04 |
| 12 | E5C 13A12 | 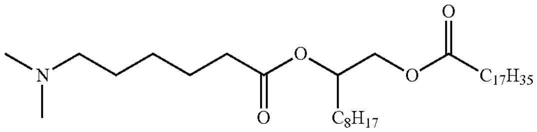 | 1.1E+04 |
| 13 | E5C 71A11 | 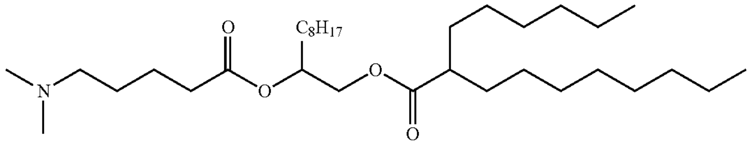 | 4.6E+04 |
| 14 | E5C 74A10 | 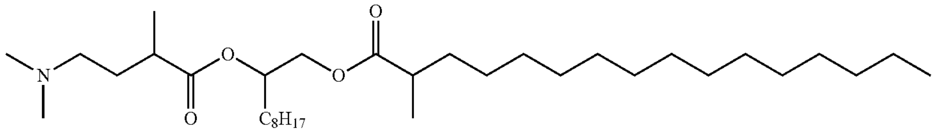 | 2.9E+04 |
| 15 | E5C 74A11 | 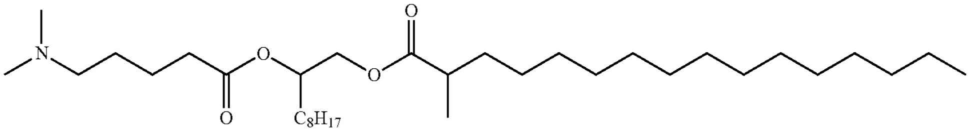 | 7.7E+03 |
| 16 | E5C 79A11 | 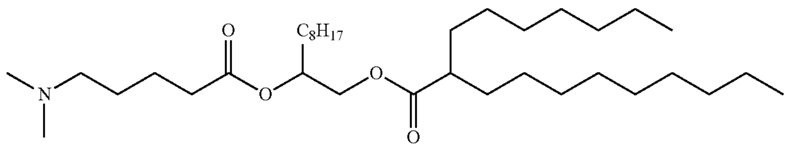 | 3.6E+04 |
| 17 | E5C 82A23 | 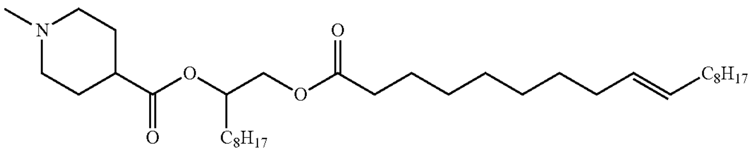 | 1.4E+04 |
| 18 | E6C 71A11 | 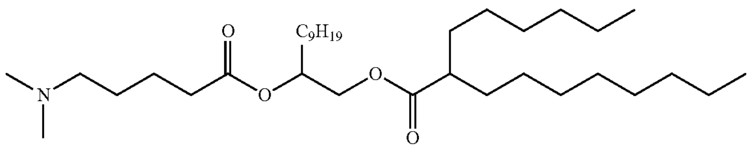 | 3.4E+04 |

TABLE 3-continued
Transfection expression intensity of 98 amino lipid compounds on BMDC
| Serial number | Serial number of amino lipid | Structure | Fluorescence intensity |
|---|---|---|---|
| 19 | E6C 71A12 | 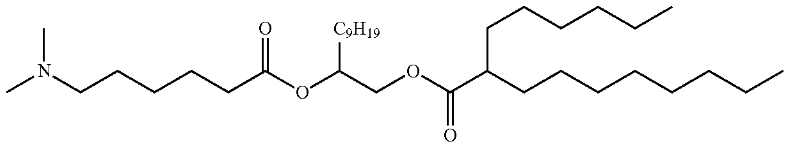 | 7.3E+04 |
| 20 | E6C 72A11 | 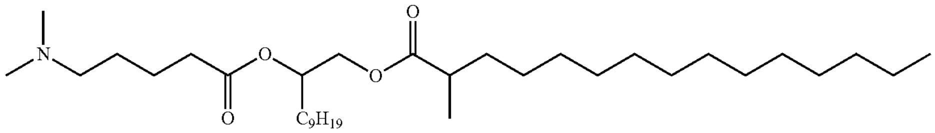 | 5.0E+04 |
| 21 | E6C 74A10 | 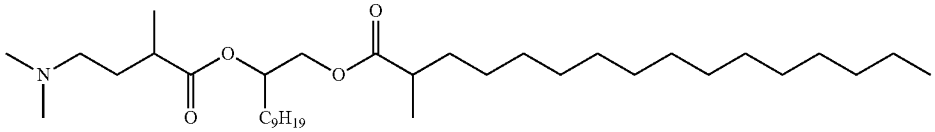 | 1.1E+04 |
| 22 | E6C 74A11 | 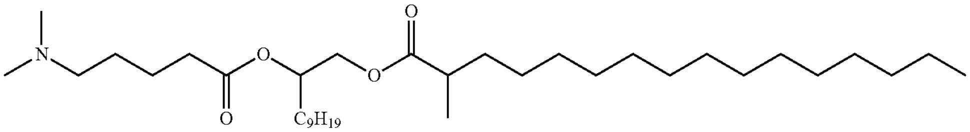 | 4.5E+04 |
| 23 | E6C 79A10 | 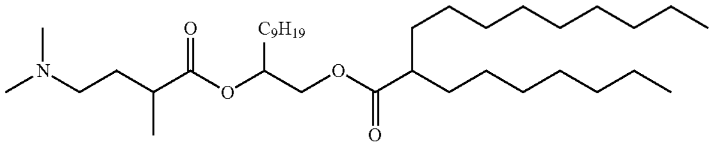 | 4.6E+04 |
| 24 | E6C 79A11 | 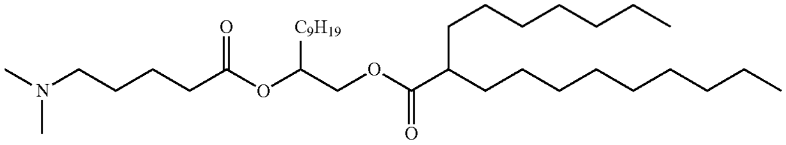 | 5.4E+04 |
| 25 | E6C 79A12 | 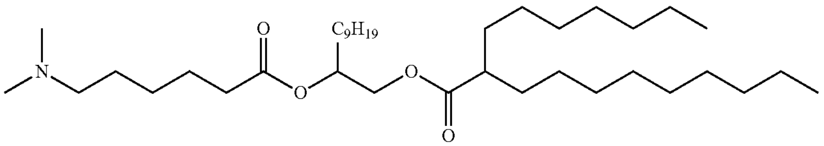 | 2.5E+04 |
| 26 | E7C 71A9 | 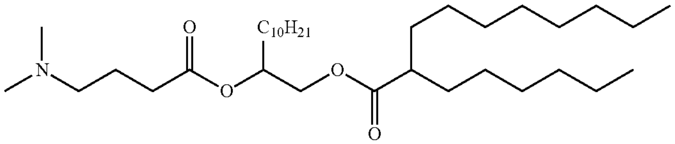 | 8.8E+04 |
| 27 | E7C 71A10 | 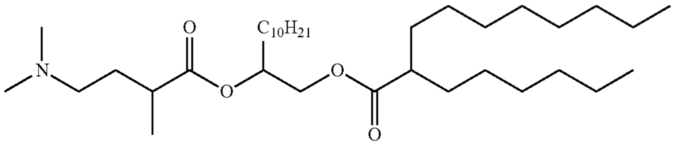 | 8.3E+04 |

TABLE 3-continued
Transfection expression intensity of 98 amino lipid compounds on BMDC
| Serial number | Serial number of amino lipid | Structure | Fluorescence intensity |
|---|---|---|---|
| 28 | E7C 71A11 | 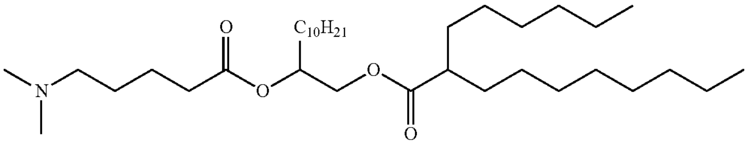 | 4.4E+ 04 |
| 29 | E7C 74A9 | 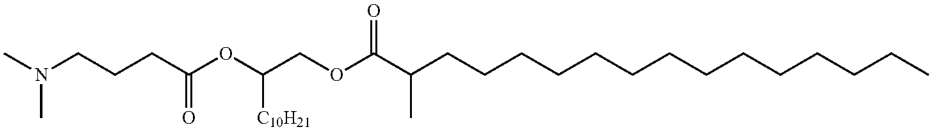 | 4.8E+ 04 |
| 30 | E7C 74A10 | 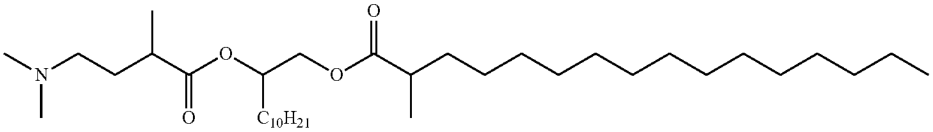 | 3.7E+ 04 |
| 31 | E7C 74A11 | 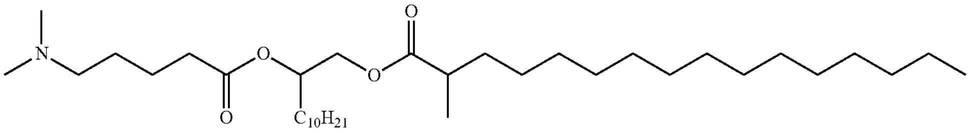 | 3.2E+ 04 |
| 32 | E7C 79A9 | 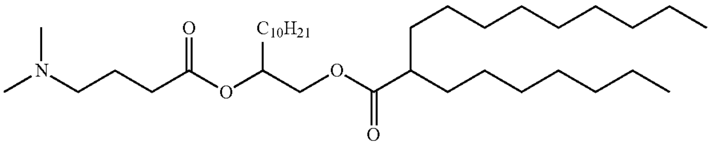 | 5.6E+ 04 |
| 33 | E7C 79A10 | 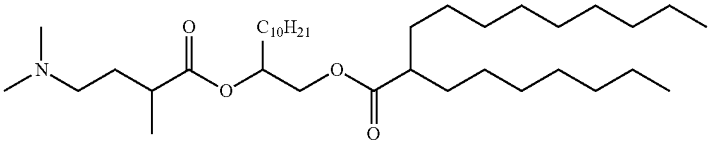 | 3.6E+ 04 |
| 34 | E7C 79A11 | 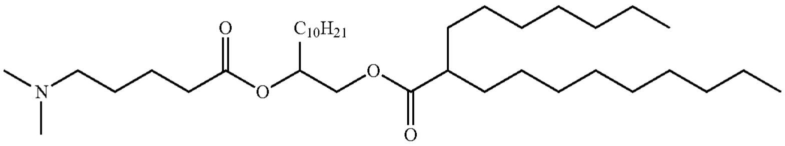 | 4.2E+ 04 |
| 35 | E7C 79A12 | 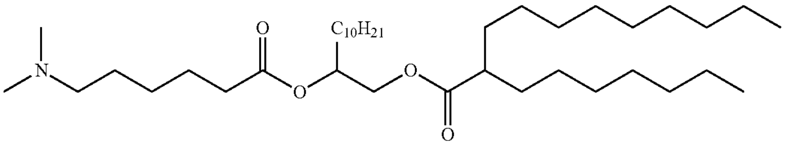 | 3.5E+ 04 |
| 36 | E8C 71A9 | 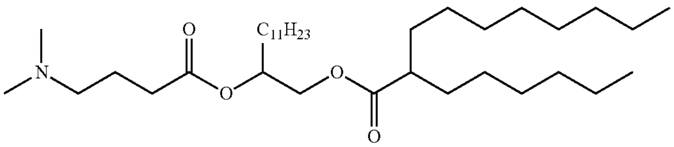 | 8.8E+ 04 |

TABLE 3-continued
Transfection expression intensity of 98 amino lipid compounds on BMDC
| Serial number | Serial number of amino lipid | Structure | Fluorescence intensity |
|---|---|---|---|
| 37 | E8C 71A11 | 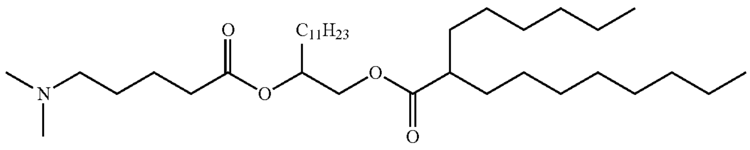 | 5.4E+04 |
| 38 | E8C 71A23 | 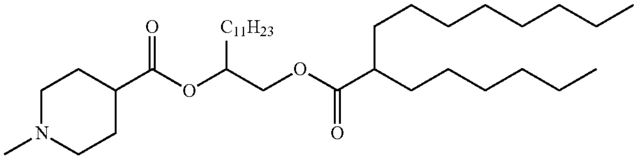 | 1.5E+04 |
| 39 | E8C 72A9 | 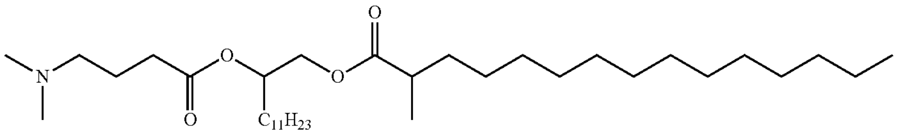 | 6.1E+04 |
| 40 | E8C 72A11 | 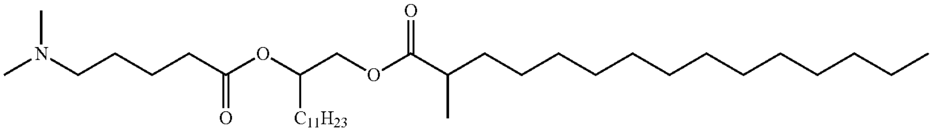 | 7.3E+04 |
| 41 | E8C 74A9 | 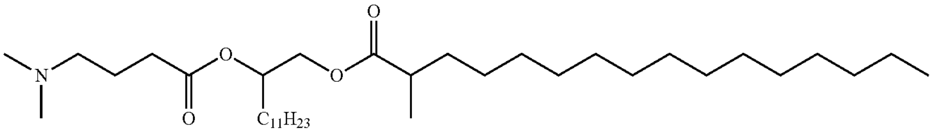 | 8.5E+04 |
| 42 | E8C 74A11 | 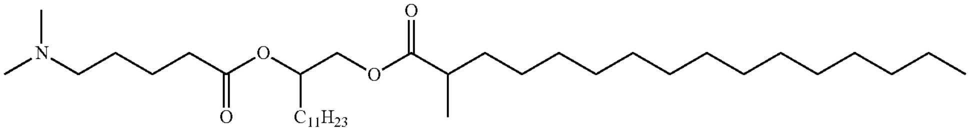 | 4.0E+04 |
| 43 | E8C 74A23 | 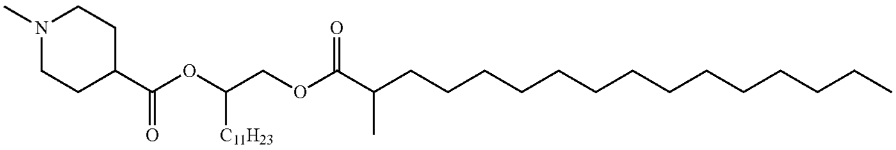 | 1.3E+04 |
| 44 | E8C 79A9 | 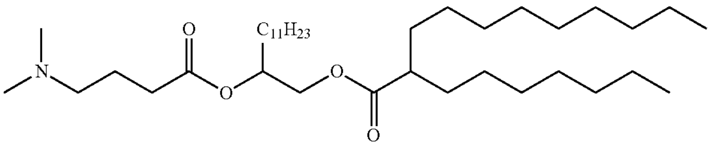 | 3.6E+04 |
| 45 | E9C 56A10 | 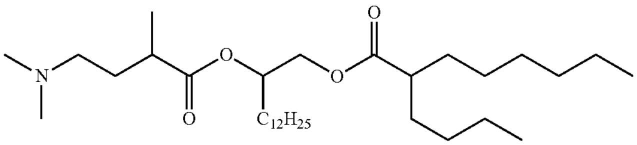 | 8.8E+04 |

TABLE 3-continued
Transfection expression intensity of 98 amino lipid compounds on BMDC
| Serial number | Serial number of amino lipid | Structure | Fluorescence intensity |
|---|---|---|---|
| 46 | E9C 57A10 | 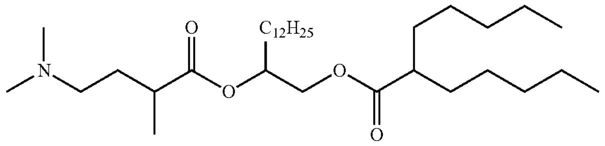 | 3.2E+04 |
| 47 | E9C 58A11 | 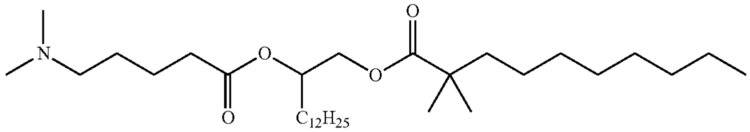 | 3.5E+04 |
| 48 | E9C 60A23 | 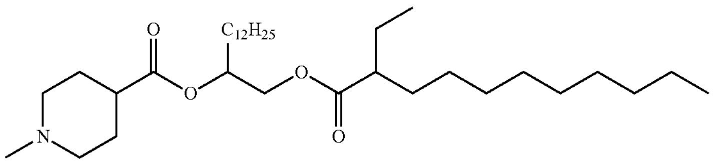 | 1.8E+04 |
| 49 | E9C 62A10 | 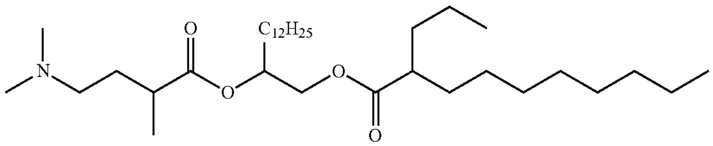 | 4.3E+04 |
| 50 | E9C 63A10 | 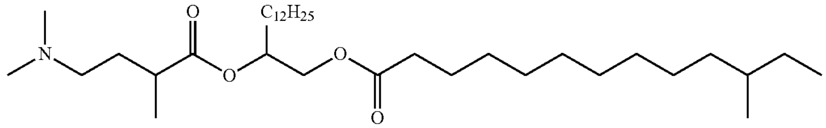 | 5.6E+04 |
| 51 | E9C 64A9 | 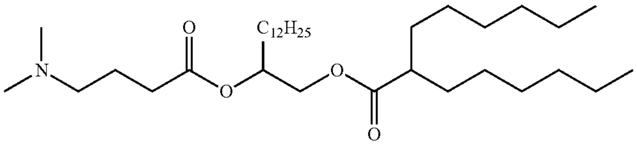 | 8.9E+04 |
| 52 | E9C 64A10 | 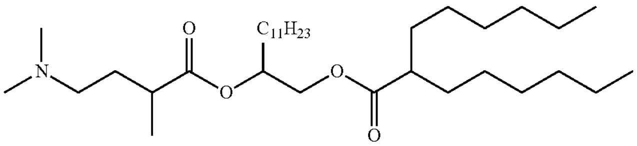 | 6.1E+04 |
| 53 | E9C 66A9 | 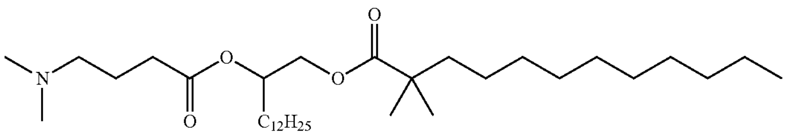 | 2.3E+04 |
| 54 | E9C 67A10 | 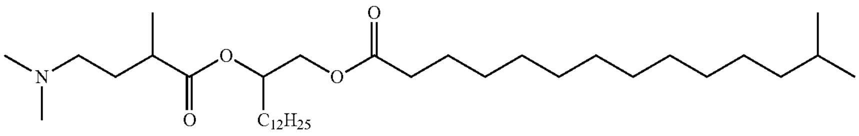 | 7.8E+04 |

TABLE 3-continued
Transfection expression intensity of 98 amino lipid compounds on BMDC
| Serial number | Serial number of amino lipid | Structure | Fluorescence intensity |
|---|---|---|---|
| 55 | E10C 74A9 | 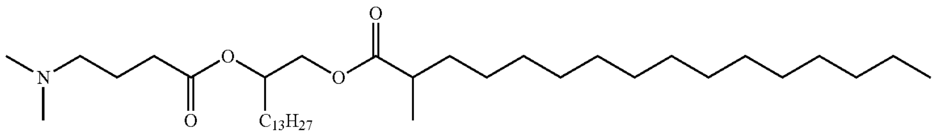 | 1.3E+04 |
| 56 | E10C 74A23 | 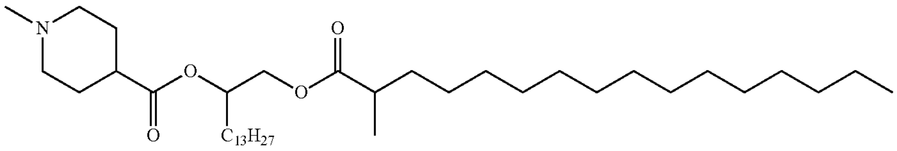 | 1.0E+04 |
| 57 | E10C 79A9 | 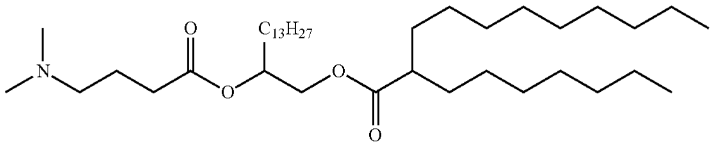 | 1.3E+04 |
| 58 | E11C 7A9 | 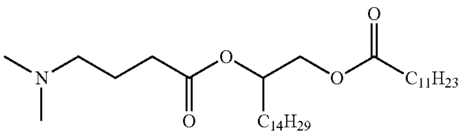 | 1.5E+04 |
| 59 | E11C 57A11 | 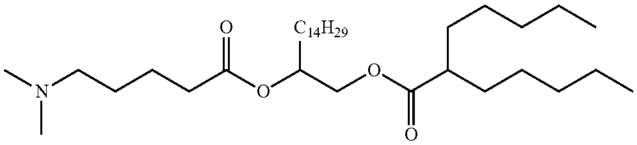 | 6.4E+04 |
| 60 | E11C 58A11 | 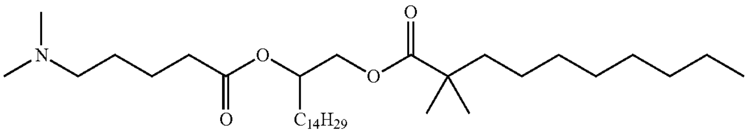 | 2.3E+04 |
| 61 | E11C 60A11 | 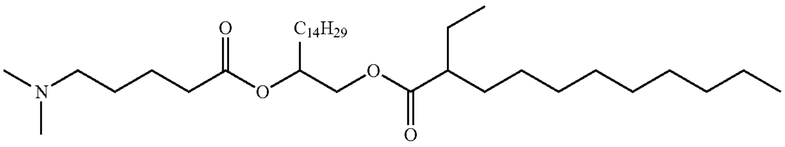 | 3.3E+04 |
| 62 | E11C 62A11 | 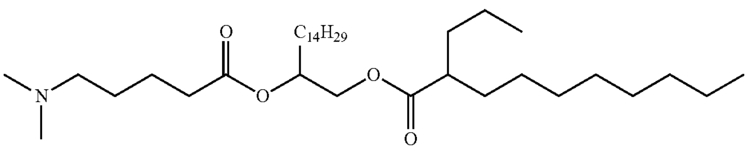 | 4.1E+04 |
| 63 | E12C 6A11 | 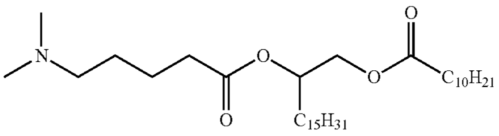 | 1.2E+04 |

TABLE 3-continued
| Serial number | Serial number of amino lipid | Structure | Fluorescence intensity |
|---|---|---|---|
| 64 | E12C 64A23 | 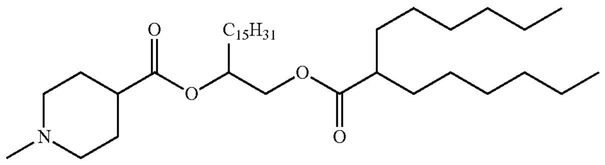 | 1.8E+04 |
| 65 | E12C 74A11 | 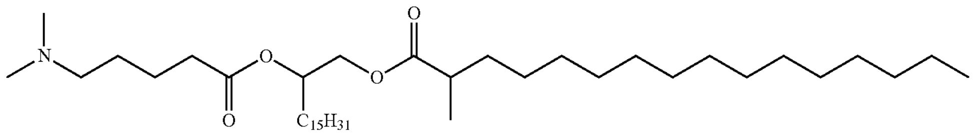 | 1.1E+04 |
| 66 | E15C 79A10 | 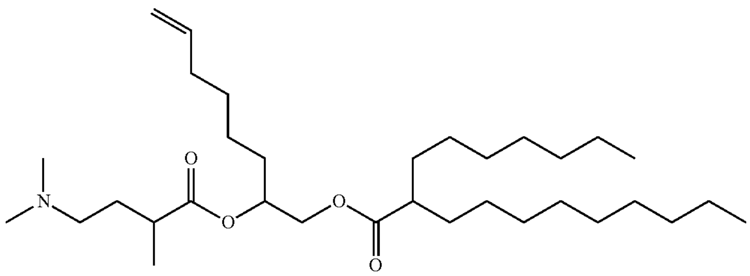 [SMILES: C=CCCCCC(COC(=O)C(CCCCCCC)CCCCCCCCC)OC(=O)C(C)CCN(C)C] | 8.9E+04 |
| 67 | E15C 79A11 | 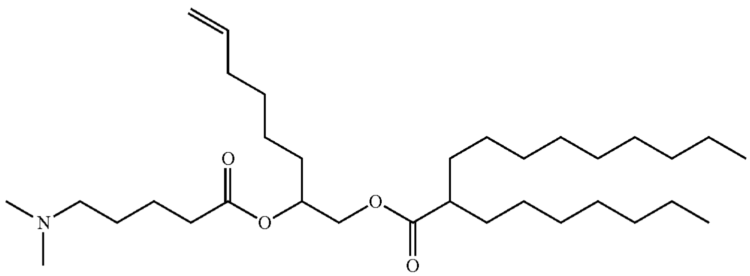 [SMILES: C=CCCCCC(COC(=O)C(CCCCCCC)CCCCCCCCC)OC(=O)CCCCN(C)C] | 3.0E+04 |
| 68 | E15C 79A12 | 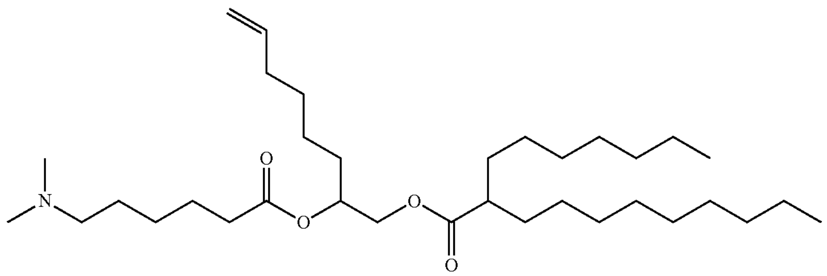 [SMILES: C=CCCCCC(COC(=O)C(CCCCCCC)CCCCCCCCC)OC(=O)CCCCCN(C)C] | 4.4E+04 |
| 69 | E20C 9A10 | 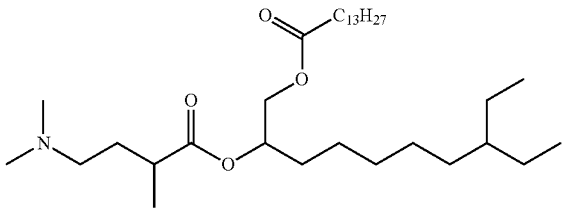 | 2.7E+04 |
Transfection expression intensity of 98 amino lipid compounds on BMDC TABLE 3-continued
Transfection expression intensity of 98 amino lipid compounds on BMDC
| Serial number | Serial number of amino lipid | Structure | Fluorescence intensity |
|---|---|---|---|
| 70 | E20C 9A11 | 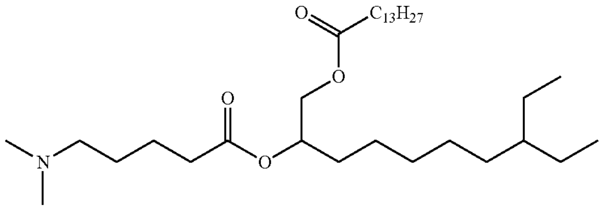 | 4.0E+04 |
| 71 | E20C 10A9 | 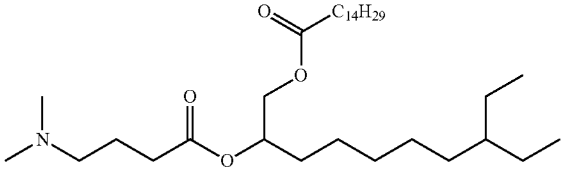 | 4.8E+04 |
| 72 | E20C 10A10 | 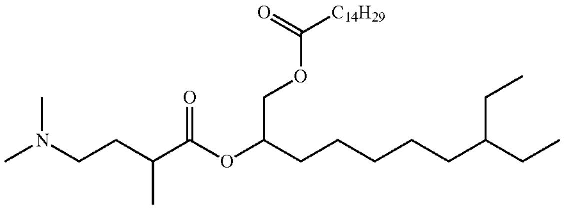 | 1.2E+04 |
| 73 | E20C 10A11 | 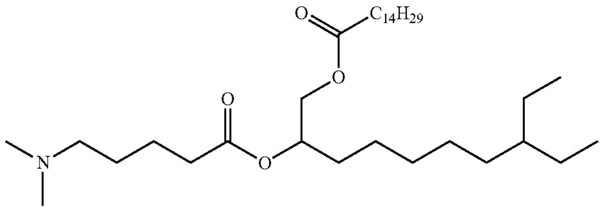 | 1.9E+04 |
| 74 | E20C 10A12 | 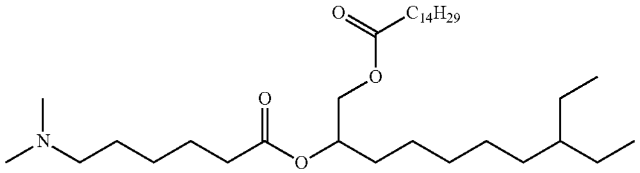 | 3.6E+04 |
| 75 | E20C 11A9 | 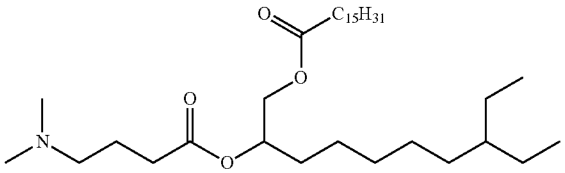 | 9.9E+04 |
| 76 | E20C 11A10 | 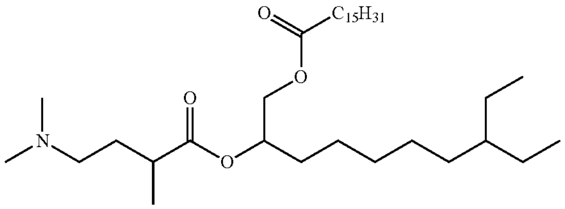 | 4.5E+04 |

TABLE 3-continued
Transfection expression intensity of 98 amino lipid compounds on BMDC
| Serial number | Serial number of amino lipid | Structure | Fluorescence intensity |
|---|---|---|---|
| 77 | E20C 11A23 | 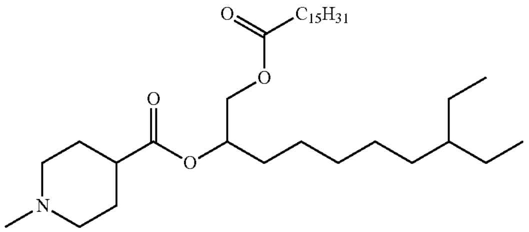 | 1.6E+ 04 |
| 78 | E20C 12A9 | 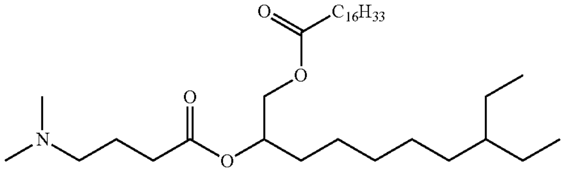 | 4.9E+ 04 |
| 79 | E20C 12A10 | 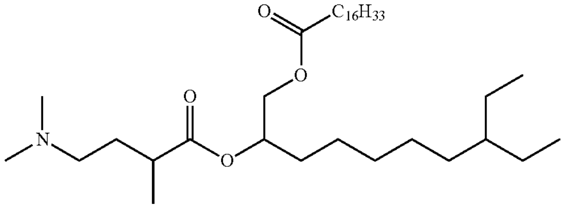 | 9.6E+ 04 |
| 80 | E20C 12A23 | 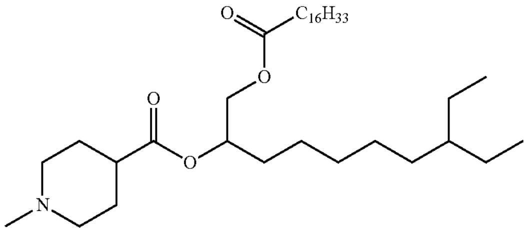 | 1.7E+ 04 |
| 81 | E20C 64A9 | 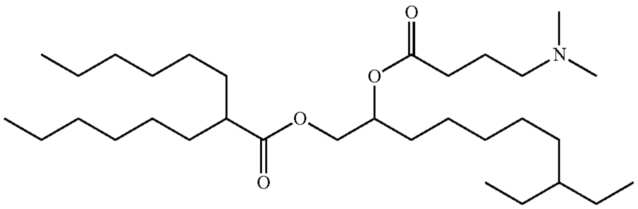 [SMILES: CCCCCCC(CCCCCC)C(=O)OCC(CCCCCC(CC)CC)OC(=O)CCCN(C)C] | 3.0E+ 04 |
| 82 | E20C 66A9 | 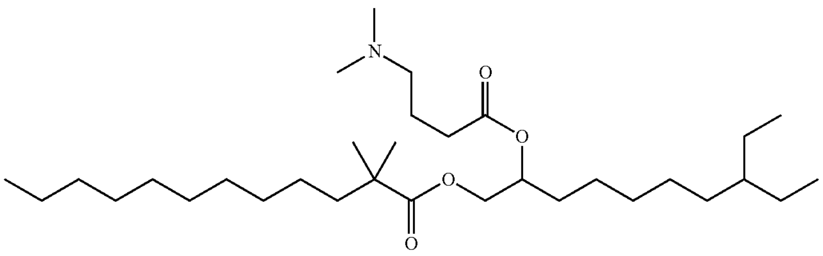 [SMILES: CCCCCCCCCCC(C)(C)C(=O)OCC(CCCCCC(CC)CC)OC(=O)CCCN(C)C] | 5.9E+ 04 |

TABLE 3-continued
| Transfection expression intensity of 98 amino lipid compounds on BMDC | | | |
|---|---|---|---|
| Serial number | Serial number of amino lipid | Structure | Fluorescence intensity |
| 83 | E20C 67A9 | 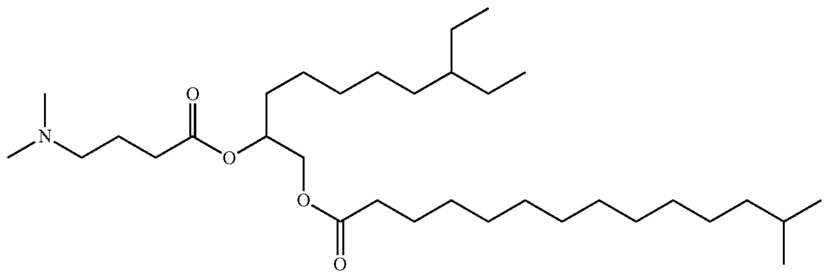 [SMILES: CCC(CC)CCCCCC(COC(=O)CCCCCCCCCCCC(C)C)OC(=O)CCCN(C)C] | 9.5E+03 |
| 84 | E20C 71A9 | 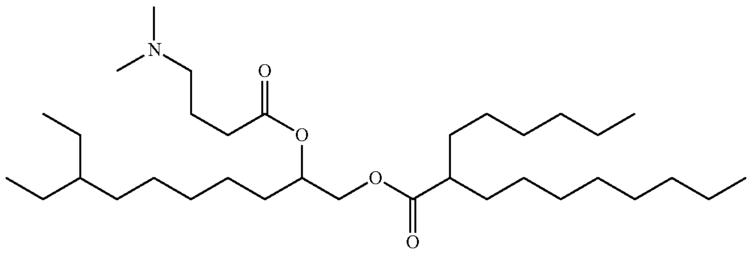 [SMILES: CCCCCCCCC(CCCCCC)C(=O)OCC(CCCCCC(CC)CC)OC(=O)CCCN(C)C] | 6.6E+04 |
| 85 | E20C 72A9 | 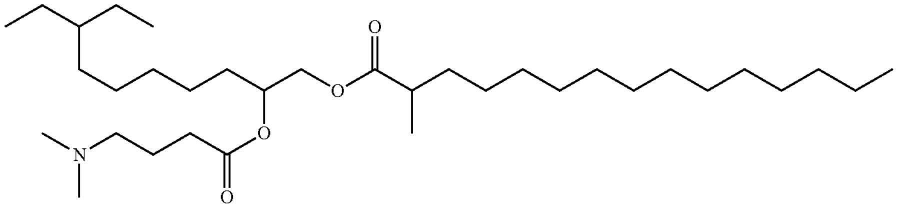 [SMILES: CCCCCCCCCCCCCC(C)C(=O)OCC(CCCCCC(CC)CC)OC(=O)CCCN(C)C] | 4.7E+03 |
| 86 | E21C 11A9 | 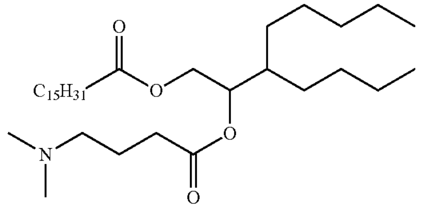 | 8.7E+03 |
| 87 | E21C 11A10 | 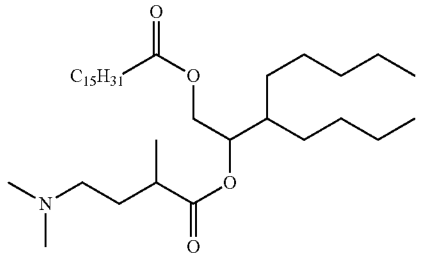 | 1.7E+04 |

TABLE 3-continued
| Transfection expression intensity of 98 amino lipid compounds on BMDC | | | |
|---|---|---|---|
| Serial number | Serial number of amino lipid | Structure | Fluorescence intensity |
| 88 | E21C 11A11 | 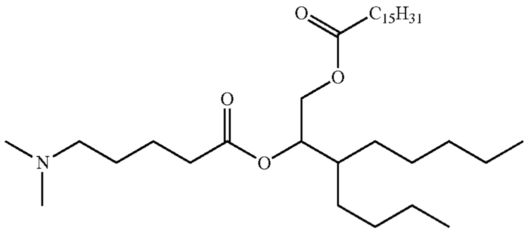 | 4.7E+04 |
| 89 | E21C 12A9 | 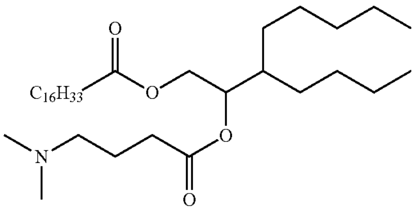 | 5.4E+04 |
| 90 | E21C 12A10 | 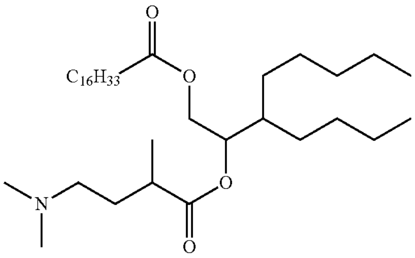 | 8.9E+04 |
| 91 | E21C 12A11 | 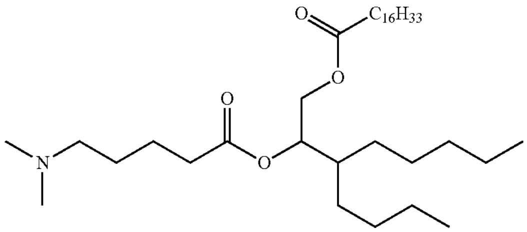 | 9.5E+04 |
| 92 | E21C 13A9 | 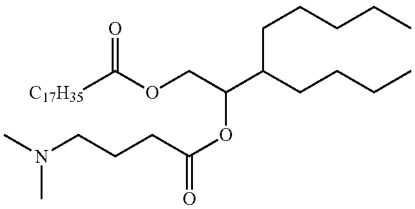 | 6.7E+04 |
| 93 | E21C 13A11 | 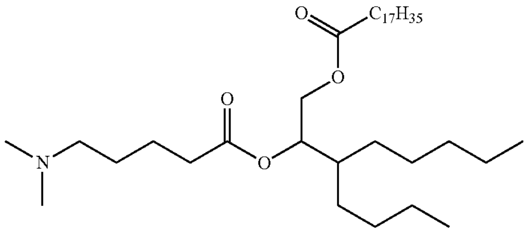 | 6.4E+04 |

TABLE 3-continued

| Serial number | Serial number of amino lipid | Structure | Fluorescence intensity |
|---|---|---|---|
| Transfection expression intensity of 98 amino lipid compounds on BMDC | | | |
| 94 | E21C 14A9 | 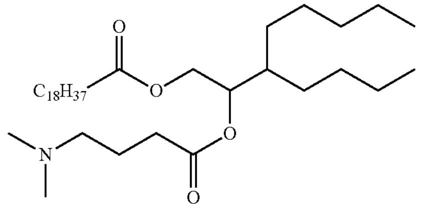 | 4.5E+04 |
| 95 | E21C 67A9 | 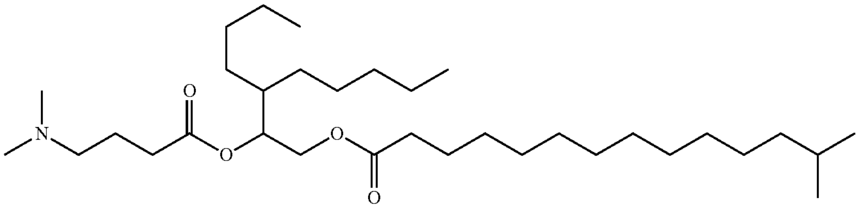 [SMILES: CCCCCC(CCCC)C(COC(=O)CCCCCCCCCCCC(C)C)OC(=O)CCCN(C)C] | 3.2E+04 |
| 96 | E21C 71A23 | 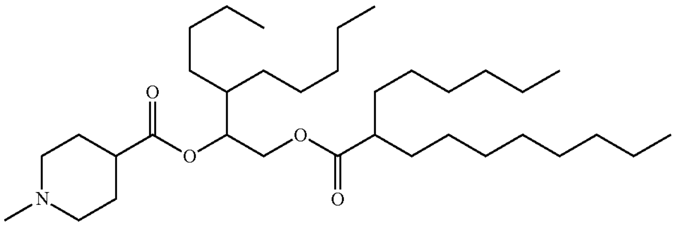 [SMILES: CCCCCCCCC(CCCCCC)C(=O)OCC(OC(=O)C1CCN(C)CC1)C(CCCC)CCCCC] | 1.9E+04 |
| 97 | E24C 9A9 | 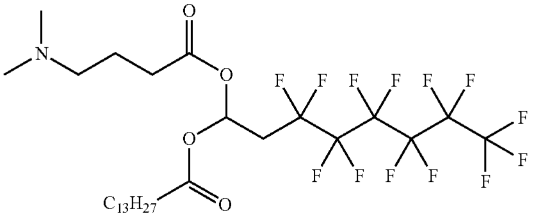 | 1.1E+04 |
| 98 | DLin-MC3 | | 2.1E+04 |

Embodiment 14: Evaluation on Luciferase mRNA In-Vivo Delivery Performance of Lipid Nanoparticles Prepared from Amino Lipid Compounds 1. Preparation of Lipid Nanoparticles The amino lipid compounds of the disclosure, neutral lipids (such as DSPC, DOPE and cholesterin) and polyethylene glycolated lipids (such as PEG2000-DMG and PEG2000-DSPE) were mixed according to an optimized mole ratio and were dissolved in absolute ethyl alcohol. The obtained ethyl alcohol solution and a sodium acetate buffer solution (25 mM, pH=5.0) dissolved with Luc-mRNA were mixed according to a volume ratio of 1:3 by using a micro-fluidic preparation system to prepare a coarse solution of the lipid nanoparticles. Then, the coarse solution was dialyzed for 6 h under the condition of 1×PBS and temperature control at 4° C. by a dialysis cassettes or box (MWCO 20,000). Filtration was performed by a 0.22 μm microporous filtering membrane prior to use. A mass ratio of the amino lipid compound to luciferase mRNA (Luc mRNA) was about 10:1.

Characterization of Lipid Nanoparticles

Characterization of particle size: the particle size and PDI of the prepared lipid nanoparticles were measured through Zetasizer Nano-ZSZEN3600. 20 μL of the LNP solution was taken for particle size measurement. Three times were performed, and each time lasted for 30 s.

Encapsulation efficiency determination: the determination was performed with the reference to a RiboGreen RNA assay kit standard procedure.

TABLE 4

Characterization data of LNP prepared from representative amino lipid compounds

| Serial number | Serial number of amino lipid | Z-Average (d · nm) | PDI | Encapsulation efficiency |
|---|---|---|---|---|
| LNP-1 | E4C79A9 | 122.4 | 0.12 | 93.9% |
| LNP-2 | E4C79A11 | 124.6 | 0.14 | 94.1% |
| LNP-3 | E4C79A12 | 122.1 | 0.07 | 95.3% |
| LNP-4 | E5C71A11 | 123.1 | 0.10 | 93.5% |
| LNP-5 | E5C79A11 | 131.2 | 0.07 | 95.6% |
| LNP-6 | E6C71A11 | 124.1 | 0.13 | 93.0% |
| LNP-7 | E6C71A12 | 110.1 | 0.09 | 93.6% |
| LNP-8 | E6C79A10 | 129.2 | 0.05 | 94.4% |
| LNP-9 | E6C79A11 | 141.2 | 0.08 | 95.6% |
| LNP-10 | E6C79A12 | 123.4 | 0.10 | 93.7% |
| LNP-11 | E7C71A9 | 112.1 | 0.02 | 96.6% |
| LNP-12 | E7C71A10 | 126.8 | 0.09 | 95.3% |
| LNP-13 | E7C79A9 | 129.8 | 0.08 | 94.9% |
| LNP-14 | E7C79A10 | 148.3 | 0.04 | 95.2% |
| LNP-15 | E7C79A11 | 140.1 | 0.02 | 95.4% |
| LNP-16 | E8C71A9 | 147.6 | 0.09 | 93.1% |
| LNP-17 | E8C71A11 | 136.4 | 0.04 | 94.8% |
| LNP-18 | E8C71A12 | 139.5 | 0.02 | 95.0% |
| LNP-19 | E8C79A9 | 123.6 | 0.06 | 91.8% |
| LNP-20 | E9C56A10 | 140.9 | 0.15 | 95.9% |
| LNP-21 | E9C57A10 | 140.4 | 0.13 | 92.2% |
| LNP-22 | E9C62A10 | 139.2 | 0.02 | 93.0% |
| LNP-23 | E9C64A9 | 150.4 | 0.12 | 94.4% |
| LNP-24 | E9C64A10 | 143.7 | 0.12 | 95.2% |
| LNP-25 | E9C71A10 | 139.9 | 0.12 | 92.5% |
| LNP-26 | E11C57A11 | 157.6 | 0.08 | 93.6% |
| LNP-27 | E11C60A11 | 103.7 | 0.05 | 92.9% |
| LNP-28 | E11C62A11 | 102.6 | 0.05 | 91.4% |
| LNP-29 | E15C79A11 | 100.2 | 0.02 | 93.3% |
| LNP-30 | E15C79A12 | 107.1 | 0.08 | 92.1% |
| LNP-31 | E20C10A12 | 111.9 | 0.11 | 93.4% |
| LNP-32 | E20C11A10 | 109.8 | 0.06 | 94.0% |
| LNP-33 | E20C12A9 | 103.3 | 0.09 | 93.6% |
| LNP-34 | E20C71A9 | 107.2 | 0.14 | 95.3% |
| LNP-35 | E21C11A11 | 101.1 | 0.12 | 94.1% |
| LNP-36 | E21C12A9 | 109.7 | 0.05 | 95.0% |
| LNP-37 | E6C71A12 | 139.3 | 0.10 | 93.5% |
| LNP-38 | E7C71A9 | 141.7 | 0.09 | 92.6% |
| LNP-39 | DLin-MC3 | 139.2 | 0.15 | 94.6% |
| LNP-40 | E6C71A12 | 139.8 | 0.05 | 93.5% |
| LNP-41 | E7C71A9 | 141.3 | 0.10 | 94.6% |
| LNP-42 | E6C71A12 | 137.3 | 0.08 | 93.6% |
| LNP-43 | E7C71A9 | 140.1 | 0.09 | 93.5% |
| LNP-44 | E6C71A12 | 134.7 | 0.13 | 94.6% |
| LNP-45 | E7C71A9 | 138.9 | 0.11 | 94.5% |
| LNP-46 | E6C71A12 | 132.3 | 0.04 | 93.4% |
| LNP-47 | E7C71A9 | 124.2 | 0.06 | 94.5% |

Note: in the above table:

the lipid formulation of LNP-1 to LNP-36 was as follows: amino lipid:DSPC:cholesterol:PEG2000-DMG=50:10:38.5:1.5;

the lipid formulation of LNP-37 to LNP-39 was as follows: amino lipid:DOPE:cholesterol:PEG2000-DMG=45:10:42.5:1.5;

the lipid formulation of LNP-40 to LNP-41 was as follows: amino lipid:DOPC:cholesterol:PEG2000-DMG=55:5:38.5:1.5;

the lipid formulation of LNP-42 to LNP-43 was as follows: amino lipid:cholesterol:PEG2000-DSPE=60:35.5:4.5;

the lipid formulation of LNP-44 to LNP-45 was as follows: amino lipid:DSPC:DOPC:cholesterol:PEG2000-DMG=45:10:5:38.0:2.0; and the lipid formulation of LNP-46 to LNP-47 was as follows: amino lipid:DSPC:DOPE:cholesterol:PEG2000-DSPE=50:10:5:33.5:1.5.

2. Animal Tests

Animal preparation: 6-week-old female C57BL/6 mice with the body weight about 20 g were selected. The feeding environment was an SPF stage feeding room. Animal tests were strictly performed according to the guide of the national health institute and the animal ethics requirements.

In-vivo delivery: 9 C57BL/6 mice were randomly selected for each group. According to the mRNA standard of 0.5 mg/kg, the lipid nanoparticle solution was respectively injected in three administration manners of subcutaneous, intramuscular and tail intravenous injection (3 mice for each administration manner). After 12 h, 200 μL of 10 mg/mL D-luciferin potassium salt was injected into each mouse through tail intravenous injection. After 10 min, the mice were placed in an in-vivo living imaging system (in-vivo imaging system 200 series, in-vivo imaging spectrum imaging system), the total fluorescence intensity of each mouse was observed, and photos were taken for recording. The expression intensity of the Fluc mRNA delivered by the representative amino lipid compounds in 3 administration manners was as shown in Table 5 to Table 7. DLin-MC3 was used as a control.

TABLE 5

Expression intensity of Luc mRNA delivered by LNP subcutaneous administration of representative amino lipid compounds

| Serial number | Serial number of LNP | Average fluorescence intensity |
|---|---|---|
| 1 | LNP-1 | 2.4E+06 |
| 2 | LNP-4 | 5.3E+06 |
| 3 | LNP-5 | 1.5E+06 |
| 4 | LNP-6 | 7.9E+06 |
| 5 | LNP-7 | 7.0E+07 |
| 6 | LNP-11 | 8.9E+07 |
| 7 | LNP-16 | 6.6E+06 |
| 8 | LNP-17 | 3.1E+06 |
| 9 | LNP-20 | 7.7E+06 |
| 10 | LNP-25 | 2.5E+06 |
| 11 | LNP-29 | 6.3E+07 |
| 12 | LNP-32 | 1.8E+06 |
| 13 | LNP-34 | 5.9E+06 |
| 14 | LNP-35 | 4.8E+06 |
| 15 | LNP-37 | 5.8E+06 |
| 16 | LNP-38 | 1.4E+06 |
| 17 | LNP-39 | 4.5E+06 |
| 18 | LNP-43 | 5.7E+07 |

TABLE 6

Expression intensity of Luc mRNA delivered by LNP intramuscular injection administration of representative amino lipid compounds

| Serial number | Serial number of LNP | Fluorescence intensity |
|---|---|---|
| 1 | LNP-2 | 4.3E+06 |
| 2 | LNP-7 | 5.1E+07 |
| 3 | LNP-8 | 4.5E+06 |
| 4 | LNP-11 | 7.6E+07 |
| 5 | LNP-12 | 1.9E+06 |
| 6 | LNP-14 | 8.6E+06 |
| 7 | LNP-15 | 3.1E+06 |
| 8 | LNP-23 | 9.7E+06 |
| 9 | LNP-26 | 3.3E+06 |
| 10 | LNP-27 | 7.7E+06 |
| 11 | LNP-30 | 2.8E+06 |
| 12 | LNP-39 | 7.4E+06 |
| 13 | LNP-40 | 3.5E+06 |
| 14 | LNP-41 | 2.7E+06 |
| 15 | LNP-42 | 6.5E+06 |
| 16 | LNP-45 | 3.4E+07 |
| 17 | LNP-46 | 8.5E+06 |
| 18 | LNP-47 | 5.7E+06 |

TABLE 7

| Expression intensity of Luc mRNA delivered by LNP tail intravenous administration of representative amino lipid compounds | | |
|---|---|---|
| Serial number | Serial number of LNP | Fluorescence intensity |
| 1 | LNP-3 | 3.4E+06 |
| 2 | LNP-7 | 8.3E+07 |
| 3 | LNP-9 | 5.9E+06 |
| 4 | LNP-10 | 1.9E+07 |
| 5 | LNP-11 | 7.0E+07 |
| 6 | LNP-13 | 4.9E+06 |
| 7 | LNP-18 | 5.6E+06 |
| 8 | LNP-19 | 3.9E+07 |
| 9 | LNP-21 | 1.1E+07 |
| 10 | LNP-22 | 5.7E+06 |
| 11 | LNP-24 | 6.4E+06 |
| 12 | LNP-28 | 7.9E+06 |
| 13 | LNP-31 | 5.8E+06 |
| 14 | LNP-33 | 2.6E+06 |
| 15 | LNP-39 | 4.7E+06 |
| 16 | LNP-42 | 8.4E+07 |
| 17 | LNP-43 | 7.5E+07 |
| 18 | LNP-44 | 5.3E+06 |

Embodiment 15: In-Vivo Immunity and Tumor Treatment Effect Evaluation of Lipid Nanoparticles Prepared from Amino Lipid Compounds Preparation method: the amino lipid compounds of the disclosure, DSPC, cholesterol and PEG2000-DMG were mixed according to a mole ratio of 50:10:38.5:1.5 and were dissolved in absolute ethyl alcohol. OVA mRNA was dissolved in a sodium acetate buffer solution (50 nM, pH=4.0). The obtained ethyl alcohol solution and the acetate buffer solution (25 nM, pH=5.0) dissolved with Luc-mRNA were mixed in a micro-fluidic chip according to a volume ratio of 1:3 by using a micro-fluidic preparation system to obtain lipid nanoparticles. Then, dialysis was performed for 6 h under the conditions of 1×PBS and temperature was controlled at 4° C. by using a dialysis cassettes or box (MWCO 20,000). Filtration was performed by a 0.22 μm microporous filtering membrane prior to use. The mass ratio of the amino lipid compound to OVA mRNA was about 10:1.

Animal preparation: 5-6-week-old female C57BL/6 mice with the body weight about 18 to 20 g were selected. The feeding environment was an SPF stage feeding room. Animal tests were strictly performed according to the guide of the national health institute and the animal ethics requirements.

Figure 3:
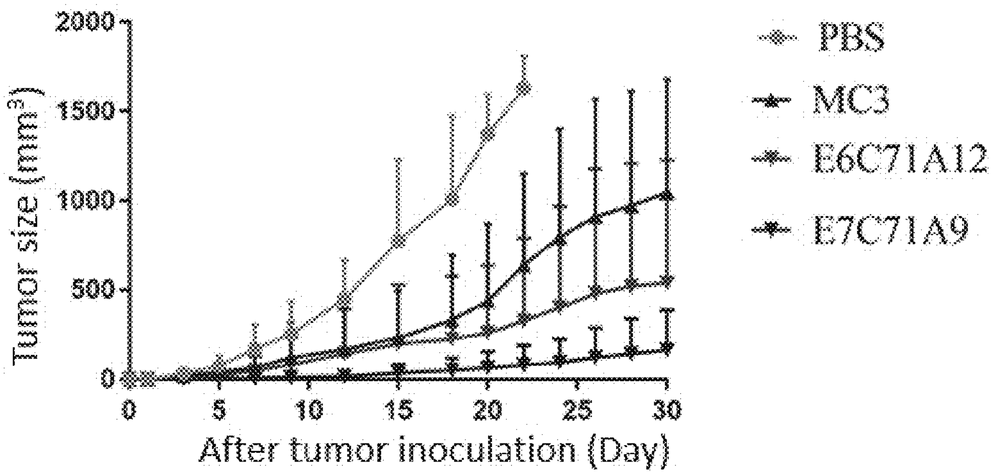
FIG. 3 is a tumor growth curve diagram of tumor-bearing mice after receiving intramuscular injection of OVA mRNA vaccines in Embodiment 15 (LNPs assembled by E6C71A12 and E7C71A9 are respectively used).
Figure 4:
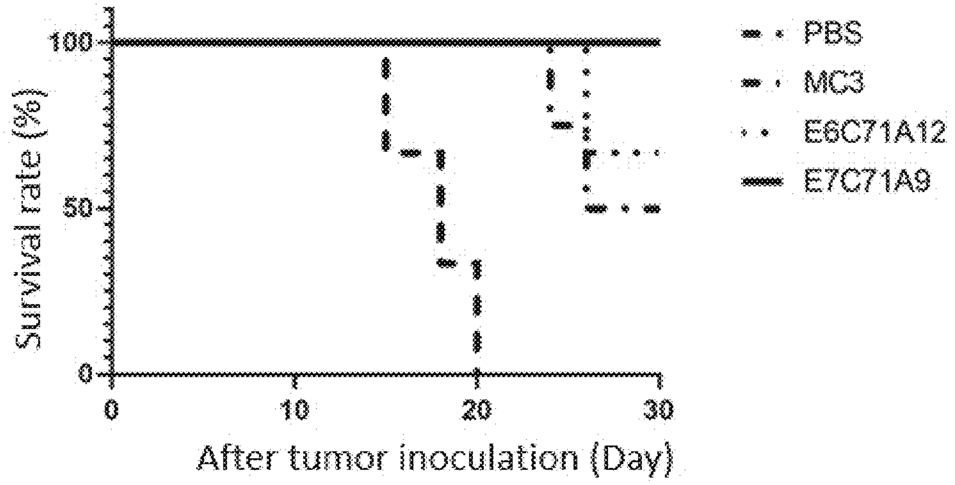
FIG. 4 is a survival curve of tumor-bearing mice after receiving intramuscular injection of OVA mRNA vaccines in Embodiment 15 (LNPs assembled by E6C71A12 and E7C71A9 are respectively used).

In-vivo delivery: B16-OVA melanoma cells ($1.5\times10^5$) were injected to the outer thighs of the mice through subcutaneous injection. When the tumor grew to 50 $mm^3$ (on the about $6^{th}$ or $7^{th}$ day after tumor inoculation), the mice began to inoculated vaccines, the animals were subjected to twice immunization through intramuscular injection of an LNP preparation containing 1 μg OVA-mRNA. An interval between first and second injections was 7 days. The tumor growth was measured for 3 times every week by a digital display calliper, and a calculation formula was 0.5×length× width. When the tumor size reached 1500 $mm^3$, the mice received euthanasia. The tumor growth speeds of E7C71A9 and E6C71A12 were obviously lower than that of MC3 group (as shown in FIG. 3). Additionally, 60% of mice (E7C71A9 group) and 40% of mice (E6C71A12 group) respectively reached the complete relieving effect. The result was obviously superior to that of MC3 group (as shown in FIG. 4).

Embodiment 16: 2-Hydroxydodecyl-2-Heptylnonanoate

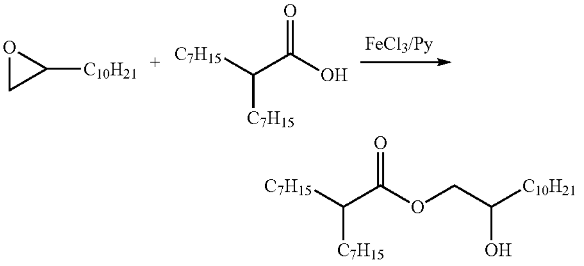

$FeCl_3$ (20 mg, 0.125 mmol), Py (5 μL, 0.0625 mmol), 2-heptyl pelargonic acid (1.28 g, 5 mmol) and 1,2-cyclododecane epoxide (1.84 g, 10 mmol) were sequentially added into a 25 mL reaction tube, and the reaction was stirred at room temperature overnight. The column chromatography gradient elution purification (hexane:EA=20:1 to 5:1) was performed to obtain 2-hydroxydodecyl-2-heptylnonanoate (1.54 g, 70% yield). $^1H$ NMR (400 MHz, $CDCl_3$): δ 0.85-0.89 (m, 9H), 1.25-1.26 (m, 36H), 1.39-1.41 (m, 2H), 1.58-1.62 (m, 4H), 2.11-2.14 (m, 1H), 4.05-4.11 (m, 2H), 4.33-4.35 (m, 1H), 5.37 (brs, 1H). ESI-MS calculated for $C_{28}H_{57}O_3^+$ $[M+H]^+$ 441.4, found 441.7.

Embodiment 17: 2-((4-(Dimethylamino)Butanoyl)Oxy) Dodecyl 2-Heptylnonanoate

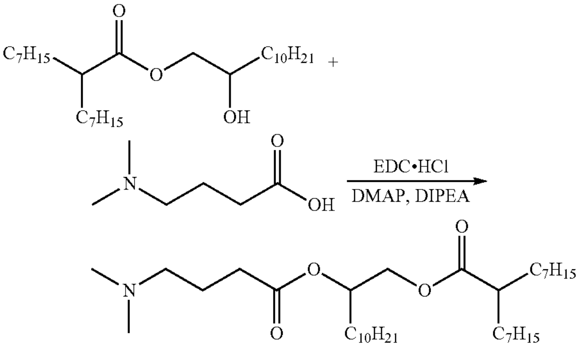

E7C114A9

EDC·HCl (192 mg, 1 mmol), DIPEA (174 μL, 1 mmol), DMAP (3.0 mg, 0.025 mmol), 4-(dimethylamino)butanoic acid (101 mg, 0.6 mmol), 2-hydroxy dodecyl 2-heptyl pelargonate (220 mg, 0.5 mmol) and DCM (4 mL) were sequentially added into a 10 mL reaction tube, and the reaction was stirred for 3 h at room temperature. The column chromatography gradient elution purification (DCM: MeOH=100:1 to 100:3) was performed to obtain the compound E7C114A9 (222 mg, 80% yield). $^1H$ NMR (400 MHz, $CDCl_3$): δ 0.85-0.89 (m, 9H), 1.25-1.44 (m, 38H), 1.55-1.58 (m, 4H), 1.75-1.83 (m, 2H), 2.23 (s, 6H), 2.28-2.39 (m, 5H), 4.01-4.06 (dd, $J_1$=11.7 Hz, $J_2$=6.1 Hz, 1H), 4.21-4.25 (dd, $J_1$=11.8 Hz, $J_2$=3.5 Hz, 1H), 5.05-5.07 (m, 1H). $^{13}C$ NMR (100 MHz, $CDCl_3$): δ 14.1, 22.7, 23.4, 25.3, 29.3, 29.4, 29.6, 31.9, 32.7, 44.7, 47.0, 61.0, 65.8, 70.7, 173.1, 175.8. ESI-MS calculated for $C_{34}H_{68}NO_4^+$ $[M+H]^+$ 554.5, found 554.4.

Embodiment 18:2-Hydroxytetradecyl-3-Hexylundecanoate

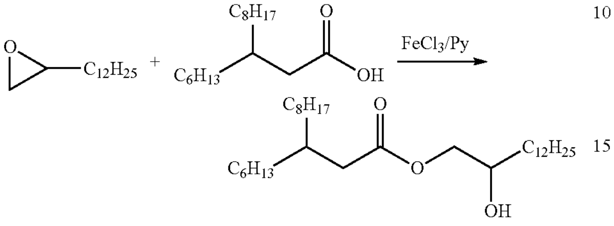

$FeCl_3$ (20 mg, 0.125 mmol), Py (5 μL, 0.0625 mmol), 3-hexyl undecanoic acid (1.36 g, 5 mmol) and 1,2-epoxytetradecane (2.12 g, 10 mmol) were sequentially added into a 25 mL reaction tube, and the reaction was stirred at room temperature overnight. The column chromatography gradient elution purification (hexane:EA=20:1 to 5:1) was performed to obtain 2-hydroxytetradecyl 3-hexylundecanoate (1.59 g, 66% yield). $^1$H NMR (400 MHz, $CDCl_3$): δ 0.87-0.90 (m, 9H), 1.24-1.28 (m, 44H), 1.39-1.41 (m, 2H), 1.92-1.95 (m, 1H), 2.02-2.04 (m, 1H), 2.26-2.29 (m, 1H), 4.09-4.14 (m, 2H), 4.33-4.35 (m, 1H), 5.38 (brs, 1H). ESI-MS calculated for $C_{31}H_{63}O_3^+$ $[M+H]^+$ 483.5, found 483.8.

Embodiment 19: 2-((3-(Piperidin-1-Yl) Propanoyl) Oxy)Tetradecyl-3-Hexylundecanoate

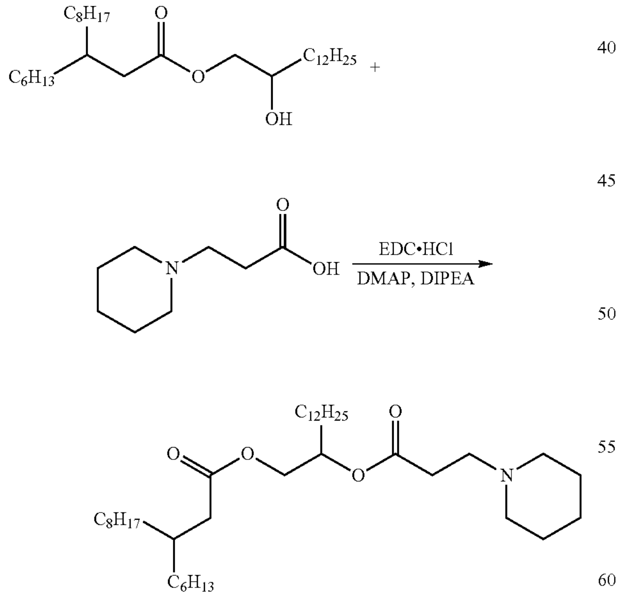

E9C126A24

EDC·HCl (192 mg, 1 mmol), DIPEA (174 μL, 1 mmol), DMAP (3.0 mg, 0.025 mmol), 3-piperidine-1-propionic acid (95 mg, 0.6 mmol), 2-hydroxytetradecyl 3-hexylundecanoate (242 mg, 0.5 mmol) and DCM (4 mL) were sequentially added into a 10 mL reaction tube, stirring reaction was performed for 3 h at a room temperature, and column chromatography gradient elution purification (DCM: MeOH=100:1 to 100:3) was performed to obtain a compound E9C126A24 (227 mg, 73% yield). $^1$H NMR (400 MHz, $CDCl_3$): δ 0.87-0.80 (m, 9H), 1.23-1.28 (m, 44H), 1.38-1.39 (m, 2H), 1.44-1.49 (m, 6H), 1.92-1.95 (m, 1H), 2.02-2.05 (m, 1H), 2.27-2.29 (m, 1H), 2.35-2.43 (m, 6H), 3.76-3.79 (m, 2H), 4.17-4.19 (m, 1H), 4.42-4.44 (m, 1H), 5.16-5.18 (m, 1H). $^{13}$C NMR (100 MHz, $CDCl_3$): δ 14.1, 22.7, 24.5, 25.3, 25.9, 27.1, 29.3, 29.6, 29.9, 30.7, 31.8, 31.9, 32.4, 32.6, 33.2, 39.7, 52.8, 56.8, 65.5, 70.7, 173.1. ESI-MS calculated for $C_{39}H_{76}NO_4^+$ $[M+H]^+$ 622.6, found 622.9.

Embodiment 20: In-Vitro Evaluation of Amino Lipid Compound as mRNA Vector

Cell line: HeLa cell line

Culture medium: 1640 (Lipofectamine3000) supplemented with 10% fetal calf serum

Screening form: 96-well plate cell transfection

Detection: fluorescence intensity detection by a multifunctional microplate reader. According to manufacturer's Instructions, Lipofectamine3000 was used as a positive control group.

Method: an 8-channel pipette was used for sample addition. The shown content is the content of a single well of a 96-well plate.

1. Synthesis was performed with reference to a route in Embodiment 17 and Embodiment 19 to obtain a serious of amino lipid compounds. The amino lipid compounds were mixed with DSPC, cholesterol and PEG2000-DMG according to a mole ratio of 47.5:10:41:1.5 in absolute ethyl alcohol. The Luc-mRNA was dissolved into a sodium acetate buffer solution (25 nM, pH=5.0). The mixed lipid solution was taken out by a multi-channel pipette tip, and was added into the Luc-mRNA solution to be sufficiently mixed. A proportion ratio of the ethyl alcohol solution to the sodium acetate buffer solution (25 nM, pH=5.0) was controlled to be 1:3, and a nanoparticle solution was prepared. The mass ratio of the amino lipid compound to luciferase mRNA (Luc mRNA) was about 10:1, and the mRNA consumption in each well was 100 ng.

2. After the lipid nanoparticle solution was incubated for 30 min at a room temperature, 100 μL of fresh resuspended HeLa cells ($1\times10^4$ cells) were added into each well of a 96-well all-white ELISA plate. Then, the lipid nanoparticle solution was added into the 96-well plate (10 μL for each well) by a pipette. The solution was placed into a 37° C. incubator containing 5% $CO_2$ to be incubated.

3. After 16 h to 20 h of cell initial transfection, a substrate ONE-Glo™ Luciferase was added into cells at 100 μL/well, and after 2 min, detection was performed by a multifunctional or multimode microplate reader.

4. The relative transfection efficiency was calculated as follows:

Relative transfection efficiency (%)=fluorescence intensity of LNP/fluorescence intensity of Lipofectamine3000×100%.

Result: the transfection efficiency of parts of compounds on Luc-mRNA of the HeLa cells is shown in Table 8.

TABLE 8

| relative transfection efficiency of 462 kinds of compounds on mRNA of the HeLa cells | | | | | | |
|---|---|---|---|---|---|---|
| | A9 | A11 | A12 | A16 | A23 | A24 |
| E3C116 | 1.2 | 3.2 | 0.9 | 0.7 | 0.7 | 0.8 |
| E5C104 | 1.5 | 1.3 | 0.7 | 0.8 | 0.9 | 0.9 |
| E5C106 | 0.8 | 0.9 | 0.6 | 0.5 | 0.4 | 0.6 |
| E5C109 | 1.1 | 0.5 | 0.4 | 0.3 | 0.5 | 0.4 |
| E5C111 | 0.8 | 1.2 | 0.7 | 0.9 | 0.5 | 0.3 |
| E5C114 | 1.4 | 2.1 | 0.5 | 0.4 | 0.4 | 0.6 |
| E5C115 | 1.2 | 6.1 | 0.9 | 0.7 | 0.5 | 0.5 |
| E5C116 | 1.2 | 3.0 | 0.8 | 0.6 | 0.6 | 0.5 |
| E5C119 | 1.1 | 0.8 | 0.6 | 0.4 | 0.9 | 0.2 |
| E5C123 | 0.7 | 0.8 | 0.6 | 0.3 | 0.2 | 0.5 |
| E5C126 | 0.4 | 0.5 | 0.1 | 0.1 | 0.4 | 0.2 |
| E5C128 | 1.2 | 1.5 | 0.8 | 0.9 | 0.8 | 0.4 |
| E5C131 | 0.3 | 0.1 | 0.4 | 0.2 | 0.4 | 0.5 |
| E5C135 | 0.9 | 0.4 | 0.41 | 0.3 | 0.6 | 0.6 |
| E7C104 | 1.3 | 0.9 | 0.7 | 0.5 | 0.6 | 0.1 |
| E7C106 | 1.1 | 0.3 | 0.6 | 0.5 | 0.6 | 0.3 |
| E7C109 | 0.5 | 1.1 | 0.5 | 0.8 | 0.7 | 0.2 |
| E7C111 | 0.1 | 0.2 | 0.9 | 0.7 | 0.7 | 0.2 |
| E7C114 | 4.6 | 5.9 | 0.9 | 0.7 | 0.5 | 0.4 |
| E7C115 | 1.6 | 8.3 | 1.0 | 0.9 | 0.3 | 0.4 |
| E7C116 | 1.1 | 5.0 | 0.6 | 0.8 | 0.3 | 0.5 |
| E7C119 | 0.7 | 0.8 | 1.0 | 0.7 | 0.9 | 0.2 |
| E7C123 | 1.3 | 0.9 | 0.7 | 0.4 | 0.3 | 0.2 |
| E7C126 | 0.6 | 1.1 | 0.4 | 0.2 | 0.5 | 0.1 |
| E7C128 | 1.00 | 1.3 | 0.8 | 0.7 | 0.4 | 0.6 |
| E7C131 | 0.2 | 0.4 | 0.2 | 0.1 | 0.2 | 0.2 |
| E7C135 | 0.8 | 0.8 | 0.7 | 0.5 | 0.4 | 0.2 |
| E8C104 | 1.6 | 0.9 | 0.2 | 0.3 | 0.5 | 0.3 |
| E8C106 | 0.9 | 0.4 | 0.5 | 0.3 | 0.6 | 0.5 |
| E8C109 | 1.6 | 0.3 | 0.6 | 0.8 | 0.6 | 0.7 |
| E8C111 | 1.3 | 0.7 | 0.3 | 0.2 | 0.4 | 0.9 |
| E8C114 | 2.9 | 4.8 | 0.4 | 0.3 | 0.5 | 0.3 |
| E8C115 | 1.7 | 6.2 | 0.9 | 0.9 | 0.7 | 0.6 |
| E8C116 | 1.2 | 3.1 | 0.7 | 0.8 | 0.2 | 0.5 |
| E8C119 | 0.9 | 0.5 | 0.5 | 0.3 | 0.7 | 0.2 |
| E8C123 | 0.8 | 2.0 | 0.6 | 0.4 | 0.3 | 0.4 |
| E8C126 | 0.3 | 0.9 | 0.8 | 0.7 | 0.6 | 0.6 |
| E8C128 | 2.1 | 1.0 | 0.9 | 0.6 | 0.4 | 0.4 |
| E8C131 | 0.8 | 0.8 | 0.5 | 0.2 | 0.3 | 0.3 |
| E8C135 | 0.9 | 0.5 | 0.6 | 0.5 | 0.5 | 0.2 |
| E9C104 | 1.5 | 1.8 | 0.6 | 0.6 | 0.8 | 0.4 |
| E9C106 | 0.7 | 0.5 | 0.5 | 0.5 | 0.6 | 0.5 |
| E9C109 | 1.8 | 1.6 | 0.8 | 0.5 | 0.6 | 0.5 |
| E9C111 | 0.9 | 1.3 | 0.6 | 0.7 | 0.4 | 0.3 |
| E9C114 | 3.6 | 4.9 | 0.9 | 0.9 | 0.8 | 0.6 |
| E9C115 | 6.0 | 7.5 | 1.0 | 0.8 | 0.7 | 0.8 |
| E9C116 | 1.1 | 4.7 | 0.4 | 1.0 | 0.3 | 0.3 |
| E9C119 | 0.9 | 0.9 | 0.8 | 0.5 | 0.4 | 0.6 |
| E9C123 | 0.4 | 2.4 | 0.6 | 0.3 | 0.5 | 0.3 |
| E9C126 | 0.6 | 0.4 | 0.3 | 0.4 | 0.3 | 0.3 |
| E9C128 | 1.8 | 1.6 | 0.8 | 0.5 | 0.4 | 0.2 |
| E9C131 | 0.6 | 0.5 | 0.4 | 0.6 | 0.5 | 0.4 |
| E9C135 | 0.7 | 0.7 | 0.8 | 0.6 | 0.3 | 0.2 |
| E10C104 | 0.5 | 0.4 | 0.6 | 0.5 | 0.3 | 0.5 |
| E10C106 | 1.6 | 0.6 | 0.5 | 0.5 | 0.4 | 0.4 |
| E10C109 | 0.7 | 1.1 | 0.9 | 0.7 | 0.7 | 0.8 |
| E10C111 | 1.1 | 0.5 | 0.7 | 0.4 | 0.7 | 0.5 |
| E10C114 | 1.2 | 2.5 | 0.9 | 0.8 | 0.7 | 0.2 |
| E10C115 | 1.2 | 2.7 | 0.7 | 0.6 | 0.6 | 0.8 |
| E10C119 | 0.3 | 0.9 | 0.8 | 0.5 | 0.3 | 0.4 |
| E10C123 | 0.6 | 0.7 | 0.4 | 0.7 | 0.4 | 0.2 |
| E10C126 | 0.4 | 0.8 | 0.6 | 0.6 | 0.9 | 0.5 |
| E10C128 | 1.1 | 1.4 | 0.2 | 0.3 | 0.2 | 0.4 |
| E10C131 | 0.5 | 0.5 | 0.6 | 0.5 | 0.8 | 0.1 |
| E10C135 | 0.9 | 0.6 | 0.7 | 0.5 | 0.7 | 0.6 |
| E11C104 | 0.7 | 0.9 | 0.6 | 0.8 | 0.5 | 0.5 |
| E11C106 | 0.8 | 0.7 | 0.8 | 0.5 | 0.4 | 0.3 |
| E11C109 | 1.3 | 1.4 | 0.3 | 0.8 | 0.5 | 0.4 |
| E11C111 | 0.5 | 0.6 | 0.5 | 0.6 | 0.8 | 0.6 |
| E11C114 | 1.6 | 1.9 | 0.9 | 0.3 | 0.6 | 0.5 |
| E11C115 | 1.3 | 1.8 | 0.6 | 0.7 | 0.5 | 0.6 |
| E11C119 | 0.8 | 0.8 | 0.7 | 0.5 | 0.5 | 0.4 |
| E11C123 | 0.9 | 0.8 | 0.9 | 0.8 | 0.6 | 0.5 |
| E11C126 | 1.5 | 0.9 | 0.8 | 0.5 | 0.6 | 0.3 |
| E11C128 | 1.1 | 1.2 | 0.9 | 0.8 | 0.3 | 0.7 |
| E11C131 | 0.2 | 0.7 | 0.4 | 0.5 | 0.3 | 0.3 |
| E11C135 | 0.4 | 0.3 | 0.6 | 0.6 | 0.5 | 0.2 |

TABLE 8-continued

Embodiment 21: Transfection of Lipid Nanoparticles Prepared from Amino Compounds on BMDC Primary Cells Preparation method: the same as that in Embodiment 17.

Animal preparation: 6-week-old female C57BL/6 mice with the body weight about 20 g were selected. A feeding environment was an SPF stage feeding room. Animal tests were strictly performed according to the guide of the national health institute and the animal ethics requirements.

Cell acquisition: C57BL/6 mice were killed through cervical dislocation, and were soaked for 5 min in 75% ethyl alcohol. Dissection was performed to obtain thigh and calf tibiae of the mice. Attached muscles were removed to expose sclerotin. Then, bone marrow in tibiae was blown out by using a 1 mL injector sucked with PBS. After the bone marrow was blown away, impurities were filtered away by a 50 μm filter screen. A red blood cell lysis buffer (3-4 mL) was added into an obtained filtrate. Then, after placement for 5 min, 800 g centrifugation was performed for 5 min to remove a supernatant. The obtained cells were placed into a 1640 culture medium (containing 10% fetal calf serum, 20 ng/mL GMCSF and 10 ng/mL IL4) to be resuspended, and were inoculated into a 6-well plate at an inoculation density of 100000 cells/ml culture medium. The materials were placed into a 37° C. cell incubator containing 5% $CO_2$. Half liquid change was performed once every 2 days. Suspended cells and loose wall attached cells were collected on the seventh day, and were inoculated to a 96-well all-white ELISA plate at the inoculation density of 20000 cells per well, and the volume of a culture medium was 100 μL.

Cell transfection: lipid nanoparticles coated with luciferase mRNA were added into a 96-well white ELISA plate laid with primary cells. The adding volume of the mRNA lipid nanoparticles in each well was controlled to be 10 μL. Then, the materials were put into a 37° C. incubator containing 5% $CO_2$ for 16 h.

Transfection efficiency detection: 20 μL of a substrate ONE-Glo™ Luciferase was added into each well of a 96-well all-white ELISA plate, and after 1 min, detection was performed by a multifunctional or multimode microplate reader. The expression intensity of the LucmRNA transfection of representative amino lipid compounds on BMDC was as shown in Table 9. DLin-MC3 was used as a control, a plurality of amino lipids had similar expression intensities to MC3, and a plurality of amino lipids had the expression intensities obviously superior to those of the positive control.

TABLE 9
| Serial number | Serial number of amino lipid | Structure | Fluorescence intensity |
|---|---|---|---|
| Expression intensity of transfection of 65 amino lipid compounds on BMDC | | | |
| 1 | E3C116A11 | 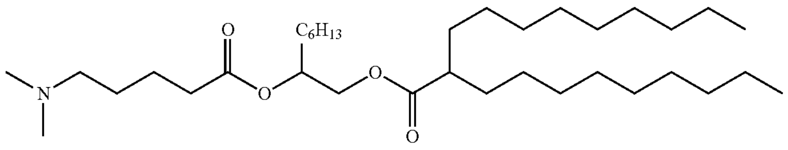 | 4.4E+04 |
| 2 | E5C104A9 | 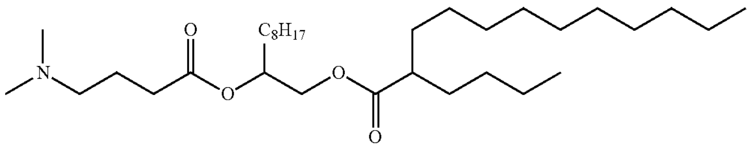 | 5.2E+04 |
| 3 | E5C109A9 | 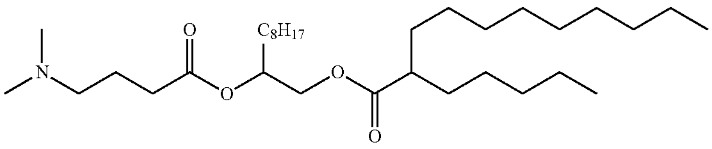 | 3.9E+03 |
| 4 | E5C114A9 | 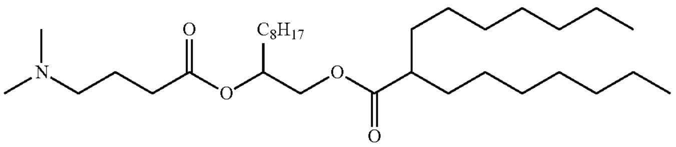 | 8.6E+03 |
| 5 | E5C115A9 | 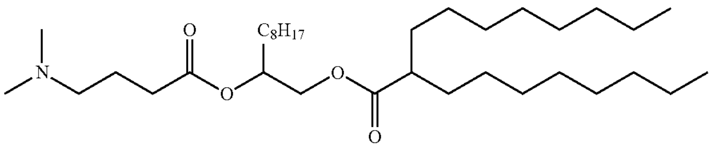 | 2.7E+04 |
| 6 | E5C119A9 | 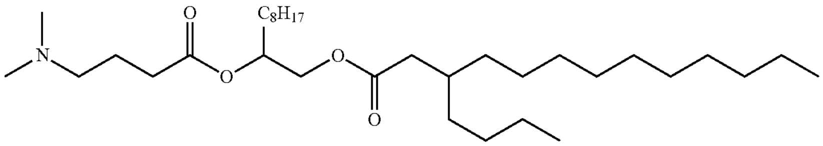 | 4.1E+04 |
| 7 | E5C128A9 | 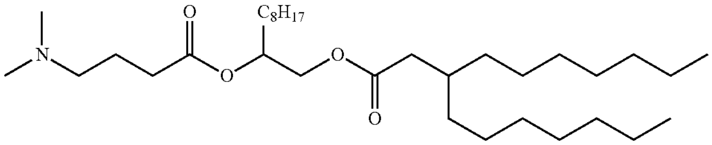 | 3.9E+04 |
| 8 | E5C104A11 | 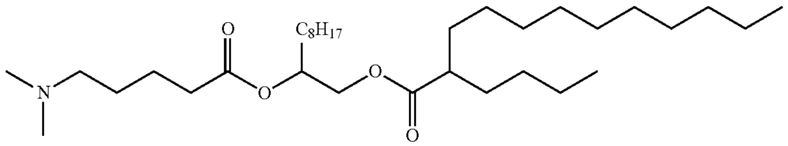 | 4.0E+04 |
| 9 | E5C114A11 | 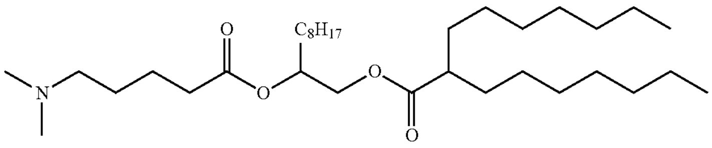 | 4.6E+04 |

TABLE 9-continued
Expression intensity of transfection of 65 amino lipid compounds on BMDC
| Serial number | Serial number of amino lipid | Structure | Fluorescence intensity |
| --- | --- | --- | --- |
| 10 | E5C115A11 | 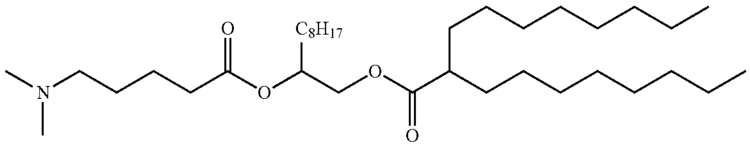 | 1.1E+05 |
| 11 | E5C116A11 | 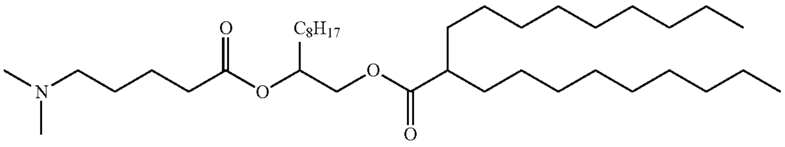 | 6.2E+04 |
| 12 | E5C128A11 | 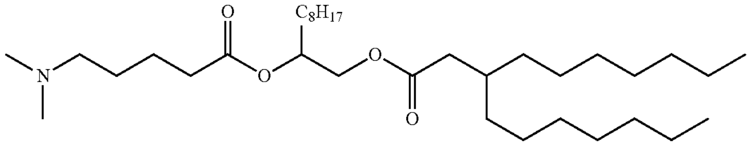 | 4.3E+04 |
| 13 | E7C104A9 | 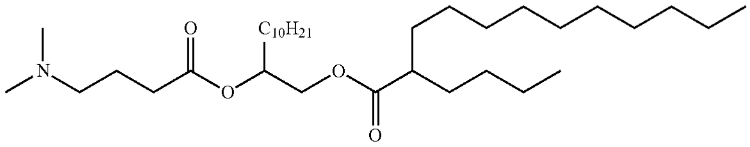 | 3.9E+04 |
| 14 | E7C106A9 | 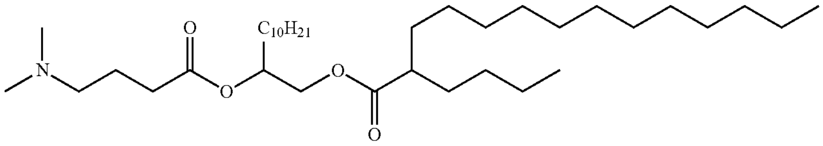 | 3.9E+04 |
| 15 | E7C114A9 | 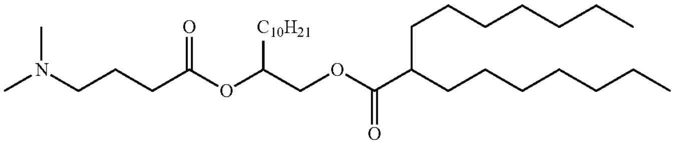 | 6.6E+04 |
| 16 | E7C115A9 | 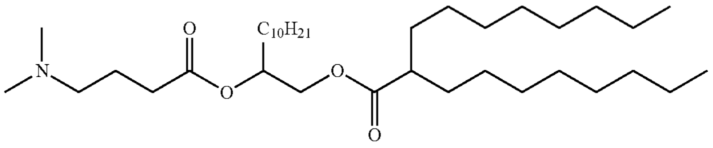 | 5.6E+04 |
| 17 | E7C123A9 | 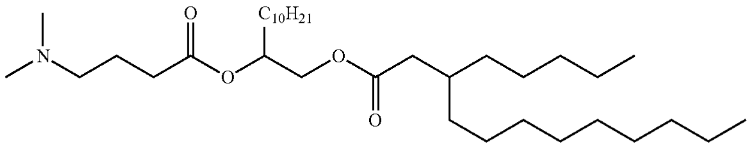 | 4.3E+04 |
| 18 | E7C128A9 | 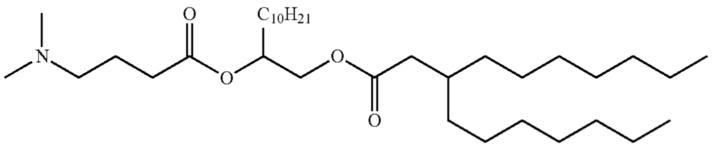 | 3.5E+04 |

TABLE 9-continued
| Serial number | Serial number of amino lipid | Structure | Fluorescence intensity |
|---|---|---|---|
| | | Expression intensity of transfection of 65 amino lipid compounds on BMDC | |
| 19 | E7C114A11 | 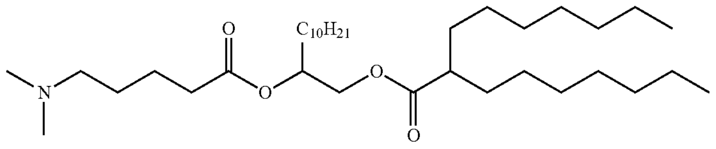 | 9.9E+04 |
| 20 | E7C115A11 | 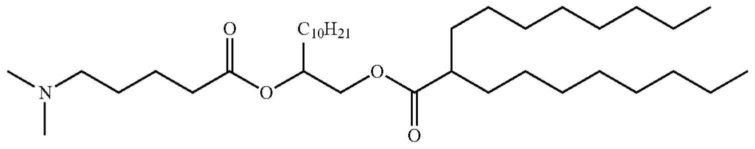 | 2.4E+05 |
| 21 | E7C116A11 | 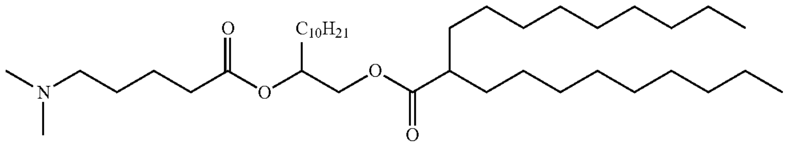 | 9.2E+04 |
| 22 | E7C126A11 | 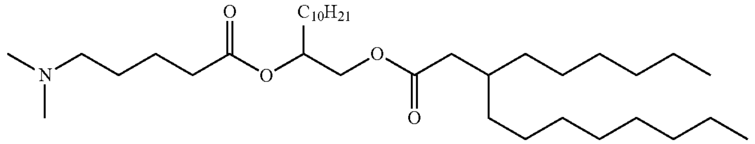 | 3.9E+04 |
| 23 | E7C128A11 | 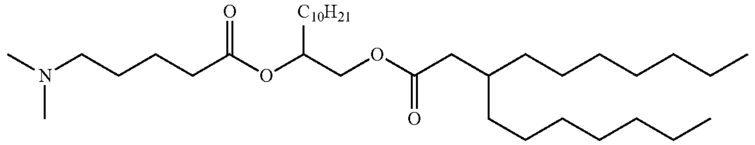 | 3.6E+04 |
| 24 | E8C104A9 | 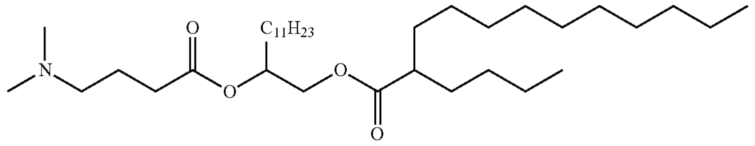 | 3.7E+04 |
| 25 | E8C109A9 | 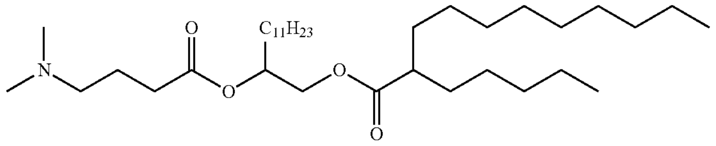 | 4.8E+04 |
| 26 | E8C111A9 | 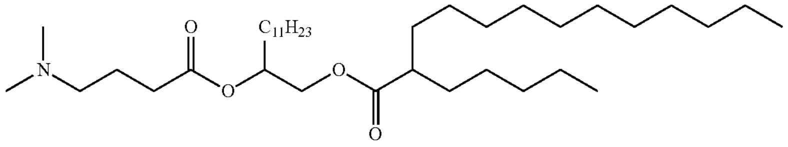 | 4.6E+04 |
| 27 | E8C114A9 | 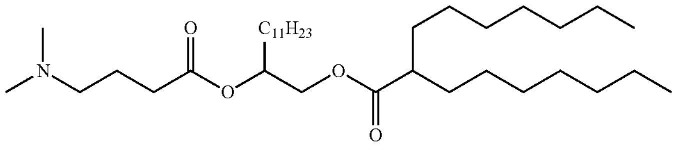 | 6.8E+04 |

TABLE 9-continued
| Expression intensity of transfection of 65 amino lipid compounds on BMDC | | | |
|---|---|---|---|
| Serial number | Serial number of amino lipid | Structure | Fluorescence intensity |
| 28 | E8C115A9 | 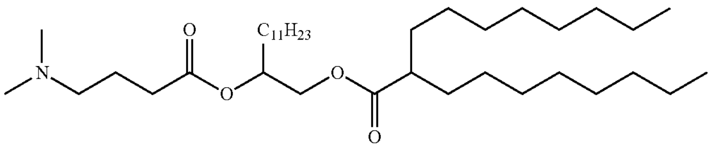 | 6.0E+04 |
| 29 | E8C128A9 | 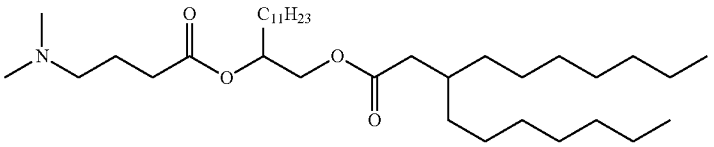 | 3.9E+04 |
| 30 | E8C114A11 | 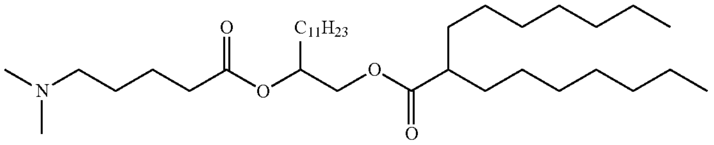 | 1.3E+05 |
| 31 | E8C115A11 | 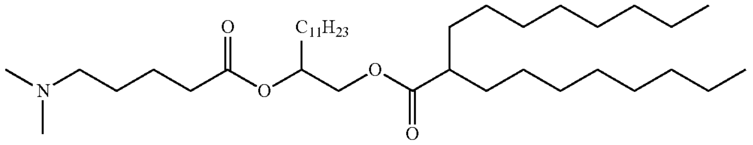 | 1.9E+05 |
| 32 | E8C116A11 | 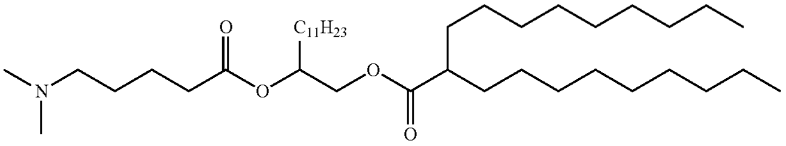 | 5.0E+04 |
| 33 | E8C123A11 | 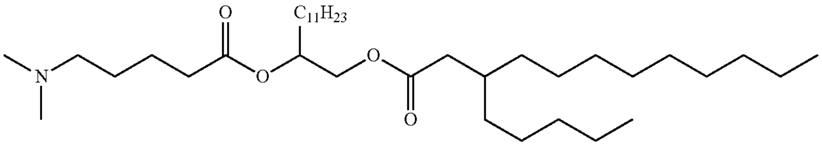 | 7.1E+04 |
| 34 | E8C128A11 | 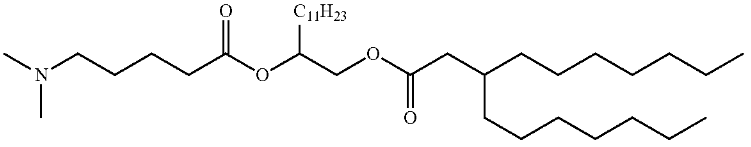 | 3.5E+04 |
| 35 | E9C104A9 | 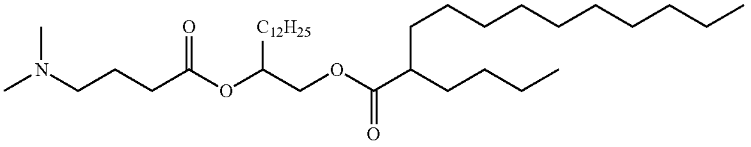 | 3.6E+04 |
| 36 | E9C109A9 | 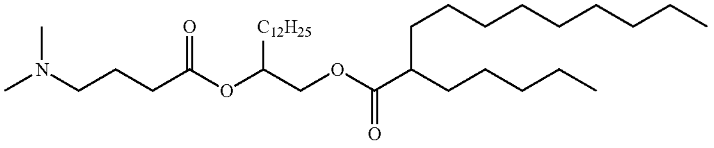 | 3.6E+04 |

TABLE 9-continued
| Expression intensity of transfection of 65 amino lipid compounds on BMDC | | | |
|---|---|---|---|
| Serial number | Serial number of amino lipid | Structure | Fluorescence intensity |
| 37 | E9C114A9 | 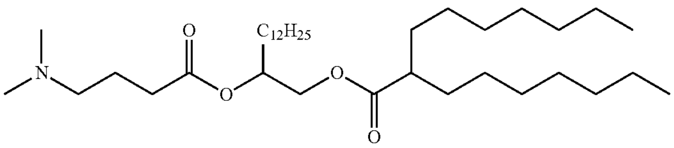 | 9.1E+04 |
| 38 | E9C115A9 | 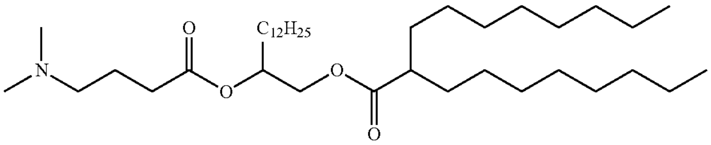 | 1.4E+05 |
| 39 | E9C128A9 | 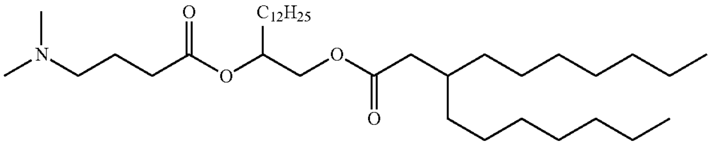 | 3.7E+04 |
| 40 | E9C104A11 | 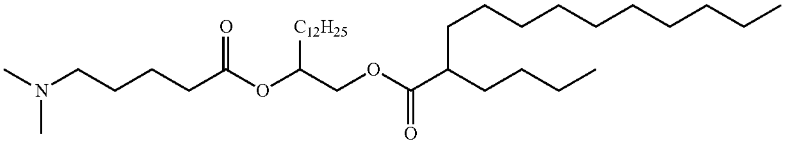 | 4.4E+04 |
| 41 | E9C109A11 | 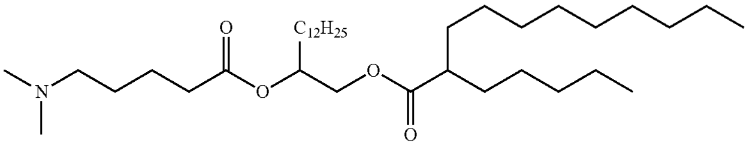 | 3.6E+04 |
| 42 | E9C111A11 | 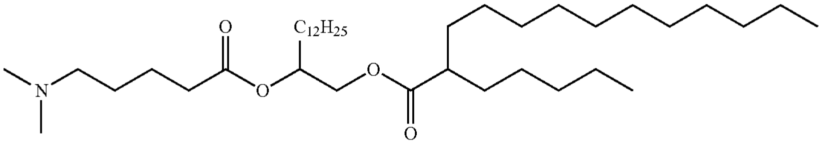 | 3.9E+04 |
| 43 | E9C114A11 | 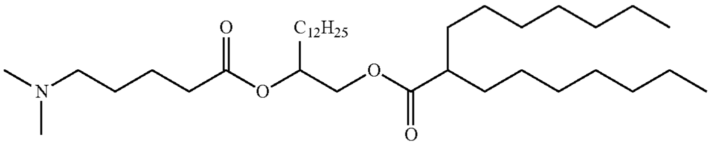 | 8.5E+04 |
| 44 | E9C115A11 | 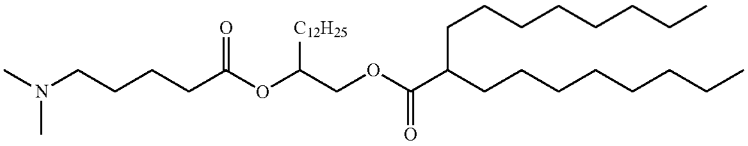 | 1.9E+05 |
| 45 | E9C116A11 | 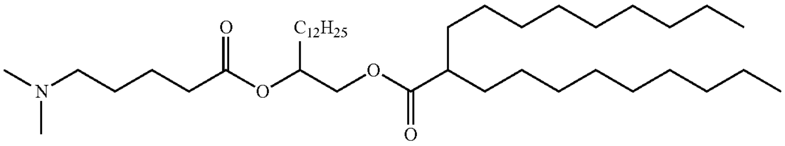 | 7.6E+04 |

TABLE 9-continued
Expression intensity of transfection of 65 amino lipid compounds on BMDC
| Serial number | Serial number of amino lipid | Structure | Fluorescence intensity |
|---|---|---|---|
| 46 | E9C123A11 | 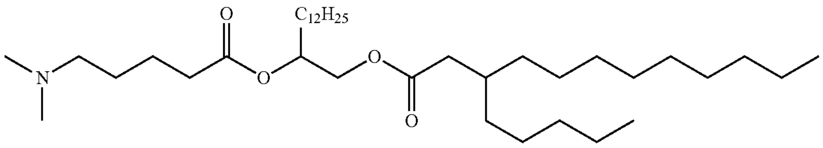 | 5.1E+04 |
| 47 | E9C128A11 | 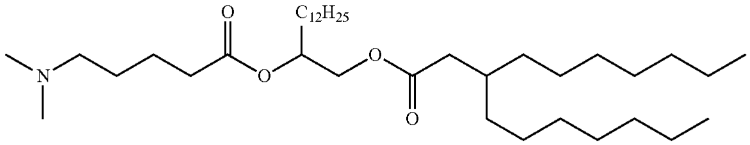 | 3.5E+04 |
| 48 | E10C106A9 | 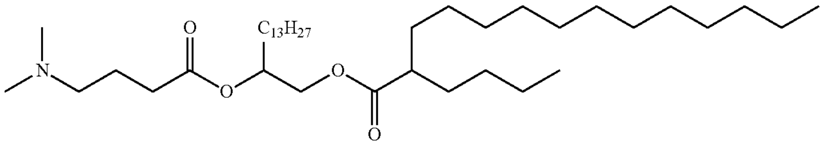 | 4.2E+04 |
| 49 | E10C111A9 | 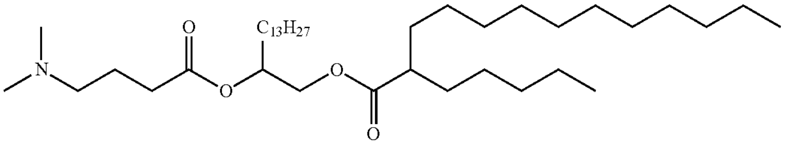 | 3.7E+04 |
| 50 | E10C114A9 | 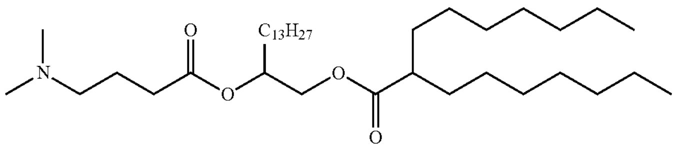 | 4.3E+04 |
| 51 | E10C115A9 | 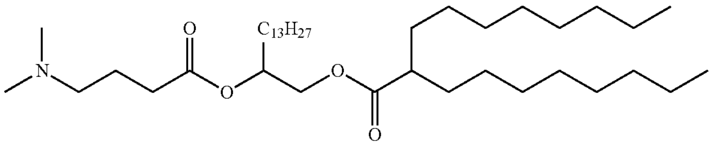 | 4.4E+04 |
| 52 | E10C128A9 | 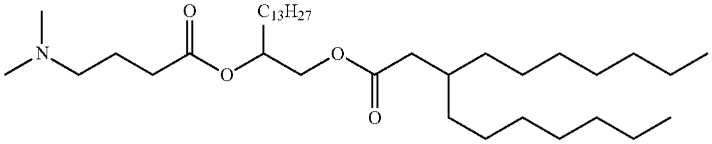 | 3.8E+04 |
| 53 | E10C109A11 | 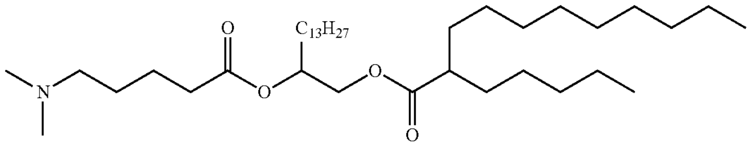 | 3.5E+04 |
| 54 | E10C114A11 | 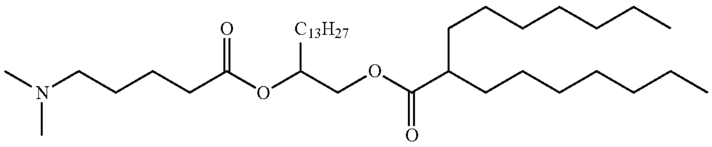 | 7.6E+04 |

TABLE 9-continued
Expression intensity of transfection of 65 amino lipid compounds on BMDC
| Serial number | Serial number of amino lipid | Structure | Fluorescence intensity |
|---|---|---|---|
| 55 | E10C115A11 | 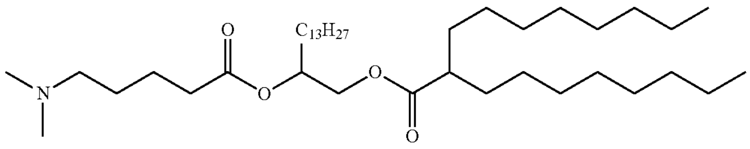 | 8.2E+04 |
| 56 | E10C128A11 | 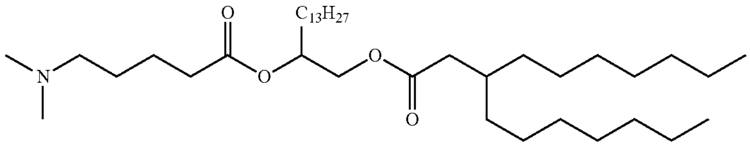 | 4.7E+04 |
| 57 | E11C109A9 | 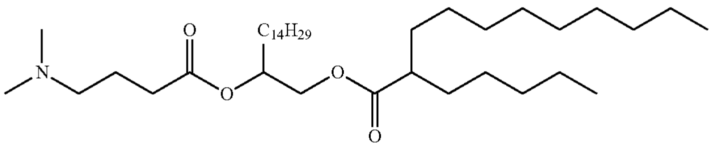 | 4.3E+04 |
| 58 | E11C114A9 | 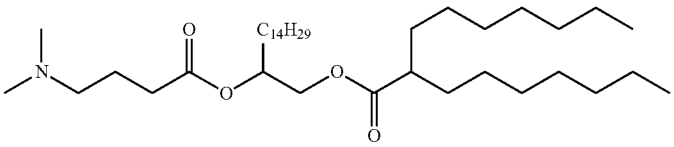 | 4.5E+04 |
| 59 | E11C115A9 | 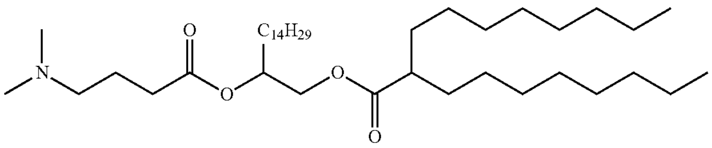 | 4.9E+04 |
| 60 | E11C126A9 | 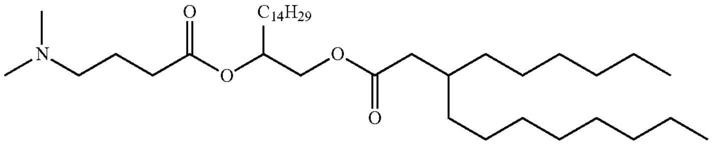 | 3.6E+04 |
| 61 | E11C128A9 | 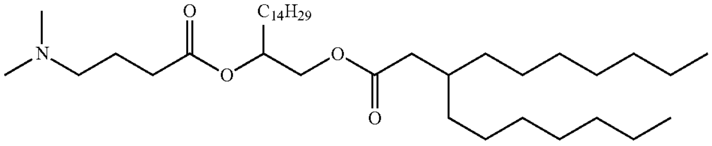 | 3.9E+04 |
| 62 | E11C109A11 | 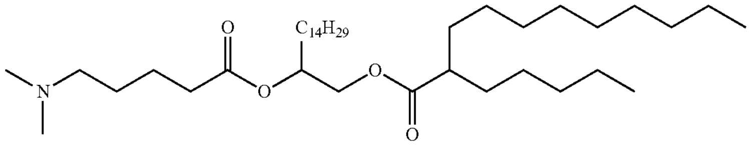 | 4.8E+04 |
| 63 | E11C114A11 | 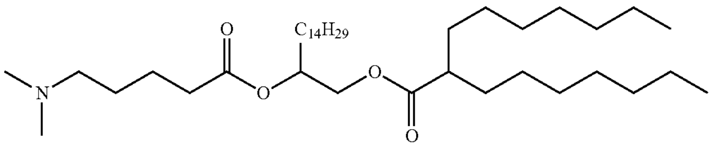 | 6.5E+04 |

TABLE 9-continued

Expression intensity of transfection of 65 amino lipid compounds on BMDC

| Serial number | Serial number of amino lipid | Structure | Fluorescence intensity |
|---|---|---|---|
| 64 | E11C115A11 | 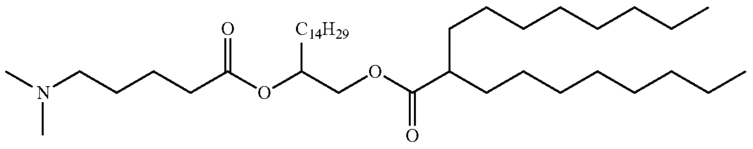 | 6.3E+04 |
| 65 | E11C128A11 | 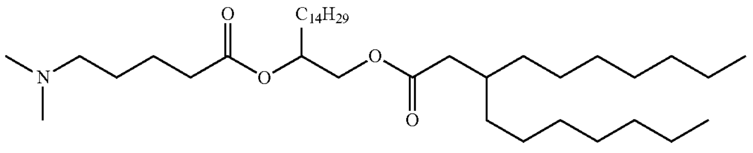 | 4.2E+04 |

Embodiment 22: Evaluation of Luciferase mRNA In-Vivo Delivery Performance of Lipid Nanoparticles Prepared from Amino Lipid Compound 1. Preparation of Lipid Nanoparticles The amino lipid compounds of the disclosure, neutral lipids (such as DSPC, DOPE and cholesterin) and polyethylene glycolated lipids (such as PEG2000-DMG and PEG2000-DSPE) were mixed in absolute ethyl alcohol according to an optimized mole ratio. The obtained ethyl alcohol solution and a sodium acetate buffer solution (25 mM, pH=5.0) dissolved with Luc-mRNA were mixed according to a volume ratio of 1:3 by using a micro-fluidic preparation system to prepare a coarse solution of the lipid nanoparticles. Then, the coarse solution was dialyzed for 6 h under the condition of 1×PBS and temperature control at 4° C. by using a dialysis cassettes or box (MWCO 20,000). Before use, filtration was performed by a 0.22 μm microporous filtering membrane. A mass ratio of the amino lipid compound to luciferase mRNA (Luc mRNA) was about 10:1.

Expression of Lipid Nanoparticles

Expression of particle size: the particle size and PDI of the prepared lipid nanoparticles were measured through Zetasizer Nano-ZSZEN3600. 20 μL of the LNP solution was taken for particle size measurement. Three times were performed and each time lasted for 30 s.

Encapsulation efficiency determination: the determination was performed with the reference to a RiboGreen RNA assay kit standard procedure.

TABLE 10

Characterization data of LNP prepared from representative amino lipid compounds

| Serial number | Serial number of amino lipid | Z-Average (d · nm) | PDI | Encapsulation efficiency (%) |
|---|---|---|---|---|
| LNP-48 | E3C116A11 | 102.4 | 0.10 | 88.9 |
| LNP-49 | E5C109A9 | 115.7 | 0.06 | 91.8 |
| LNP-50 | E5C114A9 | 116.3 | 0.13 | 95.9 |
| LNP-51 | E5C115A9 | 118.4 | 0.06 | 97.2 |
| LNP-52 | E5C128A9 | 114.2 | 0.13 | 93.9 |
| LNP-53 | E5C114A11 | 116.0 | 0.10 | 95.4 |
| LNP-54 | E5C115A11 | 116.9 | 0.07 | 97.5 |

TABLE 10-continued

Characterization data of LNP prepared from representative amino lipid compounds

| Serial number | Serial number of amino lipid | Z-Average (d · nm) | PDI | Encapsulation efficiency (%) |
|---|---|---|---|---|
| LNP-55 | E5C116A11 | 108.3 | 0.06 | 94.8 |
| LNP-56 | E7C114A9 | 124.6 | 0.12 | 94.9 |
| LNP-57 | E7C115A9 | 117.9 | 0.08 | 95.5 |
| LNP-58 | E7C123A9 | 118.2 | 0.08 | 92.4 |
| LNP-59 | E7C114A11 | 104.5 | 0.04 | 94.3 |
| LNP-60 | E7C115A11 | 112.7 | 0.06 | 95.5 |
| LNP-61 | E7C116A11 | 105.6 | 0.08 | 93.6 |
| LNP-62 | E7C126A11 | 109.6 | 0.2 | 90.2 |
| LNP-63 | E8C114A9 | 114.0 | 0.07 | 94.0 |
| LNP-64 | E8C115A9 | 119.1 | 0.10 | 95.3 |
| LNP-65 | E8C114A11 | 113.7 | 0.07 | 93.1 |
| LNP-66 | E8C115A11 | 114.6 | 0.10 | 95.6 |
| LNP-67 | E8C116A11 | 107.2 | 0.11 | 93.5 |
| LNP-68 | E8C123A11 | 115.4 | 0.04 | 94.9 |
| LNP-69 | E9C104A9 | 119.9 | 0.06 | 92.3 |
| LNP-70 | E9C114A9 | 125.1 | 0.08 | 91.5 |
| LNP-71 | E9C115A9 | 116.9 | 0.04 | 94.2 |
| LNP-72 | E9C114A11 | 105.5 | 0.06 | 96.1 |
| LNP-73 | E9C115A11 | 123.3 | 0.11 | 90.3 |
| LNP-74 | E9C116A11 | 110.8 | 0.05 | 94.9 |
| LNP-75 | E9C123A11 | 124.5 | 0.09 | 93.7 |
| LNP-76 | E10C114A9 | 121.6 | 0.09 | 94.6 |
| LNP-77 | E10C115A9 | 117.2 | 0.07 | 95.9 |
| LNP-78 | E10C114A11 | 115.9 | 0.13 | 93.7 |
| LNP-79 | E10C115A11 | 113.2 | 0.09 | 96.2 |
| LNP-80 | E11C109A9 | 119.6 | 0.05 | 93.5 |
| LNP-81 | E11C114A9 | 121.0 | 0.04 | 92.0 |
| LNP-82 | E11C115A9 | 126.4 | 0.06 | 94.8 |
| LNP-83 | E11C109A11 | 119.6 | 0.03 | 95.1 |
| LNP-84 | E11C114A11 | 124.1 | 0.08 | 96.6 |
| LNP-85 | E11C115A11 | 116.7 | 0.11 | 94.5 |
| LNP-86 | DLin-MC3 | 139.2 | 0.15 | 94.6 |
| LNP-87 | E7C115A11 | 102.5 | 0.05 | 93.4 |
| LNP-88 | E7C115A11 | 119.9 | 0.06 | 92.3 |
| LNP-89 | E7C115A11 | 128.8 | 0.15 | 94.2 |
| LNP-90 | E7C115A11 | 124.5 | 0.09 | 93.7 |
| LNP-91 | E7C115A11 | 131.4 | 0.09 | 92.6 |

Note: in the above table:

a lipid formulation of LNP-48 to LNP-86 was as follows: amino lipid:DSPC:cholesterol:PEG2000-DMG=47.5:10:41:1.5;

a lipid formulation of LNP-87 was as follows: amino lipid:DOPE:cholesterol:PEG2000-DMG=45:10:43.5:1.5;

a lipid formulation of LNP-88 was as follows: amino lipid:DSPC:DOPS:cholesterol:PEG2000-DMG=50:10:5:38.5:1.5;

a lipid formulation of LNP-89 was as follows: amino lipid:DSPC:DOPC:cholesterol:PEG2000-DMG=45:10:5:38.0:2.0;

a lipid formulation of LNP-90 was as follows: amino lipid:DSPC:DOPE:cholesterol:PEG2000-DSPE=50:10:5:33.5:1.5; and a lipid formulation of LNP-91 was as follows: amino lipid:cholesterol:PEG2000-DSPE=60:35.5:4.5.

2. Animal Tests

Animal preparation: 6-week-old female C57BL/6 mice with the body weight about 20 g were selected. The feeding environment was an SPF stage feeding room. Animal tests were strictly performed according to the guide of the national health institute and the animal ethics requirements.

In-vivo delivery: 9 C57BL/6 mice were randomly selected for each group. According to an mRNA consumption of 0.5 mg/kg, a lipid nanoparticle solution was respectively injected in three administration manners of subcutaneous, intramuscular and tail intravenous injection (3 mice for each administration manner). After 12 h, 200 μL of 10 mg/mL D-luciferin potassium salt was injected into each mice through tail intravenous injection. After 10 min, the mice were placed in an in-vivo living imaging system (in-vivo imaging system 200 series, in-vivo spectrum imaging system), the total fluorescence intensity of each mice was observed, and photos were taken for recording. The expression intensity of the Fluc mRNA delivered by the representative amino lipid compounds in 3 administration manners was as shown in Table 11 to Table 13. DLin-MC3 was used as a control.

TABLE 11

Expression intensity of Luc mRNA delivered by LNP subcutaneous administration of representative amino lipid compounds

| Serial number | Serial number of LNP | Average fluorescence intensity |
|---|---|---|
| 1 | LNP-48 | 8.8E+06 |
| 2 | LNP-52 | 5.1E+07 |
| 3 | LNP-54 | 1.2E+08 |
| 4 | LNP-56 | 5.1E+07 |
| 5 | LNP-59 | 4.6E+07 |
| 6 | LNP-60 | 1.1E+08 |
| 7 | LNP-62 | 3.2E+07 |
| 8 | LNP-65 | 8.3E+07 |
| 9 | LNP-66 | 9.4E+07 |
| 10 | LNP-69 | 2.6E+07 |
| 11 | LNP-70 | 6.2E+07 |
| 12 | LNP-72 | 8.8E+07 |
| 13 | LNP-73 | 5.6E+07 |
| 14 | LNP-76 | 6.7E+07 |
| 15 | LNP-79 | 8.1E+07 |
| 16 | LNP-82 | 9.3E+07 |
| 17 | LNP-83 | 5.5E+07 |
| 18 | LNP-85 | 7.2E+07 |
| 19 | LNP-87 | 1.0E+08 |
| 20 | LNP-90 | 8.9E+07 |

TABLE 12

Expression intensity of Luc mRNA delivered by LNP intramuscular injection administration delivery of representative amino lipid compounds

| Serial number | Serial number of LNP | Average fluorescence intensity |
|---|---|---|
| 1 | LNP-49 | 5.3E+07 |
| 2 | LNP-54 | 1.5E+08 |
| 3 | LNP-55 | 6.4E+07 |
| 4 | LNP-59 | 7.0E+07 |
| 5 | LNP-60 | 1.7E+08 |
| 6 | LNP-61 | 6.1E+07 |
| 7 | LNP-65 | 1.3E+08 |
| 8 | LNP-66 | 9.9E+07 |
| 9 | LNP-68 | 8.6E+07 |
| 10 | LNP-70 | 8.2E+07 |
| 11 | LNP-72 | 7.8E+07 |
| 12 | LNP-73 | 6.4E+07 |
| 13 | LNP-77 | 4.5E+07 |
| 14 | LNP-80 | 4.8E+07 |
| 15 | LNP-81 | 5.9E+07 |
| 16 | LNP-83 | 6.4E+07 |
| 17 | LNP-84 | 8.3E+07 |
| 18 | LNP-85 | 6.8E+07 |
| 19 | LNP-88 | 1.0E+08 |
| 20 | LNP-90 | 9.6E+07 |

TABLE 13

Expression intensity of Luc mRNA delivered by LNP tail intravenous administration delivery of representative amino lipid compounds

| Serial number | Serial number of LNP | Average fluorescence intensity |
|---|---|---|
| 1 | LNP-51 | 3.5E+07 |
| 2 | LNP-53 | 3.3E+07 |
| 3 | LNP-54 | 8.1E+07 |
| 4 | LNP-56 | 6.2E+07 |
| 5 | LNP-58 | 4.7E+07 |
| 6 | LNP-59 | 7.9E+07 |
| 7 | LNP-60 | 1.3E+08 |
| 8 | LNP-64 | 5.4E+07 |
| 9 | LNP-65 | 7.6E+07 |
| 10 | LNP-66 | 8.9E+07 |
| 11 | LNP-70 | 5.4E+07 |
| 12 | LNP-72 | 4.9E+07 |
| 13 | LNP-74 | 2.4E+07 |
| 14 | LNP-78 | 3.8E+07 |
| 15 | LNP-82 | 2.3E+07 |
| 16 | LNP-83 | 9.9E+06 |
| 17 | LNP-85 | 1.4E+07 |
| 18 | LNP-87 | 1.0E+08 |
| 19 | LNP-89 | 8.7E+07 |
| 20 | LNP-91 | 6.3E+06 |

Embodiment 23: In-Vivo Immunity and Tumor Treatment Effect Evaluation of Lipid Nanoparticles Prepared from Amino Lipid Compounds Preparation method: the amino lipid compounds of the disclosure, DSPC, cholesterol and PEG2000-DMG were mixed according to a mole ratio of 50:10:38.5:1.5 in absolute ethyl alcohol. OVA mRNA was dissolved in a sodium acetate buffer solution (50 nM, pH=4.0). The ratio of the ethyl alcohol solution to the acetate buffer solution (50 nM, pH=4.0) was controlled to be 1:3 by using two micro-injection pumps to prepare a coarse solution of the lipid nanoparticles in a micro-fluidic chip. Then, dialysis was performed for 6 h under the conditions of 1×PBS and temperature control at 4° C. by using a dialysis cassettes or box (MWCO 20,000). Before use, filtration was performed by a 0.22 μm microporous filtering membrane. A mass ratio of the amino lipid compound to OVA mRNA was about 8:1.

Animal preparation: 5-6-week-old female C57BL/6 mice with the body weight about 18 to 20 g were selected. The feeding environment was an SPF stage feeding room. Animal tests were strictly performed according to the guide of the national health institute and the animal ethics requirements.

Figure 5:
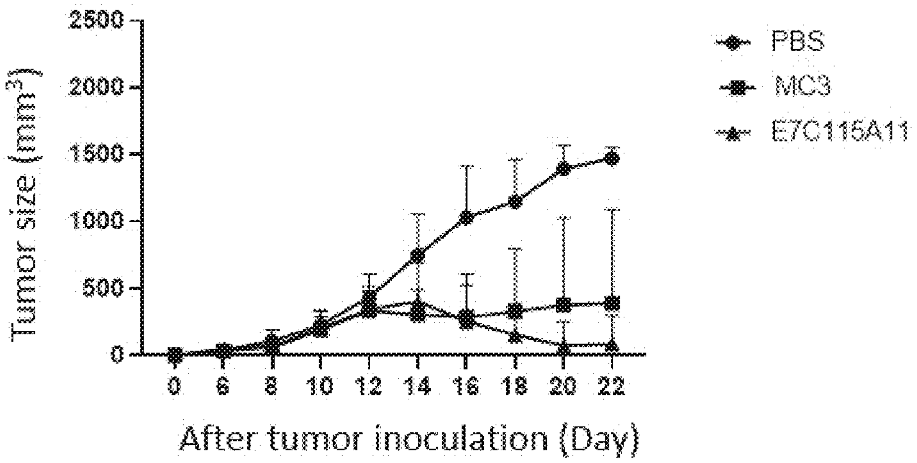
FIG. 5 is a tumor growth curve diagram of tumor-bearing mice after receiving intramuscular injection of OVA mRNA vaccines in Embodiment 23 (LNP assembled by E7C115A11 is used).
Figure 6:
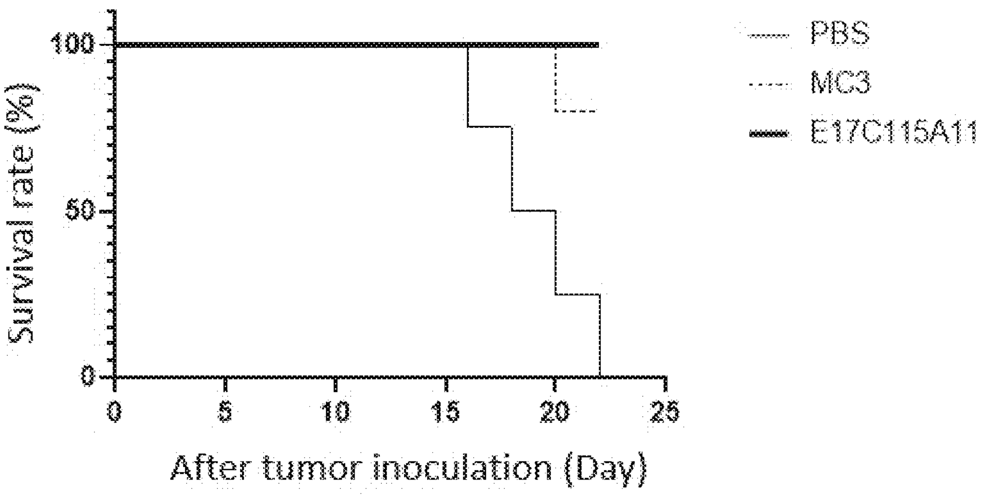
FIG. 6 is a survival curve of tumor-bearing mice after receiving intramuscular injection of OVA mRNA vaccines in Embodiment 23 (LNP assembled by E7C115A11 is used).

In-vivo delivery: B16-OVA melanoma cells ($1.5\times10^5$) were injected to the outer thighs of the mice through subcutaneous injection. When the tumor grew to 50 $mm^3$ (on the about $6^{th}$ or $7^{th}$ day after tumor inoculation), the mice began to inoculated vaccines, the animals were subjected to twice immunization through intramuscular injection of an LNP preparation containing 5 μg OVA-mRNA. An interval between first and second injections was 7 days. The tumor growth was measured for 3 times every week by a digital display calliper, and a calculation formula was 0.5×length×width. When the tumor size reached 1500 $mm^3$, the mice received euthanasia. The tumor growth speed of E7C115A11 was obviously lower than that of MC3 group, 90% of the mice tumors completely disappeared (as shown in FIG. 5), and the survival rate reached 100%, and was obviously superior to that of MC3 group (as shown in FIG. 6).

Embodiment 24: 2-((6-(Dimethylamino)Hexanoyl)Oxy)Dodecyl 2-Hexyldecanoate

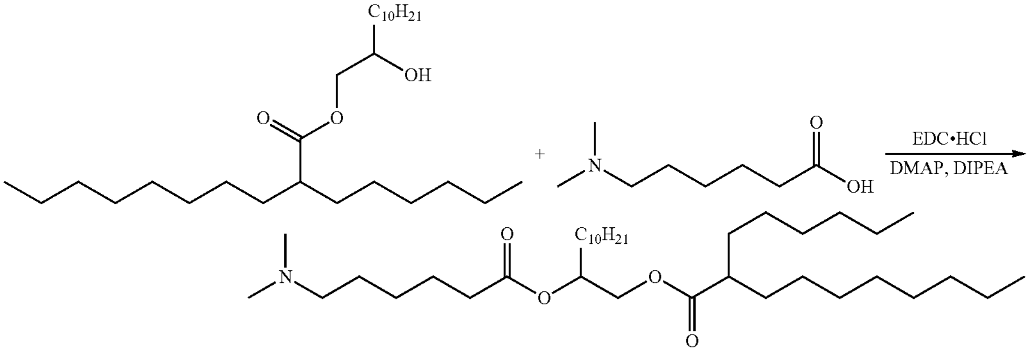

E7C71A12

EDC·HCl (192 mg, 1 mmol), DIPEA (174 μL, 1 mmol), DMAP (3.0 mg, 0.025 mmol), 6-(dimethylamino)hexanoic acid (96 mg, 0.6 mmol), 2-hydroxydodecyl 2-hexyldecanoate (220 mg, 0.5 mmol) and DCM (4 mL) were sequentially added into a 10 mL reaction tube, and the reaction was stirred at room temperature for 3 h to obtain the compound E7C71A12 (216 mg, 74%). $^1H$ NMR (400 MHz, $CDCl_3$): δ 0.86 (t, J=6.5 Hz, 9H), 1.24-1.46 (m, 40H), 1.54-1.68 (m, 8H), 2.27-2.34 (m, 9H), 2.40-2.44 (m, 2H), 4.02 (dd, $J_1$=11.7 Hz, $J_2$=6.1 Hz, 1H), 4.23 (dd, $J_1$=12.2 Hz, $J_2$=3.5 Hz, 1H), 5.03-5.06 (m, 1H). $^{13}C$ NMR (100 MHz, $CDCl_3$): δ 14.1, 22.7, 24.7, 25.3, 26.7, 27.4, 29.3, 29.4, 29.6, 30.7, 31.8, 31.9, 32.7, 34.2, 44.7, 47.0, 61.6, 65.8, 70.7, 173.1, 175.8. ESI-MS calculated for $C_{36}H_{72}NO_4^+$ $[M+H]^+$ 582.5, found 582.5.

E7C71A9

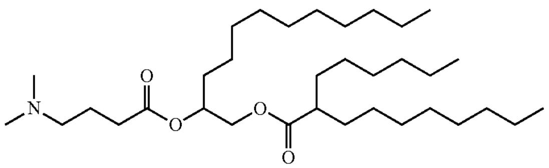

Compound A

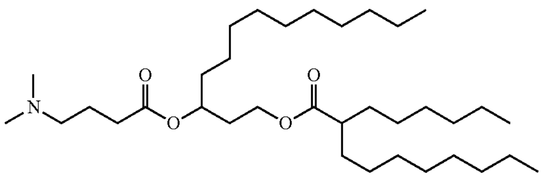

Compound B

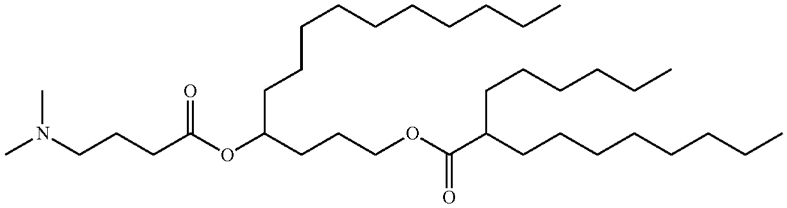

-continued

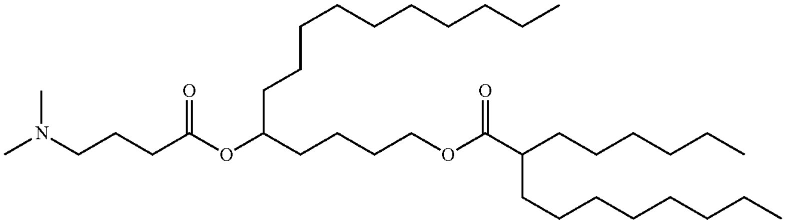

Compound C

The compound E7C71A9 was synthesized according to the procedures described in embodiments 4 and 5 of this patent, while Compound A, Compound B, and Compound C were prepared by reference to the methods reported in the previously published patents. Take the synthesis of Compound A as an example:

The construction of tridecane-1,3-diol (Chemical Abstracts Service number: 39516-29-5) was conducted in two steps using Abstracts Service number: 3-(tert-butyldimethylsilyloxy)-propanal (Chemical 89922-82-7) as the starting material, referring to the method reported in the published patent (U.S. Pat. No. 11,013,696B2).

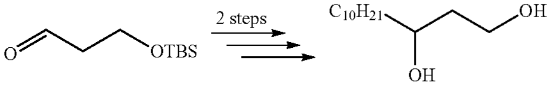

Embodiment 25:3-Hydroxytridecyl 2-Hexyldecanoate

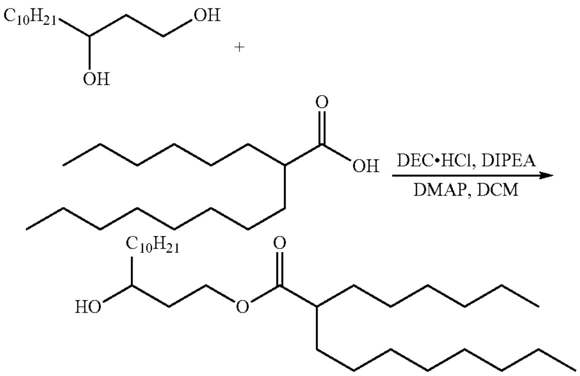

Tridecane-1,3-diol (1.08 g, 5 mmol), 2-hexyldecanoic acid (1.54 g, 6 mmol), EDC·HCl (1.35 g, 7 mmol), DMAP (245 mg, 2 mmol), DIPEA (647 mg, 5 mmol) and DCM (20 mL) were added into a 50 mL round bottom flask charged with a magnetic stirring bar, then the resultant mixture was stirred at room temperature for 12 h. The product 3-hydroxytridecyl 2-hexyldecanoate (1.30 g, 57% yield) was obtained by column chromatography on silica gel through gradient elution purification (hexane:EA=20:1 to 10:1). $^1H$ NMR (400 MHz, $CDCl_3$): δ 0.88 (t, 9H), 1.23-1.27 (m, 36H), 1.38-1.40 (m, 2H), 1.61-1.64 (m, 4H), 1.79-1.82 (m, 2H), 2.11-2.12 (m, 1H), 3.38-3.40 (m, 1H), 4.06 (t, 2H), 4.49 (brs, 1H). ESI-MS calculated for $C_{29}H_{59}O_3$ $[M+H]^+$ 455.4, found 455.5.

Embodiment 26: 3-((4-(Dimethylamino)Butanoyl) Oxy)Tridecyl 2-Hexyldecanoate (Compound A)

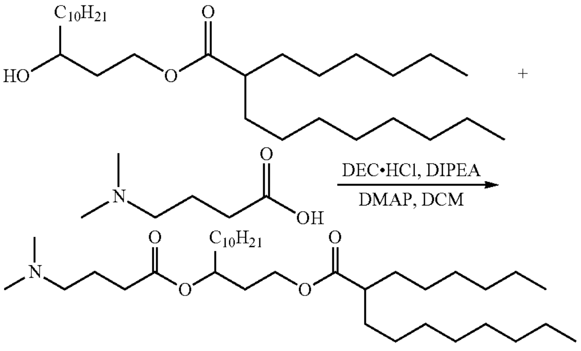

Compound A

EDC·HCl (192 mg, 1 mmol), DIPEA (174 μL, 1 mmol), DMAP (3.0 mg, 0.025 mmol), 3-hydroxytridecyl 2-hexyldecanoate (228 mg, 0.5 mmol), 4-(dimethylamino)butanoic acid (101 mg, 0.6 mmol) and DCM (4 mL) were sequentially added into a 10 mL reaction tube, then reaction was stirred at room temperature for 3 h. The product 3-((4-(dimethylamino)butanoyl)oxy)tridecyl 2-hexyldecanoate (compound A, 227 mg, 80% yield) was obtained by column chromatography on silica gel through gradient elution purification (MeOH:DCM=1:99 to 3:97). $^1H$ NMR (400 MHz, $CDCl_3$): δ 0.88 (t, 9H), 1.22-1.28 (m, 36H), 1.48-1.49 (m, 2H), 1.58-1.61 (m, 4H), 1.86-1.88 (m, 4H), 2.03 (s, 6H), 2.13-2.14 (m, 1H), 2.35 (t, 2H), 3.04 (t, 2H), 4.06 (t, 2H), 4.46-4.47 (m, 1H). $^{13}C$ NMR (100 MHz, $CDCl_3$): & 14.1, 22.7, 23.4, 25.6, 29.3, 29.4, 31.8, 31.9, 32.7, 33.3, 34.2, 44.7, 47.0, 61.0, 61.4, 71.2, 173.1, 175.8. ESI-MS calculated for $C_{35}H_{70}NO_4^+$ $[M+H]^+$ 568.5, found 568.9.

Embodiment 27: In-Vitro Evaluation of Amino Lipid Compounds (E7C71A9, Compound a, Compound B, Compound C) as mRNA Vector Cell line: HeLa cell line Culture medium: 1640 (Lipofectamine3000) supplemented with 10% fetal calf serum Screening form: 96-well plate cell transfection Detection: fluorescence intensity detection by a multi-functional microplate reader. According to manufacturer's instructions, Lipofectamine3000 was used as a positive control group.

Method: a pipette was used for sample addition. The shown content is the content of a single well of a 96-well plate.

1. Synthesis of E7C71A9, Compound A, Compound B, and Compound C was performed as described above. And these four ionizable amino lipid compounds were respectively mixed with DSPC, cholesterol and PEG2000-DMG into absolute ethyl alcohol. according to a mole ratio of 43:10.5:45:1.5, The Luc-mRNA was dissolved into a sodium acetate buffer solution (25 nM, pH=5.0). The mixed lipid solution was taken out by a pipette, and was added into the Luc-mRNA solution to be sufficiently mixed. A proportion ratio of the ethyl alcohol solution to the sodium acetate buffer solution (25 nM, pH=5.0) was controlled to be 1:3, and a nanoparticle solution was prepared. A mass ratio of the amino lipid compound to luciferase mRNA (Luc mRNA) was about 10:1, and the mRNA consumption in each well was 100 ng.

2. After the lipid nanoparticle solution was incubated for 30 min at room temperature, 100 μL of fresh resuspended HeLa cells ($1\times10^4$ cells) were added into each well of a 96-well all-white ELISA plate. Then, the lipid nanoparticle solution was added into the 96-well plate (10 μL for each well) by a pipette. The solution was placed into a 37° C. incubator containing 5% $CO_2$ to be incubated.

3. After 16 h to 20 h of cell initial transfection, a substrate ONE-Glo™ Luciferase was added into cells at 100 μL/well, and after 2 min, detection was performed by a multifunctional or multimode microplate reader.

4. The relative transfection efficiency was calculated as follows:

Relative transfection efficiency (%)=fluorescence intensity of LNP/fluorescence intensity of Lipofectamine3000×100%.

Result: the transfection efficiency of parts of compounds on Luc-mRNA of the HeLa cells is shown in Table 14.

TABLE 14 relative transfection efficiency of the above four compounds on Luc-mRNA of the HeLa cells

| Serial Number of Amino Lipid | Relative Transfection Efficiency |
|---|---|
| E7C71A9 | 2.0 |
| Compound A | 0.62 |
| Compound B | 0.45 |
| Compound C | 0.39 |
| Lip3000 | 1 |

Embodiment 28: Transfection of Lipid Nanoparticles Prepared from the Above Four Amino Compounds on BMDC Primary Cells Preparation method: the same as that described above.

Animal preparation: 6-week-old female C57BL/6 mice with the body weight about 20 g were selected. The feeding environment was an SPF stage feeding room. Animal tests were strictly performed according to the guide of the national health institute and the animal ethics requirements.

Cell acquisition: C57BL/6 mice were killed through cervical dislocation, and were soaked for 5 min in 75% ethyl alcohol. Dissection was performed to obtain thigh and calf tibiae of the mice. Attached muscles were removed to expose sclerotin. Then, bone marrow in tibiae was blown out by using a 1 mL injector sucked with PBS. After the bone marrow was blown away, impurities were filtered away by a 50 μm filter screen. A red blood cell lysis buffer (3-4 mL) was added into an obtained filtrate. Then, after placement for 5 min, 800 g centrifugation was performed for 5 min to remove the supernatant. The obtained cells were placed into a 1640 culture medium (containing 10% fetal calf serum, 20 ng/mL GMCSF and 10 ng/ml IL4) to be resuspended, and were inoculated into a 6-well plate at an inoculation density of 100000 cells/ml culture medium. The materials were placed into a 37° C. cell incubator containing 5% $CO_2$. Half liquid change was performed once every 2 days. Suspended cells and loose wall attached cells were collected on the seventh day, and were per well, and the volume of a culture medium was 100 μL.

Cell transfection: lipid nanoparticles coated with luciferase mRNA were added into a 96-well all-white ELISA plate laid with primary cells. The adding volume of the mRNA lipid nanoparticles in each well was controlled to be 10 μL. Then, the materials were put into a 37° C. incubator containing 5% $CO_2$ for 16 h.

Transfection efficiency detection: 20 μL of a substrate ONE-Glo™ Luciferase was added into each well of a 96-well all-white ELISA plate. After 1 min, detection was performed by a multifunctional or multimode microplate reader. The expression intensity of the LucmRNA transfection of representative amino lipid compounds on BMDC was as shown in Table 15. DLin-MC3 was used as a control.

TABLE 15

Transfection expression intensity of the above four amino lipid compounds on BMDC

| Serial Number of Amino Lipid | Fluorescence intensity |
|---|---|
| E7C71A9 | 8.8E+04 |
| Compound A | 4.9E+04 |
| Compound B | 2.5E+04 |
| Compound C | 9.3E+03 |

The above descriptions are only exemplary embodiments of the disclosure, and are not intended to limit the disclosure. All changes, equivalents, improvements, etc. made within the spirit and principle of the disclosure all fall within the protection scope of the disclosure.

After the reactions were completed, the solution was volatilized at room temperature to dryness, and 15 amino lipid compounds E7C71Ay were obtained. Mass spectrometric detection was performed, and the results were collected as shown in Table 1.

Embodiment 2:2-Hydroxyhexadecyl Dodecanoate

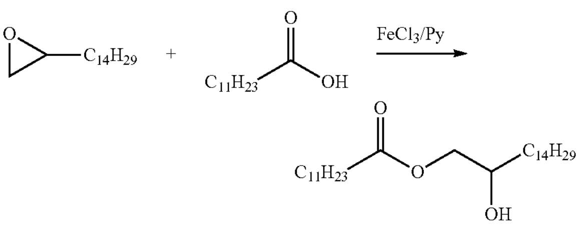

$FeCl_3$ (20 mg, 0.025 mmol), Py (5 μL, 0.0125 mmol), dodecanoic acid (1 g, 5 mmol) and 2-epoxy hexadecane (1.7 mL, 6 mmol) were sequentially added into a 25 (containing 10% fetal calf serum, 20 ng/mL GMCSF and 10 ng/ml IL4) to be resuspended, and were inoculated into a 6-well plate at an inoculation density of 100000 cells/ml culture medium. The materials were placed into a 37° C. cell incubator containing 5% $CO_2$. Half liquid change was performed once every 2 days. Suspended cells and loose wall attached cells were collected on the seventh day, and were inoculated to a 96-well all-white ELISA plate at the inoculation density of 20000 cells per well, and the volume of a culture medium was 100 μL.

Cell transfection: lipid nanoparticles coated with luciferase mRNA were added into a 96-well all-white ELISA plate laid with primary cells. The adding volume of the mRNA lipid nanoparticles in each well was controlled to be 10 μL. Then, the materials were put into a 37° C. incubator containing 5% $CO_2$ for 16 h.

Transfection efficiency detection: 20 μL of a substrate ONE-Glo™ Luciferase was added into each well of a 96-well all-white ELISA plate. After 1 min, detection was performed by a multifunctional microplate reader (Biorek SynergyH1). The expression intensity of the LucmRNA transfection of representative amino lipid compounds on BMDC was as shown in Table 3. DLin-MC3 was used as a control, a plurality of amino lipids had similar expression intensity to MC3, and a plurality of amino lipids had the expression intensity obviously superior to that of the positive control.

Embodiment 14: Evaluation on Luciferase mRNA In-Vivo Delivery Performance of Lipid Nanoparticles Prepared from Amino Lipid Compounds 1. Preparation of Lipid Nanoparticles The amino lipid compounds of the disclosure, neutral lipids (such as DSPC, DOPE and cholesterin) and polyethylene glycolated lipids (such as PEG2000-DMG and PEG2000-DSPE) were mixed according to an optimized mole ratio and were dissolved in absolute ethyl alcohol. The obtained ethyl alcohol solution and a sodium acetate buffer solution (25 mM, pH=5.0) dissolved with Luc-mRNA (TriLink) were mixed according to a volume ratio of 1:3 by using a micro-fluidic preparation system to prepare a coarse solution of the lipid nanoparticles. Then, the coarse solution was dialyzed for 6 h under the condition of 1×PBS and temperature control at 4° C. by a dialysis box (Fisher, MWCO 20,000). Filtration was performed by a 0.22 μm microporous filtering membrane prior to use. A mass ratio of the amino lipid compound to luciferase mRNA (Luc mRNA) was about 10:1.

Characterization of Lipid Nanoparticles

Characterization of particle size: the particle size and PDI of the prepared lipid nanoparticles were measured through Nano-ZSZEN3600 (Malvern). 20 μL of inoculated to a 96-well all-white ELISA plate at the inoculation density of 20000 cells per well, and the volume of a culture medium was 100 μL.

Cell transfection: lipid nanoparticles coated with luciferase mRNA were added into a 96-well white ELISA plate laid with primary cells. The adding volume of the mRNA lipid nanoparticles in each well was controlled to be 10 μL. Then, the materials were put into a 37° C. incubator containing 5% $CO_2$ for 16 h.

Transfection efficiency detection: 20 μL of a substrate ONE-Glo™ Luciferase was added into each well of a 96-well all-white ELISA plate, and after 1 min, detection was performed by a multifunctional microplate reader (Biorek SynergyH1). The expression intensity of the LucmRNA transfection of representative amino lipid compounds on BMDC was as shown in Table 9. DLin-MC3 was used as a control, a plurality of amino lipids had similar expression intensities to MC3, and a plurality of amino lipids had the expression intensities obviously superior to those of the positive control.

Embodiment 22: Evaluation of Luciferase mRNA In-Vivo Delivery Performance of Lipid Nanoparticles Prepared from Amino Lipid Compound 1. Preparation of Lipid Nanoparticles The amino lipid compounds of the disclosure, neutral lipids (such as DSPC, DOPE and cholesterin) and polyethylene glycolated lipids (such as PEG2000-DMG and PEG2000-DSPE) were mixed in absolute ethyl alcohol according to an optimized mole ratio. The obtained ethyl alcohol solution and a sodium acetate buffer solution (25 mM, pH=5.0) dissolved with Luc-mRNA (TriLink) were mixed according to a volume ratio of 1:3 by using a micro-fluidic preparation system to prepare a coarse solution of the lipid nanoparticles. Then, the coarse solution was dialyzed for 6 h under the condition of 1×PBS and temperature control at 4° C. by using a dialysis box (Fisher, MWCO 20,000). Before use, filtration was performed by a 0.22 μm microporous filtering membrane. A mass ratio of the amino lipid compound to luciferase mRNA (Luc mRNA) was about 10:1.

Expression of Lipid Nanoparticles

What is claimed is:

1. An amino lipid with the structure as shown in Formula (I):

(I)

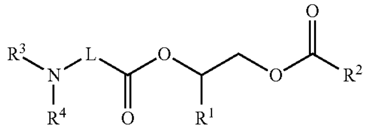

$R^1$ is independently selected from E6 and E7,

E6

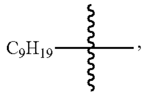

E7

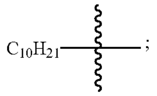

$R^2$ is C71,

C71

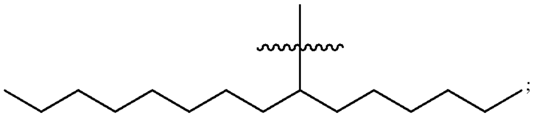

wherein $R^3$, $R^4$ and L form a carboxylic acid structure of

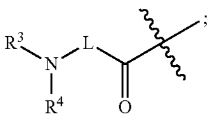

and

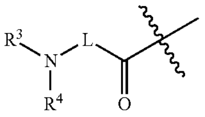

is one selected from:

A9

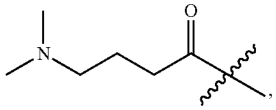

A12

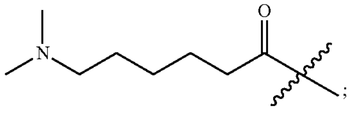

wherein $R^3$ is methyl, $R^4$ is methyl and L is propane-1,3-diyl or pentane-1,5-diyl.

2. The amino lipid according to claim 1, being one selected from compounds of the following structures:

E6C71A12

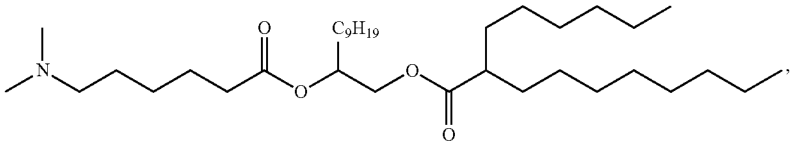

E7C71A9

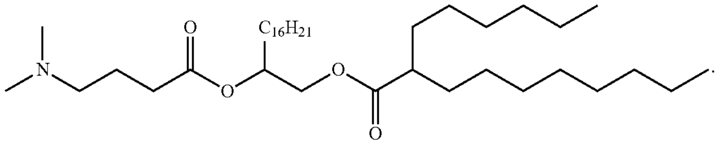

3. A method of preparing the amino lipid according to claim 1, comprising the following steps:

S1: performing a solvent-free reaction between the compound $R^2COOH$ and an epoxide compound in the presence of $FeCl_3$ and Py as catalysts, resulting in a reaction system, wherein the structure of the epoxide compound is described as follows:

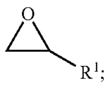

and

S2: adding $R^3R^4NLCOOH$ to the reaction system obtained from step S1, and allowing the mixture to react in the presence of a condensation agent to obtain the amino lipid;

wherein $R^1$, $R^2$, $R^3$, $R^4$, and L are the same as those in claim 1.

4. A composition for a nucleic acid administration system, wherein the composition comprises the amino lipid according to claim 1 as a raw material.

5. A composition formed by the amino lipid according to claim 1 and other lipids, wherein the composition and a nucleic acid drug form a drug preparation, and the nucleic acid drug comprises DNA and RNA.

6. The composition according to claim 5, wherein the composition comprises 30 mol %-50 mol % of an amino lipid, 40 mol %-52% mol % of a structure lipid, 5 mol %-20% mol % of an auxiliary lipid and 0.5 mol %-5% mol % of a PEG lipid, wherein the total molar content of the four above ingredients is 100 mol %; and wherein the mass ratio of the amino lipid to the nucleic acid in the composition is in the range of 1:1-50:1.

7. The composition according to claim 6, wherein the structure lipid comprises cholesterol and a cholesterol derivative thereof.

8. The composition according to claim 6, wherein the auxiliary lipid comprises DSPC, DSPE, DOPE, DOPC and DOPS.

9. The composition according to claim 6, wherein the PEG lipid comprises PEG-DMG and PEG-DSPE.

10. The composition according to claim 6, wherein the composition is administered by aerosolization administration, intravenous injection, subcutaneous injection, intramuscular injection, ophthalmic administration.

* * * * *